US007306815B2

(12) United States Patent
Gourdin et al.

(10) Patent No.: US 7,306,815 B2
(45) Date of Patent: *Dec. 11, 2007

(54) COMPOSITIONS ENRICHED IN PHENOLIC COMPOUNDS AND METHODS FOR PRODUCING THE SAME

(75) Inventors: Gerald T. Gourdin, Boulder, CO (US); Steven L. Richheimer, Westminster, CO (US); Michael S. Tempesta, El Granada, CA (US); David T. Bailey, Boulder, CO (US); Rebecca L. Nichols, Broomfield, CO (US); F. Joseph Daugherty, Omaha, NE (US); Delano R. Freeberg, Algonquin, IL (US)

(73) Assignee: Phenolics, LLC, Omaha, NE (US)

( * ) Notice: Subject to any disclaimer, the term of this patent is extended or adjusted under 35 U.S.C. 154(b) by 233 days.

This patent is subject to a terminal disclaimer.

(21) Appl. No.: 10/764,231

(22) Filed: Jan. 23, 2004

(65) Prior Publication Data

US 2005/0010040 A1    Jan. 13, 2005

Related U.S. Application Data

(63) Continuation-in-part of application No. 10/302,264, filed on Nov. 22, 2002, which is a continuation-in-part of application No. 09/943,158, filed on Aug. 30, 2001, now Pat. No. 6,780,442.

(60) Provisional application No. 60/229,205, filed on Aug. 31, 2000.

(51) Int. Cl.
*A61K 36/00* (2006.01)
*A61K 36/45* (2006.01)
*C07H 17/00* (2006.01)
*C07D 311/00* (2006.01)

(52) U.S. Cl. .......... 424/725; 424/732; 514/27; 514/783; 536/8; 549/403

(58) Field of Classification Search ........ 424/725, 424/732; 514/27, 783; 536/8; 549/403
See application file for complete search history.

(56) References Cited

U.S. PATENT DOCUMENTS 4,452,822 A    6/1984   Shrikhande
(Continued)

FOREIGN PATENT DOCUMENTS

DE    3027933    2/1981
(Continued)

OTHER PUBLICATIONS

Lisa Rapport, Brian Lockwood, "(6) Proanthocyanidins and Grape Seed Extract," The Pharmaceutical Journal, vol. 266, (Apr. 28, 2001) pp. 581-584.
(Continued)

*Primary Examiner*—Taylor Victor Oh
(74) *Attorney, Agent, or Firm*—Hogan & Hartson LLP

(57) ABSTRACT

Provided are processes for the preparation of compositions enriched in phenolic compounds from a crude plant extract. One process includes a novel column purification step using a polymer resin that releasably adsorbs the phenolic compounds but does not retain polar non-phenolic compounds, wherein the resin comprises aromatic rings substituted with one or more electron-withdrawing groups. This invention also includes compositions enriched in phenolic compounds. This invention encompasses methods of using the phenolic-enriched compositions for treating warm-blooded animals, including humans, infected with paramyxovaridae such as respiratory syncytial virus, orthomyoxovaridae such as influenza A, B, and C, parainfluenza, Herpes viruses such as HSV-1 and HSV-2, and Flaviviruses such as West Nile Virus, and for treating inflammation such as caused by arthritis, stress and digestive disease. The compositions are also useful as meat additives to inhibit food-borne pathogens.

29 Claims, 54 Drawing Sheets

U.S. PATENT DOCUMENTS

| | | | |
|---|---|---|---|
| 4,500,556 | A | 2/1985 | Langston |
| 4,863,956 | A | 9/1989 | Gabetta et al. |
| 5,200,186 | A | 4/1993 | Gabetta et al. |
| 5,211,944 | A | 5/1993 | Tempesta |
| 5,484,594 | A * | 1/1996 | Frangi et al. ............... 424/766 |
| 5,494,661 | A | 2/1996 | Tempesta |
| 5,525,341 | A | 6/1996 | Walker et al. |
| 5,646,178 | A | 7/1997 | Walker et al. |
| 5,773,262 | A * | 6/1998 | Ariga et al. ............... 435/118 |
| 5,780,060 | A | 7/1998 | Levy et al. |
| 5,804,597 | A | 9/1998 | Yamakoshi et al. |
| 5,814,494 | A * | 9/1998 | Ariga et al. ............... 435/118 |
| 5,886,029 | A | 3/1999 | Dhaliwal |
| 5,912,363 | A | 6/1999 | Nafisi-Movaghar et al. |
| 5,968,517 | A | 10/1999 | Duncan et al. |
| 6,099,854 | A | 8/2000 | Howard et al. |
| 6,103,756 | A | 8/2000 | Gorsek |
| 6,194,469 | B1 | 2/2001 | Nair et al. |
| 6,200,569 | B1 | 3/2001 | Cheng |
| 6,210,681 | B1 | 4/2001 | Walker et al. |
| 6,303,125 | B1 | 10/2001 | Ofek et al. |
| 6,423,365 | B1 | 7/2002 | Nair |
| 6,544,581 | B1 | 4/2003 | Shrikhande et al. |
| 6,780,442 | B2 * | 8/2004 | Bailey et al. ............... 424/732 |
| 2001/0002407 | A1 | 5/2001 | Nair et al. |
| 2001/0021398 | A1 | 9/2001 | Walker et al. |

FOREIGN PATENT DOCUMENTS

| | | | |
|---|---|---|---|
| GB | 1235379 | * | 6/1971 |
| WO | WO 02/17732 A2 | | 3/2002 |

OTHER PUBLICATIONS

L. Gao and G. Mazza, Characterization, Quantitation, and Distribution of Anthocyanins and Colorless Phenolics in Sweet Cherries, Journal of Agricultural and Food Chemistry 48 (2) pp. 343-346.

M. Azar, E. Verette, and S. Brun, "Identification of Some Phenolic Compounds in Bilberry Juice *Vaccinium myrtillus*," Journal of Food Science, vol. 52, No. 5 (1987) pp. 1255-1257.

D.L. Madhavi, S. Juthangkoon, K. Lewen, M.D., Berber-Jimenez, M.A.L. Smith, "Characterization of Anthocyanins from *Ajuga pyramidalis* Metallica Crispa Cell Cultures," J. Agric. Food Chem, vol. 44. No. 4, (1996) pp. 1170-1176.

Elliott Middleton, Jr., "Effect of Plant Flavonoids on Immune and Inflammatory Cell Function," Flavonoids in the Living Systems (1998) pp. 175-182.

L. Yeap Foo, Yinrong Lu, Amy B. Howell and Nicholi Vorsa, A-Type Proanthocyanindin Trimers from Cranberry that Inhibit Adherence of Uropathogenic P-Fimbriated *Escherichia coli* J Nat Prod., vol. 63 (9) (2000) pp. 1225-1228.

R. Ubillas, S.D. Jolad, et al., "SP-303 an Antiviral Oligomeric Proanthocyanidin from the Latex of Croton lechieri (Sange de Drago)," Phytomedicine vol. 1, pp. 77-106 (1994).

Lai Yep Foo, Yinrong Lu, Amy B. Howell, Nicholi Vorsa, "The structure of cranberry proanthocyanidins which inhibit adherence of uropathogenic P-fimbriated *Escherichia coli* in vitro," Photochemistry, vol. 54, 173-181. (2000).

Ronald L. Prior, Sheryl A. Lazarus, et al., "Identification of Procyanidins and Anthocyanins in Blueberries and Cranberries (Vaccinium Spp.) Using High-Performance Liquid Chromatography/Mass Spectrometry."

Horotoshi Tamura and Atsushi Yamagami, "Antioxidative Activity of Monoacylated Anthocyanins Isolated from Muscat Baily A Grape," J.Argic. FoodChem, 1994, 42, 1612-1615.

Ronald L. Prior, Guohua Cao, Antonio Martin, Emin Scofic, et al., "Antioxidant Capacity As Influenced by Total Phenolic and Anthocyanin Content, Maturity, and Variety of Vaccinium Species," J. Agric Food Chem, 1988, vol. 46 2686-2693.

Geza Hrazdin, "Column Chromatographic Isolation of the Anthocyanidin-3, 5-Diglucosides from Grapes," J. Agr Food Chem., vol. 18, No. 2, 1970 243-245.

International Search Report, PCT/US01/27107, Feb. 1, 2002.

A.M. Fine. "Oligomeric Proanthocyanidin Complexes: History, Structure, and Phytopharmaceutical Applications", [online]. [retrieved on Feb. 28, 2002]. Retrieved from the Internet URL: http://www.thorne.com/almedrev/fulltext/oligo5-2.html.

"Oligomeric Proanthocyanidins (Pycnogenols)" [online]: [retrieved on May 1, 2002]. Retrieved from the Internet URL http://www.thorne.com/pycnogenols.html.

Sterling. "Proanthocyanidin Power" [online]: [retrieved on May 1, 2002]. Retrieved from the Inter URL: http://www.healthwellexchange.com/nutritionsciencenews/nsn_backs/Jun_00/proantho.cfm.

M. Sterling, "Got Anthocyanins?" [online], [retrieved on Feb. 28, 2002]. Retrieved from the Internet URL: http://www.healthwatchexchange.com/nutritionsciencenews/nsn_backs/Dec_01/antho.cfm.

M. Sterling, Proanthocyanindin Power [online], [retrieved on Feb. 28, 2002]. Retrieved from the Internet URL http:/www.healthwellexchange.com/nutritionsciencenews/nsn_backs/Jun_00/proantho.cfm.

PCT International Search Report PCT/US05/24003.

Anderson, et al. "Isolation and Characterization of Polyphenol Type-A Polymers from Cinnamon with Insulin-like Biological Activity"; Journal of Agricultural and Food Chemistry; 2004; pp. 65-70; vol. 52, No. 1; American Chemical Society.

Internet Website http://www.herbsmd.com/shop/xq/asp/pid.8505/qx/productdetail.asp Thermogenic Fat Burners by Weider; pp. 1-2, 2002.

* cited by examiner

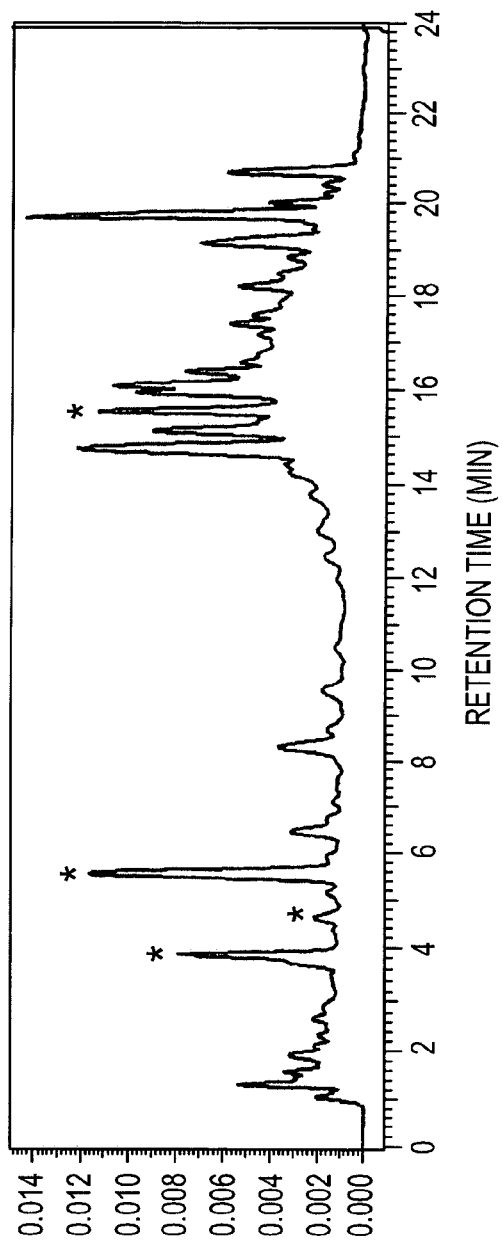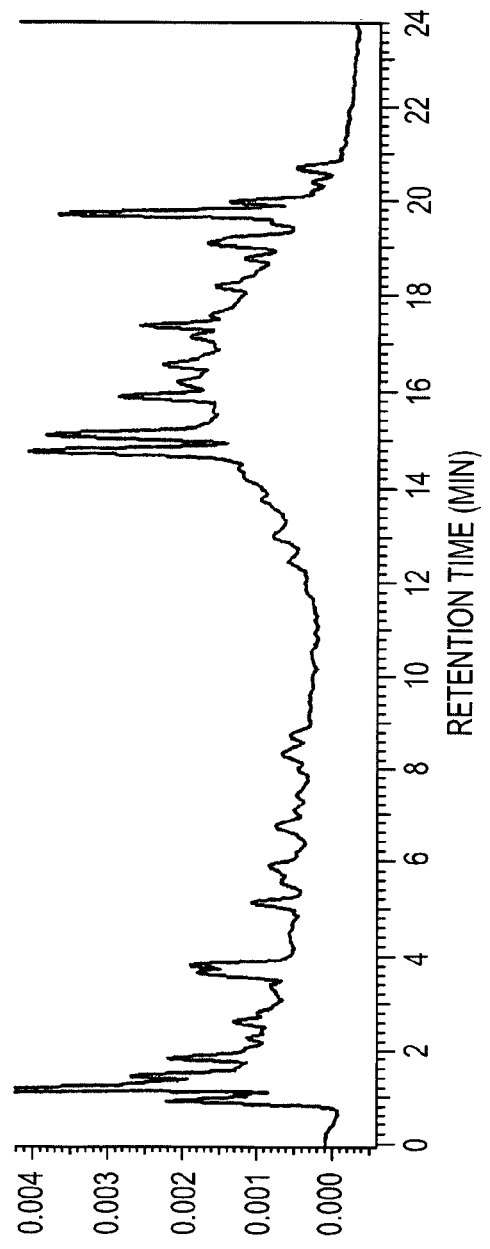

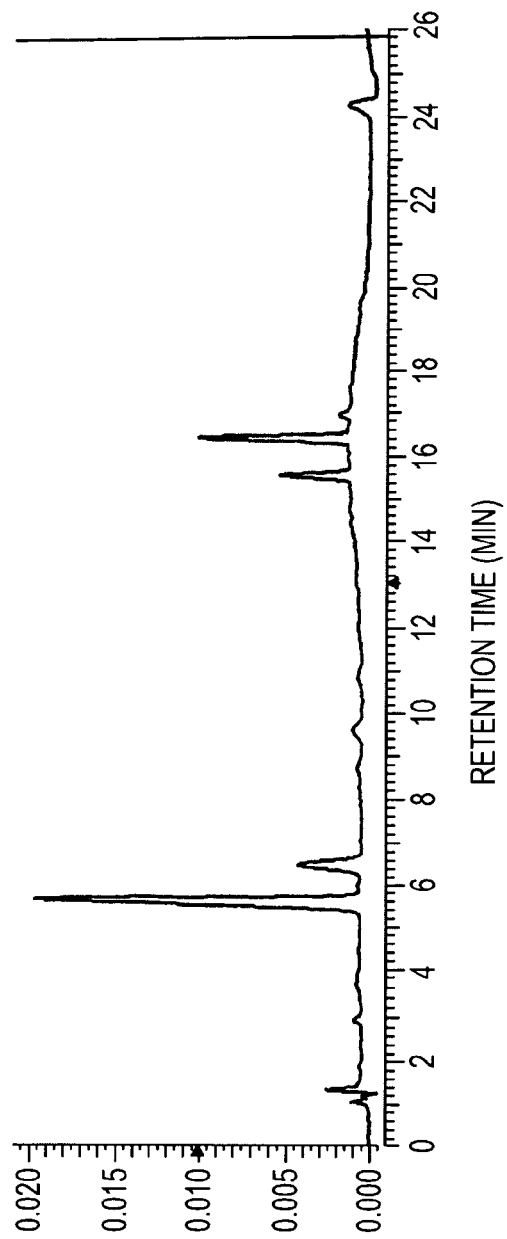
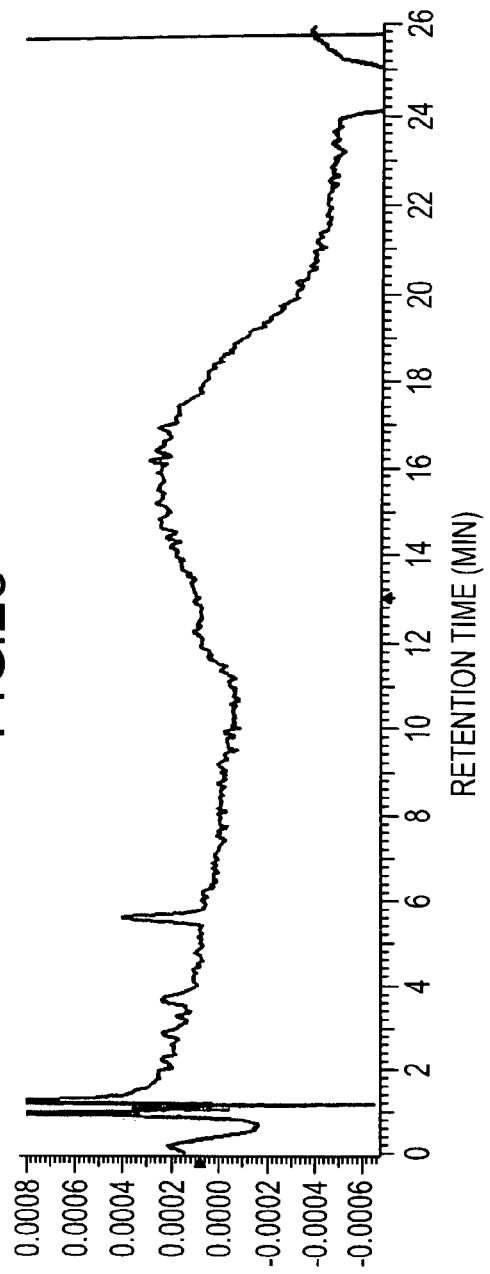

COMPOSITIONS ENRICHED IN PHENOLIC COMPOUNDS AND METHODS FOR PRODUCING THE SAME

CROSS-REFERENCE TO RELATED APPLICATIONS

This application is a Continuation-in-Part of U.S. patent application Ser. No. 10/302,264, filed Nov. 22, 2002, which is a Continuation-in-Part application of U.S. patent application Ser. No. 09/943,158, filed Aug. 30, 2001, now U.S. Pat. No. 6,780,442 which claims priority to U.S. Provisional Application No. 60/229,205, filed Aug. 31, 2000, the disclosures of which are incorporated herein by reference in their entirety.

BACKGROUND OF THE INVENTION

1. Field of the Invention

The present invention relates to the extraction and purification of flavonoid compounds from plant material, and more specifically to the production of compositions enriched in phenolic compounds.

2. Description of the Prior Art

Flavonoid compounds are present in all aerial parts of plants, with high concentrations found in the skin, bark, and seeds. Such compounds are also found in numerous beverages of botanical origin, such as tea, cocoa, and wine. The flavonoids are a member of a larger family of compounds called polyphenols. That is, these compounds contain more than one hydroxyl group (OH) on one or more aromatic rings. The physical and chemical properties, analysis, and biological activities of polyphenols and particularly flavonoids have been studied for many years.

Anthocyanins are a particular class of naturally occurring flavonoid compounds that are responsible for the red, purple, and blue colors of many fruits, vegetables, cereal grains, and flowers. For example, the colors of fruits such as blueberries, bilberries, strawberries, raspberries, boysenberries, marionberries, cranberries, elderberries, etc. are due to many different anthocyanins. Over 300 structurally distinct anthocyanins have been identified in nature. Because anthocyanins are naturally occurring, they have attracted much interest for use as colorants for foods and beverages.

Recently, the interest in anthocyanin pigments has intensified because of their possible health benefits as dietary antioxidants. For example, anthocyanin pigments of bilberries (*Vaccinium myrtillus*) have long been used for improving visual acuity and treating circulatory disorders. There is experimental evidence that certain anthocyanins and other flavonoids have anti-inflammatory properties. In addition, there are reports that orally administered anthocyanins are beneficial for treating diabetes and ulcers and may have antiviral and antimicrobial activities. The chemical basis for these desirable properties of flavonoids is believed to be related to their antioxidant capacity. Thus, the antioxidant characteristics associated with berries and other fruits and vegetables have been attributed to their anthocyanin content.

Proanthocyanidins, also known as "oligomeric proanthocyanidins," "OPCs," or "procyanidins," are another class of naturally occurring flavonoid compounds widely available in fruits, vegetables, nuts, seeds, flowers, and barks. Proanthocyanidins belong to the category known as condensed tannins. They are the most common type of tannins found in fruits and vegetables, and are present in large quantities in the seeds and skins. In nature, mixtures of different proanthocyanidins are commonly found together, ranging from individual units to complex molecules (oligomers or polymers) of many linked units. The general chemical structure of a polymeric proanthocyanidin comprises linear chains of flavonoid 3-ol units linked together through common C(4)-C(6) and/or C(4)-C(8) bonds. $^{13}$C NMR has been useful in identifying the structures of polymeric proanthocyanidins, and recent work has elucidated the chemistry of di-, tri-, and tetrameric proanthocyanidins. Larger oligomers of the flavonoid 3-ol units are predominant in most plants and are found with average molecular weights above 2,000 Daltons and containing 6 or more monomer units (Newman, et al., *Mag. Res. Chem.*, 25:118 (1987)).

Considerable recent research has explored the therapeutic applications of proanthocyanidins, which are primarily known for their antioxidant activity. However, these compounds have also been reported to demonstrate antibacterial, antiviral, anticarcinogenic, anti-inflammatory, anti-allergic, and vasodilatory actions. In addition, they have been found to inhibit lipid peroxidation, platelet aggregation, capillary permeability and fragility, and to affect enzyme systems including phospholipase A2, cyclooxygenase, and lipoxygenase. For example, proanthocyanidin monomers (i.e., anthocyanins) and dimers have been used in the treatment of diseases associated with increased capillary fragility and have also been shown to have anti-inflammatory effects in animals (Beladi, I. et al., *Ann. N.Y. Acad. Sci.*, 284:358 (1977)). Based on these reported findings, oligomeric proanthocyanidins (OPCs) may be useful components in the treatment of a number of conditions (Fine, A. M., *Altern. Med. Rev.* 5(2):144-151 (2000)).

Proanthocyanidins may also protect against viruses. In in vitro studies, proanthocyanidins from witch hazel (*Hamamelis virginiana*) killed the Herpes simplex 1 (HSV-1) virus (Erdelmeier, C. A., Cinatl, J., *Plant Med.* June: 62(3):241-5 (1996); DeBruyne, T., Pieters, L., *J. Nat. Prod.* Jul: 62(7):954-8 (1999)). Another study was carried out to determine the structure-activity relationships of the antiviral activity of various tannins. It was found that the more condensed the chemical structure, the greater the antiviral effect (Takechi, M., et al., *Phytochemistry*, 24:2245-50 (1985)). In another study, proanthocyanidins were shown to have anti-Herpes simplex activity in which the 50 percent effective doses needed to reduce herpes simplex plaque formation were two to three orders of magnitude less than the 50 percent cytotoxic doses (Fukuchi, K., et al., *Antiviral Res.*, 11:285-298 (1989)).

Cyclooxygenase (COX-1, COX-2) or prostaglandin endoperoxide H synthase (PGHS-1, PGHS-2) enzymes are widely used to measure the anti-inflammatory effects of plant products (Bayer, T., et al., *Phytochemistry*, 28:2373-2378 (1989); and Goda, Y., et al., *Chem. Pharm. Bull.*, 40:2452-2457 (1992)). COX enzymes are the pharmacological target sites for nonsteroidal anti-inflammatory drugs (Humes, J. L., et al., *Proc. Natl. Acad. Sci. USA.*, 78:2053-2056 (1981); and Rome, L. H., et al., *Proc. Natl. Acad. Sci. U.S.A.*, 72:4863-4865 (1975)). Two isozymes of cyclooxygenase involved in prostaglandin synthesis are cyclooxygenase-1 (COX-1) and cyclooxygenase-2 (COX-2) (Hemler, M., et al., *J. Biol. Chem.*, 25:251, 5575-5579 (1976)). It is hypothesized that selective COX-2 inhibitors are mainly responsible for anti-inflammatory activity (Masferrer, J. L., et al., *Proc. Natl. Acad. Sci. USA.*, 91:3228-3232 (1994)). Flavonoids are now being investigated as anti-inflammatory substances, as well as for their structural features for cyclooxygenase (COX) inhibition activity.

Due to the above characteristics and benefits of anthocyanins and proanthocyanidins, much effort has been put forth toward extracting these compounds from fruits, vegetables, and other plant sources. In addition to proanthocyanidins and anthocyanins, plants, fruits, and vegetables also contain other compounds such as mineral salts, common organic acids such as citric or tartaric acid, carbohydrates, flavonoid glycosides and catechins. It is often desirable to separate the anthocyanins and proanthocyanidins from other naturally occurring compounds. Anthocyanins have been extracted from plants and fruits by various procedures. One method of extracting anthocyanins employs the addition of bisulfate to form zwitterionic species. The extract is passed through an ion exchange column which adsorbs the zwitterionic anthocyanin adducts, and the adsorbed anthocyanins are eluted from the resin with acetone, alkali, or dimethylformamide (DMF). Disadvantages of this process include the presence of bisulfate, which interferes with adsorption of anthocyanins, thereby requiring multiple column adsorptions. Elution with alkali degrades the anthocyanins considerably, while DMF is not a recognized food additive and therefore must be completely removed before the anthocyanins can be added to any food products.

In order to capture these flavonoid compounds, well-defined and precise processing and separation techniques are needed. Nafisi-Movaghar, et al. in U.S. Pat. No. 5,912,363 describe a method for the extraction and purification of proanthocyanidins from plant material comprising heating an aqueous mixture of plant material, filtering the aqueous solution through an ultrafiltration membrane to remove larger molecular weight polymers and particulates to produce a permeate containing extracted proanthocyanidins, separating the proanthocyanidins from the liquid by contacting the permeate with an adsorbent material which is capable of releasably retaining the proanthocyanidins, and eluting the retained proanthocyanidins with a polar solvent. However, this method uses a very hot extraction temperature, which can cause degradation of the proanthocyanidins. Further, the ultrafiltration removes some of the low molecular weight polyphenolic material from the final product.

Many processes known in the art for extracting and isolating proanthocyanidins and/or anthocyanins from various plant materials use toxic and/or environmentally hazardous materials. Consequently, the current methods available for isolating and purifying proanthocyanidins are not easily scaled up to an efficient commercial process where disposal considerations of various chemicals and solvents play an important role in the overall feasibility of the process. Further, proanthocyanidins and anthocyanins must be isolated in a manner that minimizes their natural tendency toward degradation.

There is still a need, therefore, for an efficient process for isolating and purifying compositions containing phenolic compounds such as proanthocyanidins for uses in nutraceuticals and pharmaceuticals that is cost-effective, scalable, economically sound, does not require the use of toxic solvents or reagents, and isolates the phenolic compounds from plant material in a manner that minimizes their tendency toward degradation.

SUMMARY OF THE INVENTION

The present invention provides simplified and economic methods for the extraction, isolation, and purification of compositions enriched in phenolic compounds. More specifically, one aspect of this invention provides a method of preparing compositions enriched in phenolic compounds comprising: (a) providing a crude extract of one or more plant materials that contain phenolic compounds, said extract comprising phenolic compounds and polar non-phenolic compounds; (b) filtering the crude extract; (c) contacting the crude extract with a polymer resin which releasably adsorbs said phenolic compounds but does not substantially retain said polar non-phenolic compounds, wherein said polymer resin comprises aromatic rings substituted with one or more electron-withdrawing groups; (d) washing said resin with a wash eluent to elute said polar non-phenolic compounds; (e) eluting the resin with a first eluent and collecting a first fraction containing said phenolic compounds; (f) eluting the resin with a second eluent and collecting a second fraction containing said phenolic compounds; and (g) isolating the fractions from step (e) or from step (f) or combining said fractions from steps (e) and (f) to obtain a composition enriched in said phenolic compounds and substantially depleted of said polar non-phenolic compounds. Examples of suitable substituted polymer resins include, but are not limited to, brominated polystyrene resins and protonated tertiary amine-substituted styrene divinylbenzene copolymer resins.

A further aspect of this invention provides a method of preparing compositions enriched in proanthocyanidins, comprising: (a) extracting one or more plant materials containing proanthocyanidins with a solvent to provide a crude extract, said extract comprising proanthocyanidins, anthocyanins, other small phenolics and non-phenolic compounds; (b) filtering the crude extract by means other than size exclusion filtration; (c) contacting the crude extract with a resin comprising unsubstituted aromatic rings which retains said anthocyanins and releasably adsorbs said proanthocyanidins but does not substantially retain the polar non-phenolic compounds; (d) washing said resin with a wash eluent to elute the polar non-phenolic compounds; (e) eluting the resin at with a first eluent and collecting a first fraction containing said proanthocyanidins; (f) eluting the resin with a second eluent and collecting a second fraction containing said proanthocyanidins; and (g) isolating the fractions from step (e) or from step (f) or combining said fractions from steps (e) and (f) to obtain a composition enriched in proanthocyanidins and substantially depleted of said polar non-phenolic compounds. Examples of suitable unsubstituted resins include, but are not limited to, polystyrene divinylbenzene copolymers. In one embodiment, the first and/or second elutions are performed at about room temperature.

This invention further provides methods of fractionating the phenolic-enriched compositions to separate polar proanthocyanidins from non-polar proanthocyanidins and compositions enriched in polar proanthocyanidins and compositions enriched in non-polar proanthocyanidins. The polar proanthocyanidins were found to have biological activities that are different than the non-polar proanthocyanidins.

This invention further provides phenolic-enriched, polar proanthocyanidin enriched and non-polar proanthocyanidin enriched compositions isolated by the methods of this invention.

When the phenolic-enriched compositions of this invention are analyzed by reversed-phase HPLC on a C-18 lipophilic column, characteristic sets of elution peaks of compounds absorbing at 280 nm and 510 nm are observed. For example, in one embodiment the phenolic-enriched compositions of this invention are characterized as having a characteristic set of elution peaks in the region between 60 and 75 minutes in an HPLC trace substantially as illustrated in FIGS. 10-13 when the HPLC analysis is performed as described herein.

When the phenolic-enriched compositions of this invention are analyzed by IR spectrometry, characteristic absorption peaks of compounds substantially as shown in FIGS. 33-40 are observed. The compositions of this invention are useful as nutraceuticals and pharmaceuticals. For example, the compositions of this invention are useful as anti-infective (e.g., antiviral, anti-UTI and antimicrobial) agents and as anti-inflammatory agents.

The foregoing and other features, utilities and advantages of the invention will be apparent from the following more particular descriptions of preferred embodiments of the invention and as illustrated in the accompanying drawings and as particularly pointed out in the appended claims.

BRIEF DESCRIPTION OF THE DRAWINGS

The accompanying drawings, which are incorporated herein and form a part of the specification, illustrate non-limiting embodiments of the present invention, and together with the description, serve to explain the principles of the invention.

In the Drawings:

FIG. 21 is an HPLC chromatogram at 280 nm of an elderberry non-polar proanthocyanidin composition ("fraction 6") isolated during VLC chromatography on C-18 media and before purification on a Sephadex LH-20 column, in which the non-proanthocyanidin peaks are marked with an asterisk.

FIG. 22 is an HPLC chromatogram at 280 nm of the elderberry non-polar proanthocyanidin composition ("fraction 8") after purification on a Sephadex LH-20 column.

FIG. 23 is an HPLC chromatogram at 368 nm of an elderberry non-polar proanthocyanidin composition ("fraction 6") isolated during VLC chromatography on C-18 media and before purification on a Sephadex LH-20 column.

FIG. 24 is an HPLC chromatogram at 368 nm of an elderberry non-polar proanthocyanidin composition ("fraction 8") after purification on a Sephadex LH-20 column.

DETAILED DESCRIPTION OF THE INVENTION

Figure 1:
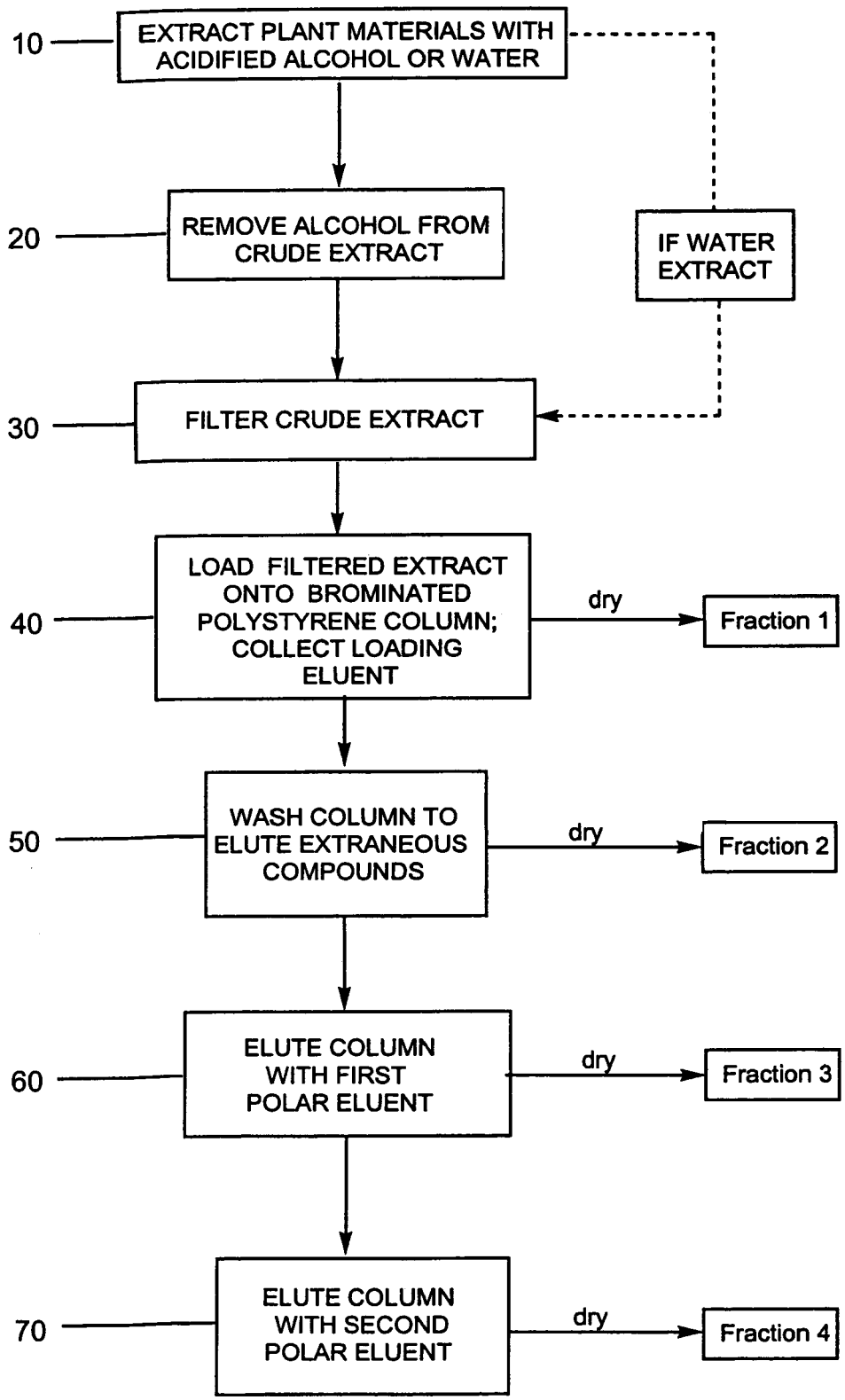
FIG. 1 is a flow chart of one embodiment of a method for preparing a phenolic-enriched composition according to the method of this invention.

This invention provides methods for preparing compositions enriched in phenolic compounds from plant materials that naturally contain phenolic compounds such as anthocyanins and proanthocyanidins. The method of this invention further provides purified compositions enriched for phenolic compounds (also referred to herein as "phenolic-enriched compositions"). The terms "phenols" and "phenolic compounds" are used interchangeably herein and include monomeric, oligomeric and polymeric compounds having one or more phenolic groups, and include, but are not limited to, anthocyanins, proanthocyanidins, and flavonoids.

As used herein, the term "phenolic-enriched composition" refers to a composition enriched in one or more phenolic compounds and having substantially depleted levels of polar non-phenolic compounds present in crude extracts of plants, fruits, berries, and vegetables. Examples of such polar non-phenolic compounds include, but are not limited to, sugars, cellulose, pectin, amino acids, proteins, nucleic acids, and water.

The phenolic enriched compositions are typically prepared from plant material extracts or concentrates. The term "extract" refers to a substance derived from a plant source that naturally contains phenolic compounds, including extracts prepared from the whole plant or from various parts of the plant, such as the fruits, leaves, stems, roots, bark, etc. Thus, the method of this invention is not limited to the particular part of the plant used to prepare the extract. The present method can use any source of phenolic compounds, most typically from botanically derived whole plant material or portions of the plant material such as the skins, peels, fruits, nuts, seeds, grain, foliage, stems, woody or fibrous material, and the like, other than tree bark. Thus, the method of this invention is not limited to the particular part of the plant used to prepare the extract. Most colored fruits, berries, and vegetables are known to contain phenolic compounds. Suitable phenolic compound-containing plant materials that can be used in the methods of this invention include, but are not limited to, blueberries, bilberries, elderberries, plums, blackberries, strawberries, red currants, black currants, cranberries, cherries, red raspberries, black raspberries, grapes, hibiscus flowers, bell peppers, beans, peas, red cabbage, purple corn, violet sweet potatoes, olives, pomegranates, mangosteens, apples, hawthorn, gooseberries, and oranges, including the whole plant material or the skins, peels, fruits, nuts, hulls, or seeds thereof, excluding tree bark. The raw plant material may be used either as is (wet) or may be dried prior to extraction. Optionally, the raw plant material may be presorted by separating and removing the components low in anthocyanins and proanthocyanidins prior to extraction.

In one embodiment, the phenolic-enriched compositions of the present invention are obtained by extracting and purifying a plant material containing phenolic compounds. It is known that plant materials containing phenolic compounds have unique and characteristic profiles, that is, the amounts and types of phenolic compounds in each plant material are specific to the particular plant material. Therefore, a phenolic-enriched composition isolated from a specific plant material according to this invention will be different from compositions isolated from other plant materials.

FIG. 1 is a flowchart showing the steps of one embodiment of the process of this invention in which a composition enriched in phenolic compounds may be prepared. The process of this invention provides an economical and efficient method of obtaining compositions enriched in phenolic compounds by eliminating several process steps and by reducing the amount of reagents needed in the process, thereby reducing production costs and waste disposal issues.

Extraction Phase

During this phase, an extract is prepared by extracting phenolic compounds (e.g., proanthocyanidins, anthocyanins and other phenolic compounds) and non-phenolic compounds including polar non-phenolic compounds from a fresh or dried plant material (FIG. 1, step 10). Those skilled in the art will recognize that a variety of extraction methods are available in the literature, such as vat extraction, percolation, countercurrent extraction, etc. The particular method of extraction employed is not essential to the process of the present invention. The degree of comminution of the plant material prior to the extraction process should provide sufficient particulate surface area for the extraction solvent to effectively contact.

In one embodiment of the process shown in FIG. 1, the extraction step (step 10) is accomplished by placing fresh or dried plant material in an appropriate amount of extraction solvent for a sufficient period of time. The amount of plant material to extraction solvent used in the extraction process varies between about 2:1 to about 1:20 on a gram to milliliter basis. In one embodiment, the ratio of plant material to extraction solvent is between about 1:4 and 1:8. The mixture of plant material and solvent is optionally heated, depending on the amount of anthocyanins present in the plant material. That is, if a plant material typically contains about 0.05% to 2% anthocyanins, the extraction is preferably performed at or below 45° C. However, if the plant material typically contains less than 0.05% anthocyanins, the extraction can be performed at temperatures ranging from room temperature up to greater than 85° C., depending on the stability of the phenolic compounds. For example, cranberries, which contain very little anthocyanins, can be extracted at temperatures around 100° C. without affecting the stability of the proanthocyanidins contained in the cranberry extract.

In one embodiment, the extraction solvent comprises an acidified alcohol solution having about 0 to 95% ethanol in water and about 0 to 3 wt. %, more preferably about 0.006 to 0.012 wt. %, of a suitable acid. In another embodiment, the extraction solvent comprises an acidified alcohol solution having between about 0-100% methanol in water and about 0 to 3 wt. % of a suitable acid. Suitable acids that may be used in the extraction step include, but are not limited to, sulfuric acid ($H_2SO_4$), acetic acid (HOAc) or hydrochloric acid (HCl). Alternatively, the plant material can be extracted with a non-acidified extract solvent and then acid can be added to the extract. The presence of an acid in the extraction solvent or the extract helps to minimize degradation of the anthocyanins. Thus, in one embodiment the acidic conditions are maintained throughout most of the steps of the process of this invention as illustrated in FIG. 1.

The crude extract contains phenolic compounds such as proanthocyanidins, anthocyanins and other phenolics, as well as undesired polar non-phenolic materials such as sugars, pectin, plant sterols, fatty acids, triglycerides, water, and other compounds. Solid residue contained in the crude extract is separated from the liquid portion, and the solids are either re-extracted as described above or discarded.

In one embodiment of step 10 (FIG. 1), pectinase is added either to the plant material or to the extraction solvent before or during the extraction process. Alternatively, the pectinase can be added to the crude extract after the extraction process is complete. The pectinase serves to prevent the extract from gelling at any point during or after the extraction process so that it will remain flowable during the column purification. The amount of pectinase added will depend in part on the amount of plant material used to prepare the extract or the amount of pectinase already present in the extract. Typically, the pectinase is added in an amount between about 0 and 0.12% by weight of the plant material.

With continued reference to FIG. 1, if either an ethanolic or methanolic extraction solvent was used to prepare the crude extract in step 10, the crude extract is concentrated (step 20) until the crude extract contains less than 6% ethanol or methanol, preferably maintaining a temperature of 45° C. or less during concentration. Water is added to dilute the concentrated crude extract, and the diluted crude extract is either concentrated and diluted again with water prior to step 30, or is carried on directly to step 30 without performing a second dilution. Of course, if water was used as the extraction solution in the preparation of the crude extract, step 20 is not necessary, and in this case the crude extract from step 10 is taken directly on to step 30 as shown by the dashed arrow in FIG. 1.

Filtration Phase

Step 30 of the process shown in FIG. 1 comprises optionally filtering the crude extract from step 10 or 20 to remove solids from the crude extract. The inventors discovered that by adjusting the extraction conditions as described for step 10, the amount of undesirable non-phenolic compounds that precipitate from the crude extract by filtration in step 30 is increased, and therefore a portion of undesired materials can be removed from the extract prior to the adsorption phase. Various filtration methods may be employed in filtration step 30 of the process of this invention. One filtration method that may be employed in step 30 comprises adding a measured amount of a filter aid such as diatomaceous earth or cellulose to the crude extract. The mixture of crude extract and filter aid is preferably shaken or stirred until homogeneous and filtered through a bed of filter aid. The bed is washed with an aqueous acidic solution, preferably about 0.006% aqueous sulfuric acid.

Other filtration methods that may be used in step 30 of FIG. 1 include filtering the crude extract using filtration means other than size exclusion filtration. For example, one embodiment comprises filtering the crude extract through a bed of sand or a 30 micron polypropylene filter that is preferably covered with glass wool. Yet another filtration method comprises using a bag filter (a bag-shaped cloth filter composed of polyethylene or polypropylene), which may advantageously be placed in-line with the purification column of step 40 described below. Thus, it is to be understood that the filters described above are filters for removing solids rather than size exclusion filters such as ultrafiltration membranes which are used in the art to remove molecules of a certain size from a solution.

Adsorption Phase

To isolate the phenolic compounds according to the method shown in FIG. 1, the filtered extract isolated in step 30 is contacted with a resin that releasably absorbs the phenolic compounds such as proanthocyanidins and anthocyanins, but which retains less of the undesired polar non-phenolic materials that were present in the filtered extract. In one embodiment, the resin is a polymer resin having one or more aromatic rings that are substituted with one or more electron-withdrawing functional groups. Each aromatic ring can be substituted with one or more similar or different electron-withdrawing groups, including, but not limited to, halogens (F, Cl, Br, I), protonated alkyl amines (including primary, secondary and tertiary amines), sulfonic acids, trihalomethyl, COOH, $NO_2$, and CN. Alternatively, the polymer can comprise a mixture of substituted aromatic rings and unsubstituted aromatic rings. Such resins are referred to herein as "substituted resins." Preferably the resin is an approved food-grade resin.

One example of a substituted resin suitable for purposes of this invention is a brominated polystyrene resin such as SP-207 (Supelco; Bellafonte, Pa.), manufactured by Mitsubishi Chemical America. SP-207 resin is a macroporous, brominated styrenic polymeric bead type resin designed for reversed-phase chromatographic applications, and has a particle size distribution between about 250-800 microns and a pore size range between about 100-300 Å. The bromination of the aromatic rings provides increased hydrophobicity to the polystyrene resin, and is designed to provide a resin having increased selectivity for hydrophobic molecules relative to conventional styrene-divinylbenzene polymeric reversed-phase supports. Because of its tight binding properties, brominated polystyrene resin is not typically used in the purification of natural products.

Thus, since it was known that certain conventional polystyrene resins tend to bind phenolic compounds such as proanthocyanidins and anthocyanins so tightly that it is very difficult to elute such compounds from the polystyrene resin, it was expected that the brominated polystyrene resin would bind phenolic compounds even tighter. Therefore, it was not expected that a brominated polystyrene resin would be suitable for the purification of phenolic compounds. However, the inventors surprisingly and unexpectedly discovered that the brominated polystyrene resin binds phenolic compounds such as proanthocyanidins and anthocyanins less tightly than non-brominated polystyrene resins, but still allows for the separation of phenolic compounds from undesired polar non-phenolic compounds. That is, it was discovered that a high purity composition enriched in phenolic compounds could be obtained by purifying the filtered extract isolated in step 30 on a brominated polystyrene resin.

Another substituted resin suitable for providing a high purity composition enriched in phenolic compounds according to this invention is a protonated form of a tertiary amine-substituted polymer such as Dowex Optipore SD-2 (sold by Dow Chemical, Midland, Mich.) which is a food grade macroporous styrene divinylbenzene copolymer having tertiary amine functional groups on the aromatic rings.

While not wishing to be bound by any theory, it is believed that since substituents such as bromine and protonated tertiary amines are electron withdrawing, they reduce the electron density of the aromatic ring to which they are attached, and this effect may be sufficient to reduce their hold on the positively charged anthocyanins. In contrast, the aromatic rings of an unsubstituted styrene divinylbenzene copolymer resin have more electron density and so are more strongly attracted to the positive charge of the anthocyanins, causing the anthocyanins to be held more tightly to this resin. Thus, substituted resins such as Dowex Optipore SD-2 and the Mitsubishi SP207 resin may releasably hold anthocyanins, whereas unsubstituted benzene divinylbenzene copolymer resins will hold but are less likely to release the anthocyanins.

In yet another embodiment, the resin is a polymer comprising unsubstituted aromatic rings, referred to herein as an "unsubstituted aromatic resin" or an "unsubstituted polymer resin." One example of an unsubstituted aromatic resin suitable for purposes of this invention is a polystyrene divinylbenzene copolymer resin such as Mitsubishi SP70. This resin has the following physical properties: mean particle diameter of 250 mm; specific surface area of 700 $m^2/g$; and specific pore radius of 65 Å. The SP70 resin surprisingly releasably retains proanthocyanidins but does not release anthocyanins as easily. While this would not normally be considered an acceptable resin for obtaining a product enriched in both anthocyanins and proanthocyanidins, it is suitable for isolating proanthocyanidin-enriched products from a plant material that does not contain a significant amount of anthocyanins, such as plum. In this embodiment, the steps of loading the extract onto the resin and eluting the desired compounds from the resin are performed at room temperature. An example of isolating proanthocyanidins from plum using SP70 is described in Example 21.

In one embodiment of the method shown in FIG. 1, the filtered extract isolated in step 30 is loaded onto a column packed with a substituted resin such as SP207. Preferably the resin has a particle size distribution between about 200-700 microns and a pore size range between about 50-300 Å (step 40). However, while step 40 is described herein in terms of contacting the extract with a resin packed into a column, such a description is merely for ease of explanation. Thus, the resin need not be packed into a column in order to perform the method of this invention. The amount of filtered extract that is loaded onto the column depends on the plant material used to prepare the crude extract. For example, when the crude extract is prepared from bilberries, about 16-30 grams of phenolic compounds may be loaded per liter of SP207 resin. As another example, when the crude extract is prepared from blueberries, about 15-45 grams of phenolic compounds may be loaded per liter of SP207 resin. When the crude extract is prepared from elderberries, about 15-40 grams of phenolic compounds may be loaded per liter of SP207 resin. The filtered extract may be diluted with water prior to loading if the solids concentration in the concentrated crude extract exceeds 200 grams per liter. The fractions eluting during column loading in step 40 (FIG. 1) are collected as "fraction 1."

Subsequent to loading the filtered crude extract onto the resin, undesired polar non-phenolic materials (e.g., sugars, salts, organic acids, etc.) which have little or no affinity for the adsorbent are eluted from the resin with an aqueous wash solvent comprising at least 0.003% acid such as aqueous sulfuric acid, aqueous acetic acid or aqueous hydrochloric acid (FIG. 1, step 50). For example, about three column volumes of 0.006% aqueous sulfuric acid or 0.1% aqueous acetic acid can be used to elute the extraneous materials. The eluent is collected as "fraction 2."

With continued reference to FIG. 1, the column is next eluted with a first eluent comprising a polar organic solvent such as about 50 to 70% ethanol/water or about 50 to 90% methanol/water (step 60). Typically about 2 to 12 column volumes of eluting solvent are used in Step 60. In one embodiment, the first eluent contains about 0.003% of an acid such as sulfuric acid, hydrochloric acid or acetic acid. The fraction(s) collected during elution step 60 are collected as "fraction 3." "Fraction 3" contains a portion of the phenolic compounds contained in the crude extract, and is particularly enriched in anthocyanins and/or proanthocyanidins.

After the majority of the anthocyanins (if present in the extract) have been eluted from the column, as determined by UV-VIS spectroscopy, the column is eluted with a second eluent (step 70; FIG. 1) comprising a polar organic solvent comprising a greater percentage of ethanol or methanol than the solvent used to elute the anthocyanins (step 60). For example, the second eluent may comprise about 70 to 90% ethanol/water or about 75 to 100% methanol/water. The fraction(s) collected during elution step 70 are collected as "fraction 4." "Fraction 4" contains an additional portion of the phenolic compounds originally contained in the crude extract and is typically enriched in proanthocyanidins. "Fraction 4" may also contain anthocyanins not isolated during elution step 60.

Each of steps 50, 60 and 70 is typically performed at about room temperature, although higher or lower temperatures can be used, provided that the temperature is not one that will degrade the phenolic compounds.

Recovery of the phenolic compounds in "fraction 3" and "fraction 4" can be accomplished in any convenient manner such as by evaporation, distillation, freeze-drying, and the like, to provide a phenolic-enriched composition of this invention, provided that the recovery method is performed at a temperature that will not degrade the phenolic compounds.

The above-described process is suitable for preparing compositions sufficiently enriched in phenolic compounds for use as nutraceuticals from a variety of plant materials that contain phenolic compounds including, but not limited to, elderberries, plums, blueberries, bilberries, blackberries, strawberries, red currants, black currants, cranberries, cherries, raspberries, grapes, hibiscus flowers, bell peppers, beans, peas, red cabbage, purple corn, and violet sweet potatoes. In one embodiment, the enriched compositions of this invention contain at least 10-80% phenolic compounds. In another embodiment, the compositions contain at least 12% phenolic compounds. In yet another embodiment, the compositions contain at least 25% phenolic compounds.

In an alterative embodiment for isolating phenolic compounds, and in particular proanthocyanidins from a plant material, a plant material extract prepared as described above is loaded onto an unsubstituted aromatic resin such as Mitsubishi SP70 (a polystyrene divinylbenzene copolymer resin). As stated, unsubstituted aromatic resins releasably retain proanthocyanidins but do not release anthocyanins as easily, which makes this type of resin suitable for isolating proanthocyanidin-enriched products from a plant material that does not contain a significant amount of anthocyanins, such as plums. In one embodiment, the steps of loading the extract onto the resin and eluting the desired compounds from the resin are performed at about room temperature. For example, a crude or filtered plant extract (prepared as described above) or a fruit concentrate is loaded at room temperature onto a column packed with an unsubstituted polystyrene divinylbenzene copolymer. Subsequently, undesired polar non-phenolic materials (e.g., sugars, salts, organic acids, etc.) that have little or no affinity for the adsorbent are eluted from the resin at room temperature with an aqueous wash solvent comprising at least 0.003% of an acid, such as aqueous sulfuric acid, aqueous acetic acid or aqueous hydrochloric acid. Phenolic compounds are then eluted from the column at room temperature with a first eluent comprising a polar organic solvent such as about 50 to 70% ethanol/water or about 50 to 90% methanol/water to obtain a first eluent fraction(s), and then at room temperature with a second eluent comprising a greater percentage of ethanol or methanol (e.g., 70 to 90% ethanol/water or about 75 to 100% methanol/water) to obtain a second eluent fraction(s). The first and second elution fractions can be assayed for phenolic content if desired to determine whether further elutions will elute additional phenolic compounds from the resin. As stated, the unsubstituted polystyrene divinylbenzene copolymer typically retains anthocyanins, and therefore it is not necessary to adjust the elution conditions in order to separate anthocyanins from proanthocyanidins according to this embodiment when the goal is to isolate a proanthocyanidin-enriched composition.

Proanthocyanidin Separation Phase

Figure 12:
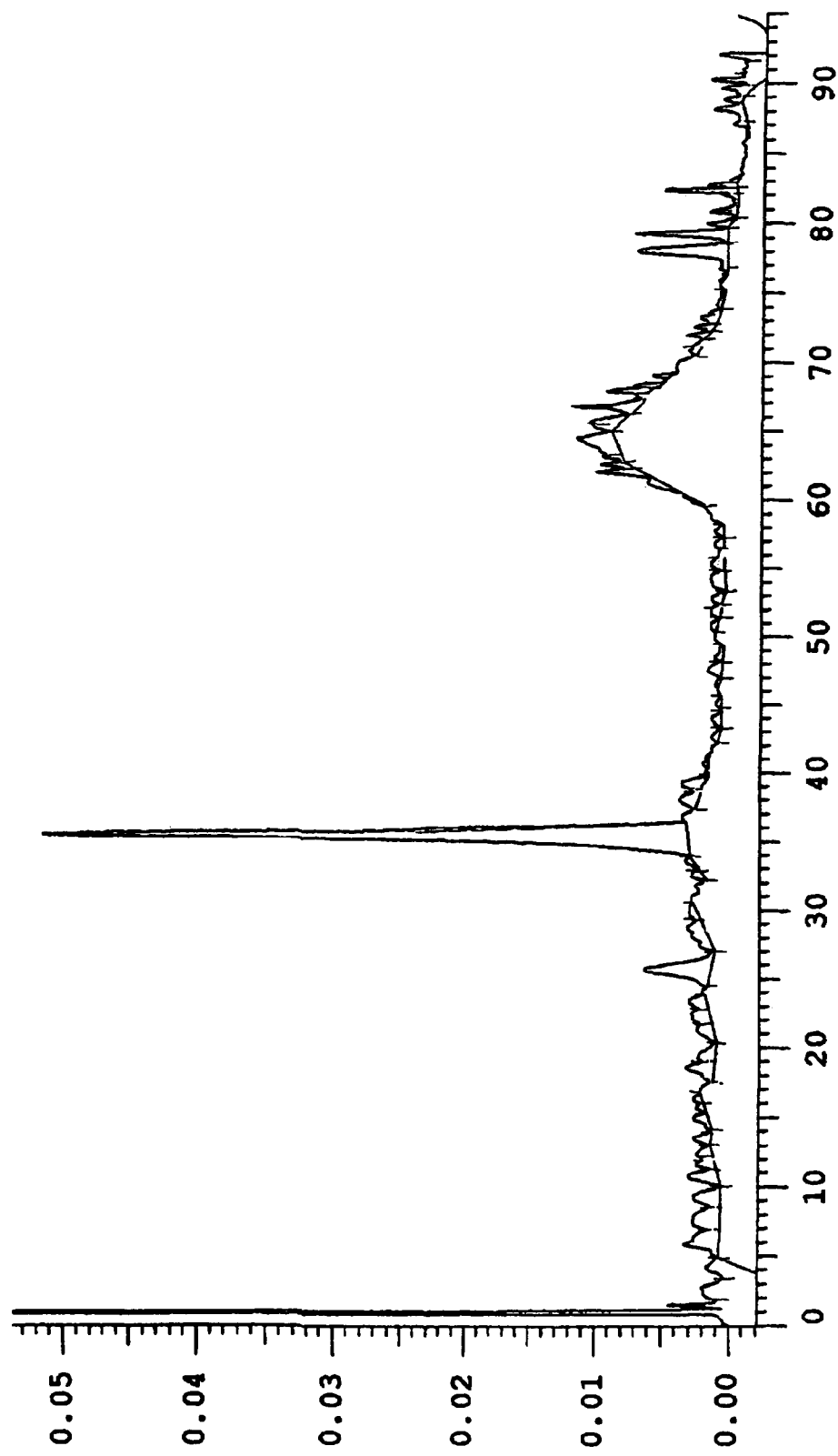
FIG. 12 is an HPLC chromatogram at 280 nm of a fourth fraction eluted with 90% ethanol during column purification of an elderberry extract on a brominated polystyrene resin.
Figure 13:
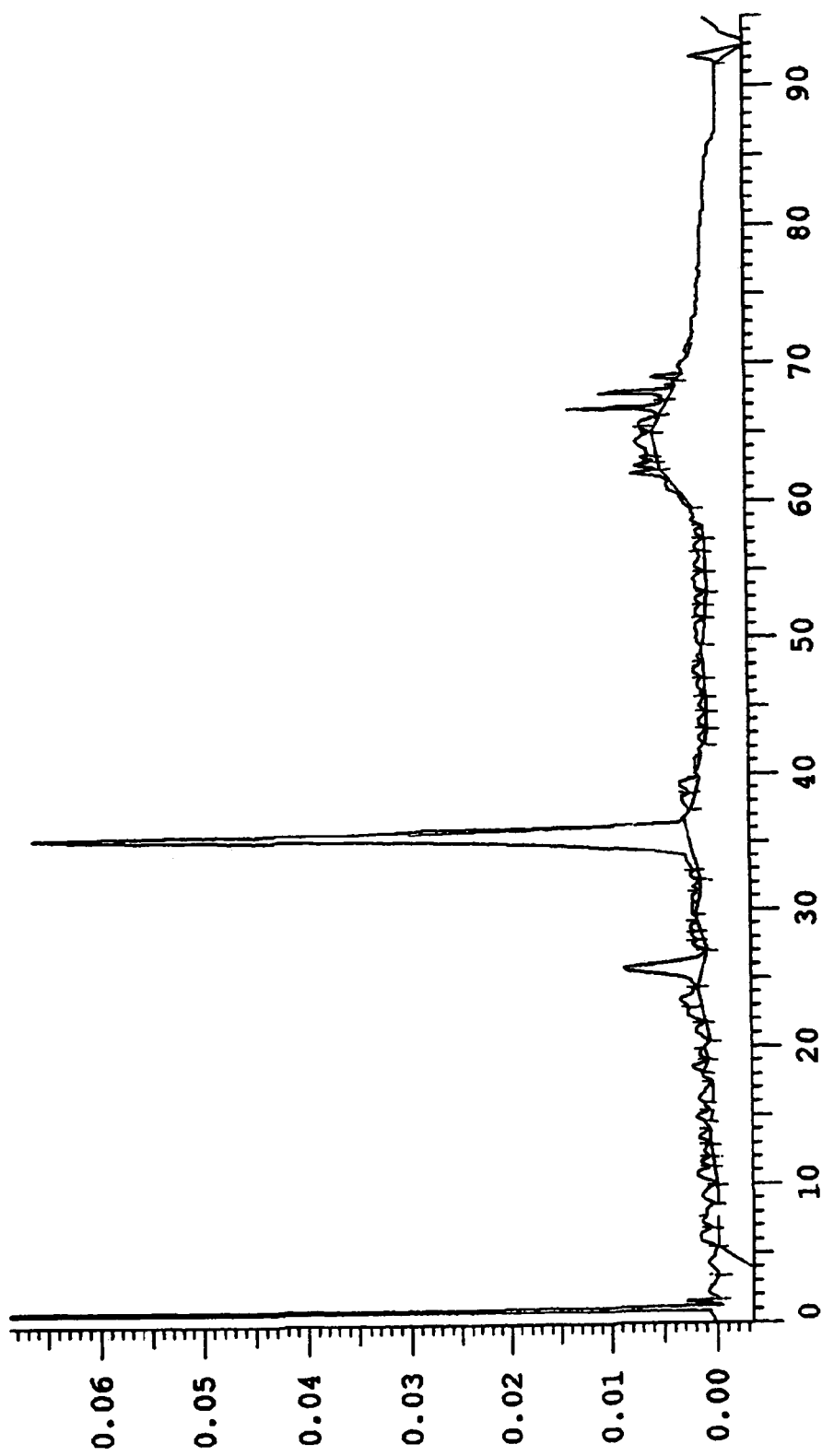
FIG. 13 is an HPLC chromatogram at 510 nm of a fourth fraction eluted with 90% ethanol during column purification of an elderberry extract on a brominated polystyrene resin.

It was discovered that the phenolic-enriched compositions, and in particular the compositions isolated from "fraction 3," "fraction 4," or a combination thereof, isolated as described herein from a substituted resin produce similar HPLC chromatograms having the characteristic peaks such as those shown in FIGS. 12 and 13. For example, the HPLC chromatograms of all phenolic-enriched compositions prepared from plant material containing phenolic compounds and isolated using a brominated polystyrene resin according to the method illustrated in FIG. 1 and isolated from "fraction 4" were found to contain characteristic peaks between 60 and 75 minutes similar to peaks in the chromatogram shown in FIGS. 12 and 13 for a "fraction 4" composition isolated from elderberries. The phenolic-enriched compositions of this invention, isolated either from "fraction 3," "fraction 4," or a combination thereof, and prepared according to this invention have anti-infective (e.g., antiviral) and anti-inflammatory activity, as described below in detail.

When the phenolic-enriched compositions of this invention are analyzed by IR spectrometry, characteristic peaks from the phenolic compounds are also observed. More specifically, the phenolic-enriched compositions of this invention are characterized as having IR absorption peaks substantially as illustrated in FIGS. 33-40.

Figure 15:
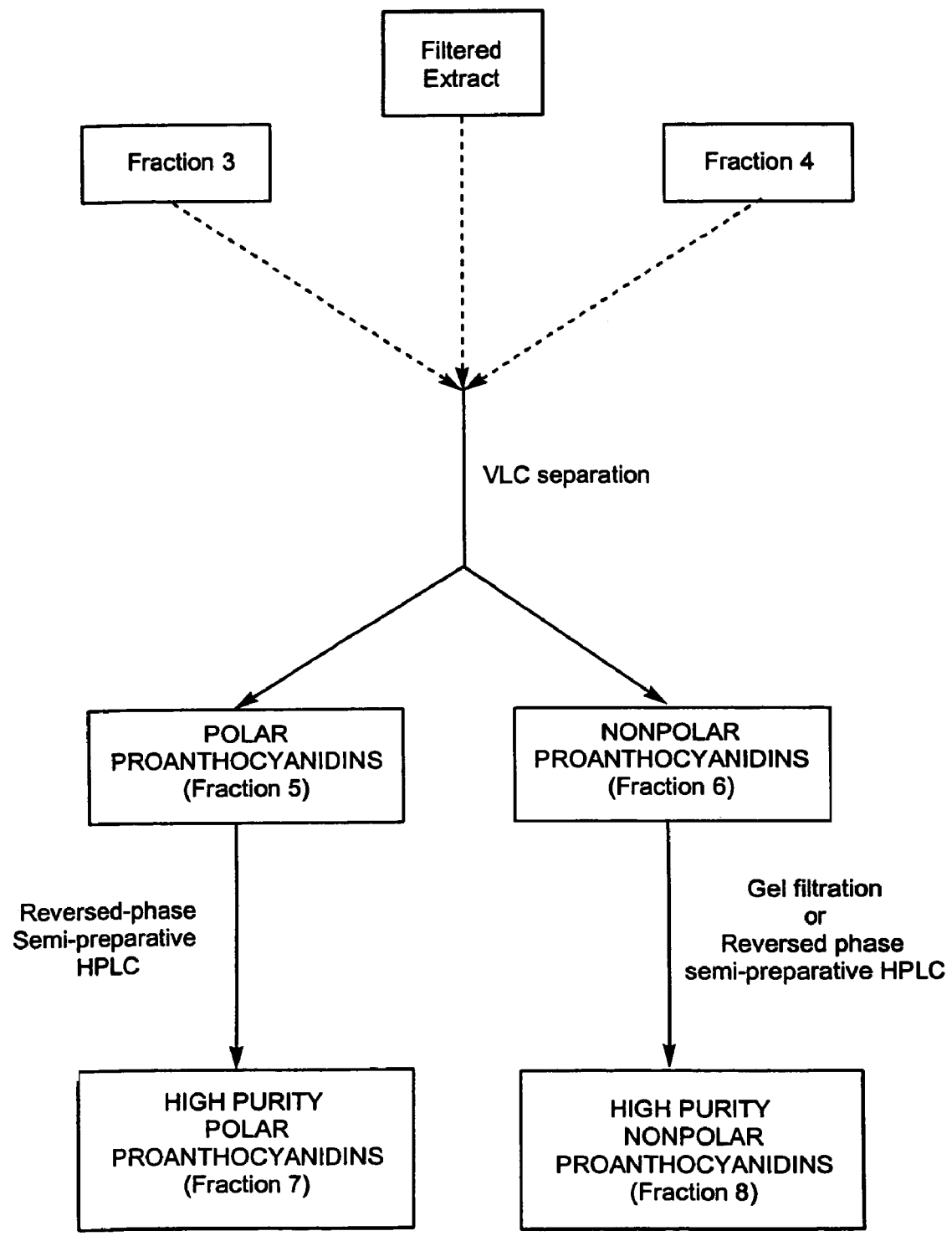
FIG. 15 is a flow chart of a method for separating polar proanthocyanidins from non-polar proanthocyanidins.

It was also discovered that the phenolic-enriched compositions (e.g., "fraction 3," "fraction 4," or a combination thereof) could be further partitioned into a "polar" proanthocyanidin-enriched fraction and a "non-polar" proanthocyanidin-enriched fraction using low pressure Vacuum Liquid Chromatography (VLC) on a reversed-phase lipophilic column, such as a C-18 column as described in detail in Example 11 and as shown in FIG. 15. For example, a "fraction 3" composition isolated from an elderberry extract was dissolved in water and loaded onto a C-18 column. The column was washed with 100% water to collect materials that are not strongly retained by the C-18 media. The flow through and wash fractions were combined as "fraction 5" and contained the more polar proanthocyanidins. Thus, "fraction 5" is referred to herein as the "polar" proanthocyanidin-enriched fraction (FIG. 15). The polar proanthocyanidin-enriched "fraction 5" from elderberry typically has some purple color, suggesting that the polymers in this fraction contain at least one or more cationic anthocyanidin subunits within the oligomeric proanthocyanidin chains. The VLC column was then eluted with 30 to 100% methanol to collect the proanthocyanidins that are more strongly retained by the C-18 media used in the low-pressure column. The methanol fractions were combined as "fraction 6" and contained proanthocyanidins that are less polar than those collected in "fraction 5." Thus, "fraction 6" is referred to herein as the "non-polar" proanthocyanidin-enriched fraction (FIG. 15). The non-polar proanthocyanidin-enriched "fraction 6" has little if any color, suggesting that the oligomeric proanthocyanidin chains in this fraction do not contain cationic anthocyanidin subunits.

Thus, the present invention provides a method of conveniently separating the polar proanthocyanidins from the non-polar proanthocyanidins contained in either "fraction 3," "fraction 4," or a combination thereof. It was also found that a polar proanthocyanidin-enriched "fraction 5" and non-polar proanthocyanidin-enriched "fraction 6" could be isolated directly by loading a crude filtered aqueous extract (FIG. 1, step 30) onto a C-18 VLC column. It is to be understood that the terms "polar" and "non-polar" when used to describe the isolated proanthocyanidin-enriched fractions 5 and 6, respectively, refer to the polarity of the proanthocyanidins in fractions 5 and 6 relative to one another, that is, how the particular fractions behave on a C-18 VLC column. The polar proanthocyanidin-enriched compositions (fraction 5) and the non-polar proanthocyanidin-enriched compositions ("fraction 6") of this invention have substantially reduced levels of anthocyanins, as discussed in the Examples.

The polar and non-polar proanthocyanidin-enriched fractions ("fraction 5" and "fraction 6," respectively) were found to have different biological activities, and the non-polar fraction was found to have greater antiviral activity than the polar fraction in certain assays as described in Example 17.

Each of the polar and non-polar proanthocyanidin-enriched fractions 5 and 6, respectively, can be purified further as shown in FIG. 15 and as described in Examples 12-14. For example, the polar proanthocyanidin-enriched "fraction 5" isolated during the VLC separation can be loaded onto a semi-preparative C-18 HPLC column that releasably retains the polar proanthocyanidins. The column is then washed with a solvent gradient comprising increasing percentages of acetonitrile, methanol or ethanol to elute most of the anthocyanins and other polar compounds, and then with at least 60% acetonitrile, methanol or ethanol to elute "fraction 7" containing the purified polar proanthocyanidins (FIG. 15). Additionally, the non-polar proanthocyanidin-enriched "fraction 6" isolated during the VLC separation can be further purified by gel filtration or reversed-phase semi-preparative HPLC. Gel filtration, also called size exclusion or gel permeation chromatography, is a liquid chromatography technique that separates molecules according to their size. This type of media retains smaller compounds, while the larger non-polar proanthocyanidin-enriched "fraction 8" (FIG. 15) elute with the flow-through eluent. The purified polar and non-polar proanthocyanidin-enriched fractions 7 and 8, respectively, of this invention have substantially reduced levels of anthocyanins and flavonoids, and also have substantially reduced levels of polar non-phenolic compounds. It was further observed that the purified polar and non-polar proanthocyanidin-enriched "fraction 7" and "fraction 8", respectively, have different biological activities.

Uses

The phenolic-enriched compositions ("fraction 3," "fraction 4," or a combination thereof), polar proanthocyanidin-enriched compositions (fractions 5 and 7), and non-polar proanthocyanidin-enriched compositions (fractions 6 and 8) of this invention possess a range of biological activities. For example, the compositions of this invention were found to have antiviral activities, as described in Examples 15 and 16. The compositions of this invention can be used either alone or in combination with other antiviral agents to prevent and/or treat diseases induced by or complicated with viral infections from viruses including, but not limited to, influenza A, B, and C, parainfluenza virus, adenovirus type 1, Punta Toro Virus A, Herpes simplex virus I and II, rhinovirus, West Nile virus, Varicella-zoster virus and measles virus. Accordingly, the phenolic-enriched compositions, polar proanthocyanidin-enriched compositions, and non-polar proanthocyanidin-enriched compositions of this invention can be advantageously used in prophylactic and therapeutic applications against diseases induced by such viruses by administering a therapeutically effective amount of a composition of this invention.

Proanthocyanidins have also been investigated as anti-inflammatory substances due to their inhibition of cyclooxygenase (COX) activity. It has been shown that it is desirable for anti-inflammatory substances to be selective for COX-2 inhibition rather than COX-1 inhibition. Accordingly, another aspect of this invention comprises a method of treating inflammatory diseases in mammals comprising administering a therapeutically effective amount of a phenolic-enriched composition, polar proanthocyanidin-enriched composition, or a non-polar proanthocyanidin-enriched composition of this invention. For example, phenolic-enriched compositions isolated as fractions 3 and 4 during purification of a blueberry extract were found to have high COX-2/COX-1 inhibition selectivity and an $IC_{50}$ of 108 µg/mL (Example 17). The compositions of this invention can be used either alone or in combination with other anti-inflammatory agents to prevent or inhibit inflammatory responses. Such responses may be caused by conditions or diseases including, but not limited to, osteoarthritis, allergenic rhinitis, cardiovascular disease, upper respiratory diseases, wound infections, neuritis and hepatitis.

It is known that proanthocyanidins isolated from cranberries and blueberries inhibit bacteria from attaching to the bladder wall, thereby reducing the potential for maladies such as urinary tract infections (Howell, A. B., et al., *New England J. Medicine*, 339:1085-1086 (1998)). It has been postulated that proanthocyanidins exert their effect by inhibiting the adhesion of bacteria. Accordingly, another aspect of this invention comprises a method of preventing or treating urogenital infections in a mammal comprising administering an effective amount of a phenolic-enriched composition, polar proanthocyanidin-enriched composition, or a non-polar proanthocyanidin-enriched composition of this invention in an amount sufficient to prevent, reduce, or eliminate the symptoms associated with such infections. The compositions of this invention can be used either alone or in combination with other antimicrobial agents.

It is further known that proanthocyanidins are potent antioxidants. For example, the antioxidant effects of proanthocyanidins are presumed to account for many of their benefits on the cardiovascular and immune systems. Accordingly, the phenolic-enriched compositions, polar proanthocyanidin-enriched compositions, and non-polar proanthocyanidin-enriched compositions of this invention may be used as dietary supplements (e.g., dietary antioxidants) and for the treatment of disorders in humans and mammals. For example, the compositions of this invention may be used for improving visual acuity and for treating circulatory disorders, diabetes, and ulcers.

It is known that dried plums can serve as an effective microbial agent, suppressing the growth of pathogens in meat products. For example, D. Fung (Kansas State University) tested dried plum puree as a microbe inhibitor in ground meat products. Using a 3% by weight level of dried plum puree, a 99% kill rate against virulent pathogens such as *E. coli* and *Salmonella* in ground meats was reported (2002 press release available at the following URL: http://www.mediarelations.ksu.edu). It is believed that the phenolic compounds in part are responsible for this beneficial effect. Accordingly, the phenolic-enriched compositions, polar proanthocyanidin-enriched compositions, and non-polar proanthocyanidin-enriched compositions of this invention may be used as meat additives to prevent the growth of pathogens in meat products.

The phenolic-enriched compositions, polar proanthocyanidin-enriched compositions, and non-polar proanthocyanidin-enriched compositions of this invention can also be combined with immunoactive agents, including but not limited to, *arabinogalactan*, species of *Echinacea*, vitamins, minerals, polysaccharides and *astragalus*.

The phenolic-enriched compositions, polar proanthocyanidin-enriched compositions, and non-polar proanthocyanidin-enriched compositions of this invention can also be combined with antimutagenic agents including, but not limited to, green tea extracts, catechins, epicatechins, epigallocatechins, gallocatechins, and flavonoids.

The phenolic-enriched compositions, polar proanthocyanidin-enriched compositions, and non-polar proanthocyanidin-enriched compositions of this invention may be formulated as pills, capsules, liquids, or tinctures. In formulating compositions according to this invention, a wide range of excipients may be used, the nature of which will depend, of course, on the intended mode of application of the composition. Examples of excipients include preservatives, carriers, and buffering, thickening, suspending, stabilizing, wetting, emulsifying, coloring and flavoring agents, and in particular carboxy vinyl polymers, propylene glycol, ethyl alcohol, water, cetyl alcohol, saturated vegetable triglycerides, fatty acid esters or propylene glycol, triethanolamine, glycerol, starch, sorbitol, carboxymethyl cellulose, lauryl sulphate, dicalcium phosphate, lecithin, etc.

EXAMPLES

Example 1

Purification of Bilberry Using a Water Extraction

Three extractions were performed on 1 kg of dried bilberry raw material. The first extraction used 6 L of water and the other two extractions used 4 L of water. All extractions were acidified with concentrated sulfuric acid to an acid concentration of 5 g/L. There was approximately an 88% recovery of anthocyanins into the crude extract. Exactly 2.3 L of the crude extract were filtered through a 30 micron polypropylene filter with a layer of glass wool over the filter. The glass wool was changed once and the filter rinsed with deionized water. The final volume of the filtrate was 2.43 L with a 90.9% recovery of anthocyanins in the filtrate.

A column was packed with brominated polystyrene resin SP-207 (Supelco; Belefonte, Pa.) and equilibrated with 0.1% acetic acid. The column was loaded with 2.24 L of the filtrate at a solids concentration of 29.8 g/L using a flow rate of 2.2 mL/min. The loading bleed was less than 0.9% of the loaded anthocyanins with an overall loss of 4.07% of the anthocyanins in the loading and first two column washes. There was an 88.4% recovery of the anthocyanins in the elution step and an anthocyanins mass balance of 92.5%. A few hundred milliliters of elution product were evaporated to dryness on a rotary evaporator and then lyophilized. Final assay of the dried product was by standard spectrophotometric determination of absorbance at 535 nm against a delphinidin chloride standard (102 absorbance units/g/L at 1.0 cm). The enriched composition contained 43% total anthocyanins by weight.

Example 2

Purification of Bilberry Using a 70% Ethanol Extraction

Dried bilberry raw material (667 g), assayed at 2.0% anthocyanins, was extracted by percolation using 70% ethanol/water containing 3% sulfuric acid by volume. The solids in the crude extract contained 3.9% by weight total anthocyanins. One liter of the first extraction volume was mixed with 100 mL deionized water and evaporated in vacuo to about 460 mL to remove the alcohol. Deionized water (300 mL) was added to the mixture, and an additional 170 mL of liquid were evaporated. Deionized water (210 mL) was added to make the final volume 800 mL. To the aqueous mixture was added 150 g of Celite 512 (0.5 to 0.9 g of Celite per gram of solids). The mixture was shaken until homogeneous. The Celite/extract mixture was poured over a 30 g bed of damp Celite 512 under vacuum. Upon completion of filtration, the bed was washed with 1.20 L of 1% aqueous sulfuric acid in 200 mL increments. The filtrate volume was 1855 mL. To the filtrate was added 145 mL of deionized water to give a final volume of 2.0 L.

A portion of the filtrate (695 mL) was loaded at 2.2 mL/minute (1.3 mL/min/cm$^2$) onto a column loaded with 170 mL brominated polystyrene resin (SP-207). This gave a load value of 17 g of anthocyanins per liter of column media. The column was washed with one column volume of 0.1% aqueous acetic acid followed by 2.5 column volumes of 0.1% HOAc/10% ethanol/90% water. The column was then eluted with 10 column volumes of 70% ethanol/water, and the 70% ethanol fractions were combined and concentrated in vacuo at 60° C. and 50 mbar to provide a dark, dry, shiny amorphous solid ("fraction 3"). Final assay of the dried product was by standard spectrophotometric determination of absorbance at 535 nm against a delphinidin chloride standard (102 absorbance units/g/L at 1.0 cm). The enriched composition contained 32% total anthocyanins by weight.

Figure 2:
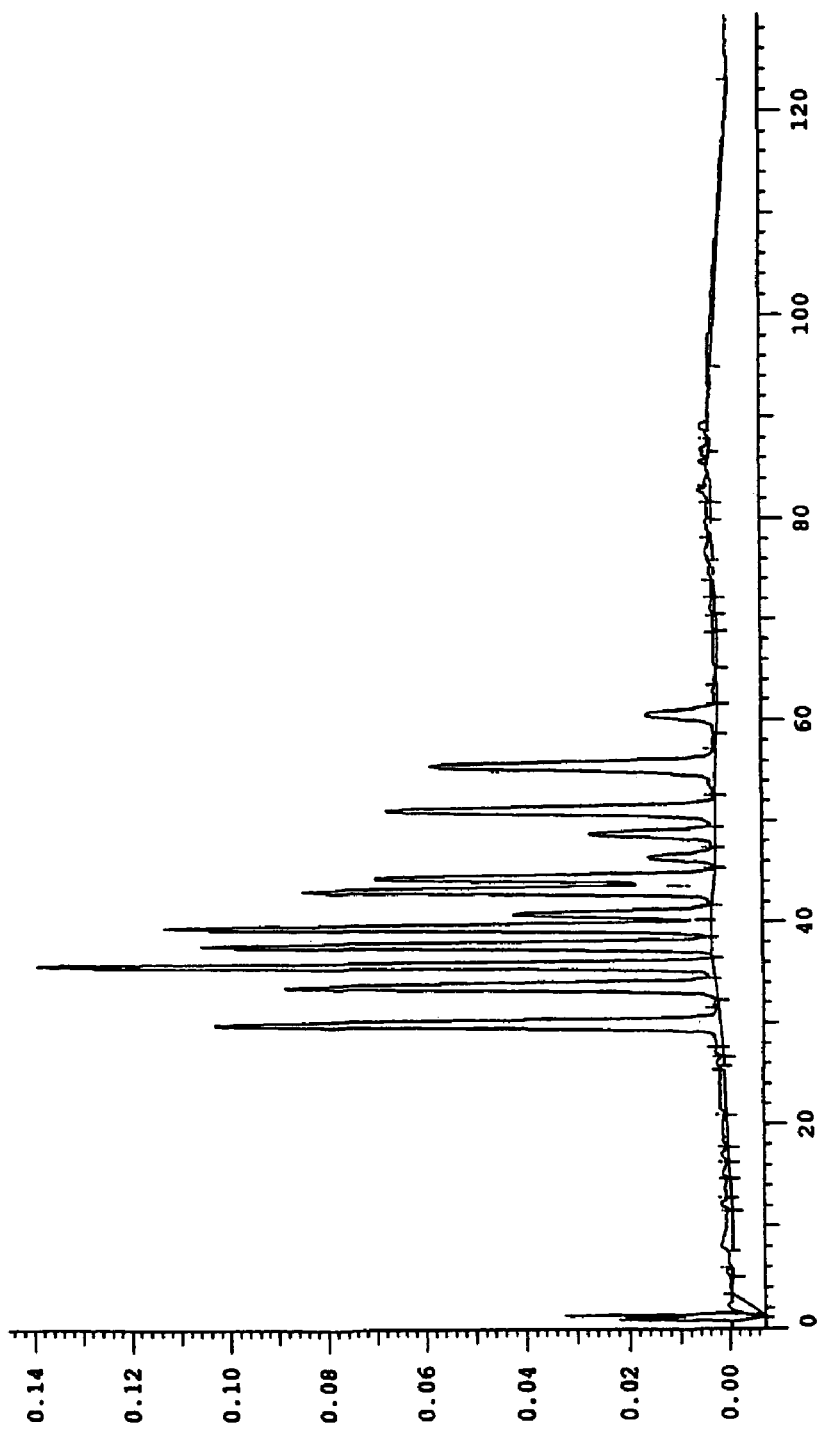
FIG. 2 is an HPLC chromatogram at 510 nm of a phenolic-enriched composition ("fraction 3") prepared from bilberries.
Figure 3:
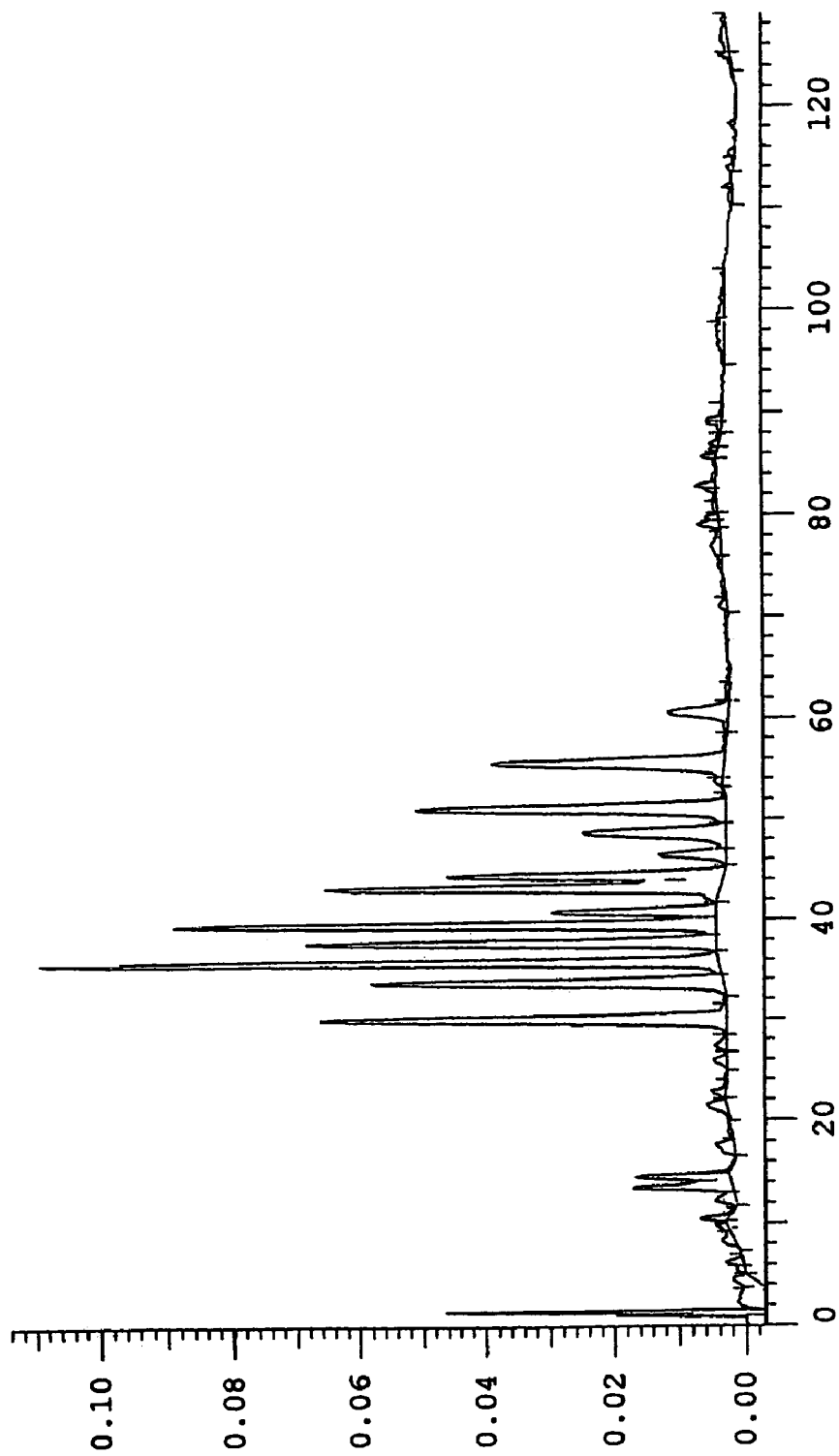
FIG. 3 is an HPLC chromatogram at 280 nm of a phenolic-enriched composition ("fraction 3") prepared from bilberries.

FIGS. 2 and 3 are HPLC chromatograms at 510 nm and 280 nm, respectively, of a phenolic-enriched composition ("fraction 3") prepared from bilberries according to the process of this invention.

Table 1 summarizes the percent of each anthocyanin in a typical anthocyanin-enriched composition ("fraction 3").

TABLE 1

Identification and content of anthocyanins present in a bilberry "fraction 3"

| Name | Elution order | % composition |
| --- | --- | --- |
| Delphinidin-3-O-galactoside | 1 | 3.3 |
| Delphinidin-3-O-glucoside | 2 | 3.9 |
| Cyanidin-3-O-galactoside | 3 | 2.1 |
| Delphinidin-3-O-arabinoside | 4 | 2.6 |
| Cyanidin-3-O-glucoside | 5 | 2.8 |
| Petunidin-3-O-galactoside | 6 | 1.0 |
| Petunidin-3-O-glucoside | 7 | 2.5 |
| Cyanidin-3-O-arabinoside | 8 | 1.7 |
| Peonidin-3-O-galactoside | 9 | 0.3 |
| Petunidin-3-O-arabinoside | 10 | 0.8 |
| Malvidin-3-O-galactoside Peonidin-3-O-glucoside (co-elute) | 11 | 2.1 |
| Malvidin-3-O-glucoside | 12 | 2.5 |
| Peonidin-3-O-arabinose | 13 | 0.1 |
| Malvidin-3-O-arabinose | 14 | 0.6 |
| Total | | 26.3 |

Example 3

Phenolic-Enriched Compositions from Blueberries

To 940 g of dried and ground blueberry (Van Drunen FutureCeuticals; Momence, Ill.) were added 4.0 liters of extraction solvent (1.0% w/v sulfuric acid in 70% ethanol) in a 10 L round bottom flask. The flask was rotated in a constant temperature water bath held at 40° C. for two hours.

The mixture was swirled and filtered through a 150 g bed of Celite 512 under vacuum. The blueberry biomass cake was washed with 500 mL of extraction solvent. The cake was carefully scraped away from the Celite bed, poured into a round bottom flask, and re-extracted following the above-described procedure. A third extraction was then performed. The three crude extracts were combined.

A portion of the combined extracts (2.00 L) was concentrated in vacuo to 175 mL at a water bath temperature of 40° C. The evaporated extract was diluted with deionized water to give 675 mL of crude blueberry extract. The crude extract was loaded without filtration onto a previously conditioned (i.e., washed with acetone) and equilibrated column loaded with 170 mL of brominated polystyrene resin (SP-207). The column was washed with 0.1% acetic acid and with 0.1% HOAc/10% ethanol. The anthocyanins were eluted with 70% ethanol. The product pool was evaporated in vacuo at 60° C. and 50 mbar. Final product assay was by standard spectrophotometric determination of absorbance at 535 nm against a delphinidin chloride standard (102 absorbance units/g/L at 1.0 cm). The purified blueberry composition ("fraction 3") contained 18% total anthocyanins by weight, with an overall recovery of anthocyanins of 95%.

Figure 4:
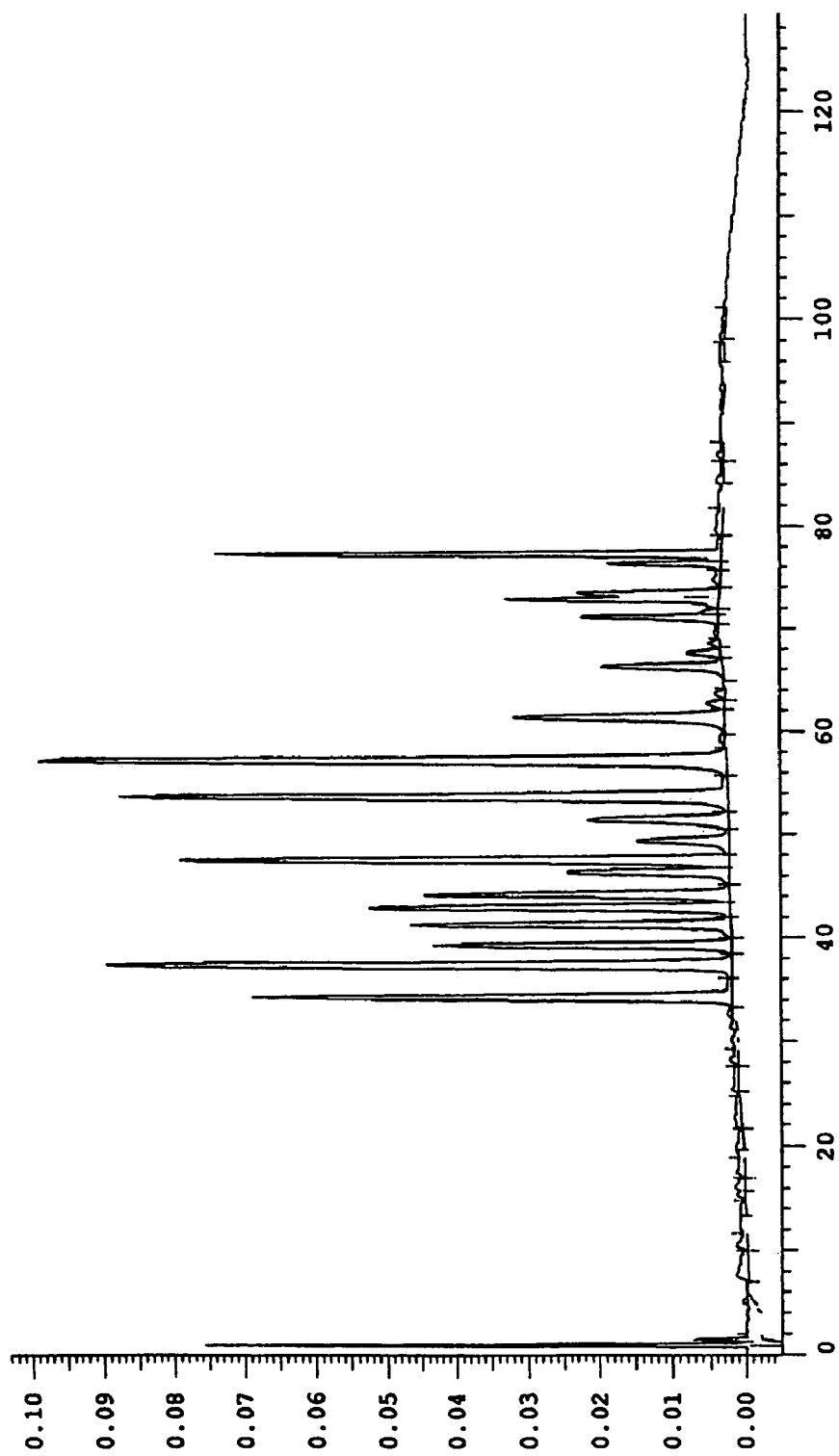
FIG. 4 is an HPLC chromatogram at 510 nm of a phenolic-enriched composition ("fraction 3") prepared from blueberries.
Figure 5:
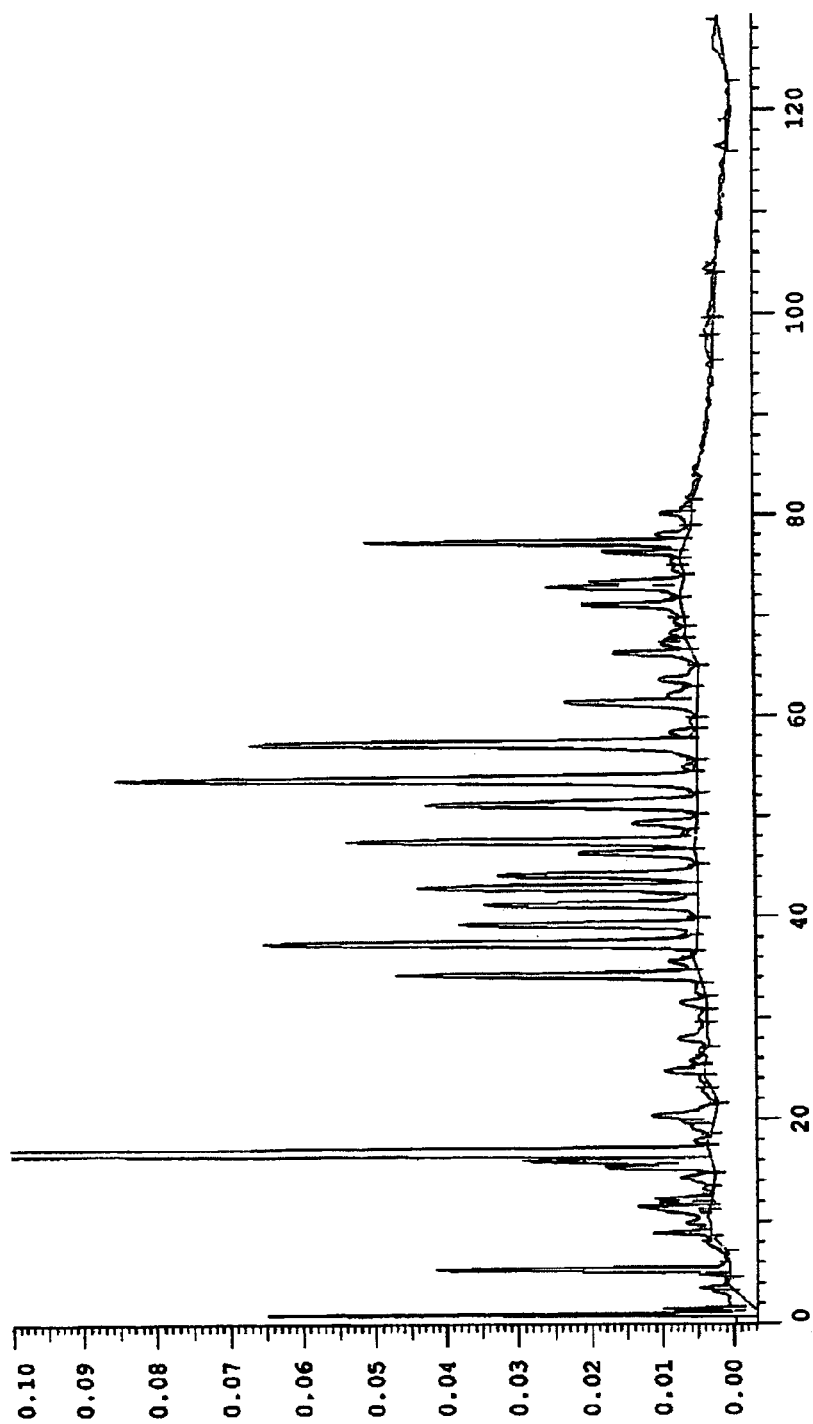
FIG. 5 is an HPLC chromatogram at 280 nm of a phenolic-enriched composition ("fraction 3") prepared from blueberries.

FIGS. 4 and 5 are HPLC chromatograms at 510 nm and 280 nm, respectively, of a phenolic-enriched composition ("fraction 3") prepared from blueberries according to the method of this invention.

Example 4

Higher Purity Phenolic-Enriched Composition from Blueberries

In this example, a portion of a phenolic-enriched composition prepared from blueberries and having 18% total anthocyanins by weight, prepared as described in Example 3, was passed through either a strong or a weak anion exchange resin to remove residual acids in order to increase the purity of the enriched composition.

Approximately 1.0 g of the phenolic-enriched blueberry composition was dissolved in 50 mL of water and passed through a 9 mL column containing either a strong anion exchange resin (Super Q-650 M; TosoHaas; Montgomery, Pa.) or a weak anion exchange resin (DEM-63; Whatman). The column was washed with 30-35 mL of water. In the case of the strong anion exchange resin column, the resin was further washed with 25 mL of 20% ethanol, followed by 40% ethanol. The composition isolated from the strong anion exchange column contained 28.3% total anthocyanins by weight, and the recovery was 88%. The composition isolated from the weak anion exchange column contained 30.6% total anthocyanins by weight, and the recovery was 88%.

Example 5

Phenolic-Enriched Compositions from Bilberry Using Pectinase Treatment

Warm water (548 g) was added to 1024 g of frozen bilberries. The mixture was pureed in a blender and then heated to 40° C. Next, 150 µL of pectinase (Quest Super 7×; Quest International, Norwich, N.Y.) were added for a 30 minute treatment at 40° C. with stirring. Approximately 4 mL of concentrated sulfuric acid were added to the slurry to achieve an acid concentration of 0.5% (w/w). The mixture was then heated to 45° C. and extracted for 15 minutes with very slow stirring. Dicalite (164 g) was added to the extracted mixture, which was then filtered over a 26 g Dicalite bed. The resulting cake was washed three times with 400 mL of warm 0.1% aqueous sulfuric acid. This extract was filtered through a 25 µm pressure filter. All of the filtered extract (2.4 L) was loaded onto a 170 mL SP-207 column. After loading, the column was washed with 0.1% aqueous acetic acid and eluted with 70% aqueous ethanol to provide "fraction 3". "Fraction 3" was evaporated to dryness and then placed on a lyophilizer for 48 hours. The final product was assayed for total anthocyanins by standard spectrophotometric determination of absorbance at 535 nm. The phenolic-enriched composition contained 40% total anthocyanins by weight. The overall recovery of anthocyanins was approximately 79%.

Example 6

Enriched Compositions from Elderberry Biomass Powder

Approximately 190 g of dried elderberry biomass powder (BI Nutraceuticals, Long Beach, Calif.) assayed at 1.88% anthocyanins and 5.31% phenolic compounds were added to 1000 g of warm water. The solution was mixed thoroughly and transferred to a hot water bath at 45° C. To the solution was added 190 µL of pectinase (Super 7X, Quest), and then the mixture was allowed to sit for 30 minutes. The mixture was acidified to a pH of 2.5 using 2.5 mL of concentrated $H_2SO_4$ and gently mixed for ten minutes. To this acidified mixture was added 164 g of Celite, and then the acidified mixture was filtered over a 26 g Celite bed. The filter cake was washed three times with 400 mL of acidified warm water, for a total of 1200 mL. The filtrate was then filtered through a 25 µm pressure filter to provide an elderberry extract.

The elderberry extract was loaded onto 170 mL of SP-207 (Mitsubishi Chemical) brominated polystyrene column at a rate of 2.3 mL/min (1.3 mL/min/cm$^2$). The eluent collected off the column during loading was collected as "fraction 1." After loading, the column was washed with 3 column volumes (3×170 mL) of 0.006% aqueous sulfuric acid. The eluent from this wash was collected as "fraction 2." The column was then eluted with 8-10 column volumes of 70% aqueous ethanol, which were collected as "fraction 3." The column was then washed with 3 column volumes of 90% aqueous ethanol, which were collected as "fraction 4." The column was re-equilibrated with 8 column volumes of 0.006% aqueous sulfuric acid. Fractions 3 and 4 were evaporated to dryness and then lyophilized until dry. Several of the fractions isolated during elution from the brominated polystyrene resin were analyzed for anthocyanins and phenolic compounds as described in Examples 7 and 8. Table 2 summarizes the column data.

TABLE 2

Analysis and recovery of anthocyanins and polyphenols in elderberry fractions

| | Anthocyanins | | Polyphenols | |
|---|---|---|---|---|
| | % Purity | % Recovery | % Purity | % Recovery |
| "fraction 1" | 0.05 | 2.79 | 1.37 | 24.4 |
| "fraction 2" | 1.68 | 7.79 | 5.57 | 8.5 |

TABLE 2-continued

Analysis and recovery of anthocyanins
and polyphenols in elderberry fractions

| | Anthocyanins | | Polyphenols | |
|---|---|---|---|---|
| | % Purity | % Recovery | % Purity | % Recovery |
| "fraction 3" | 18.7 | 99.4 | 42.8 | 74.7 |
| "fraction 4" | 0.67 | 0.49 | 2.61 | 0.6 |

FIGS. 6-13 show the HPLC chromatograms of the filtered elderberry extract and of certain fractions isolated during column purification. The HPLC conditions used are those described in Example 9.

Figure 6:
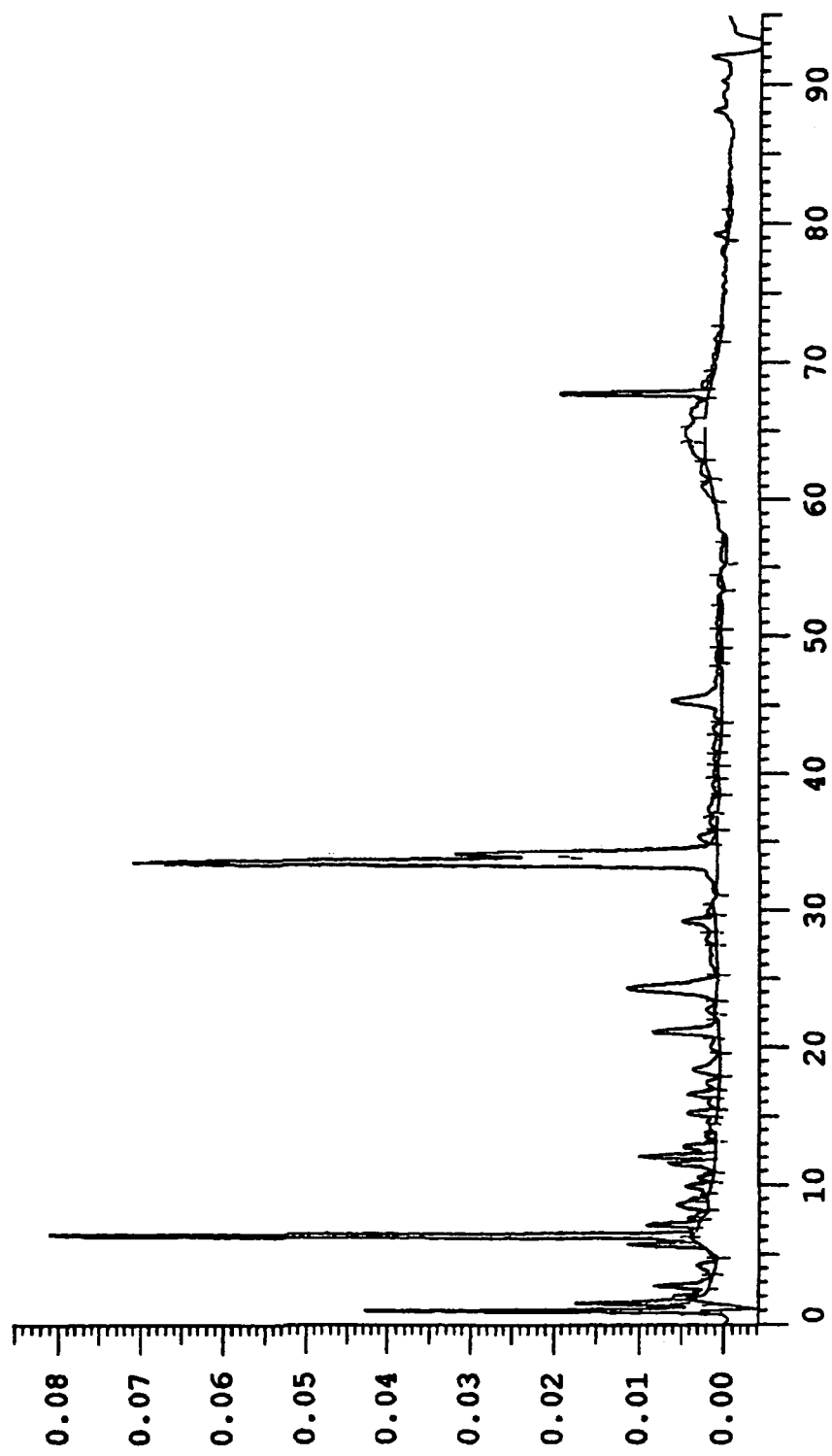
FIG. 6 is an HPLC chromatogram at 280 nm of a filtered elderberry extract.
Figure 7:
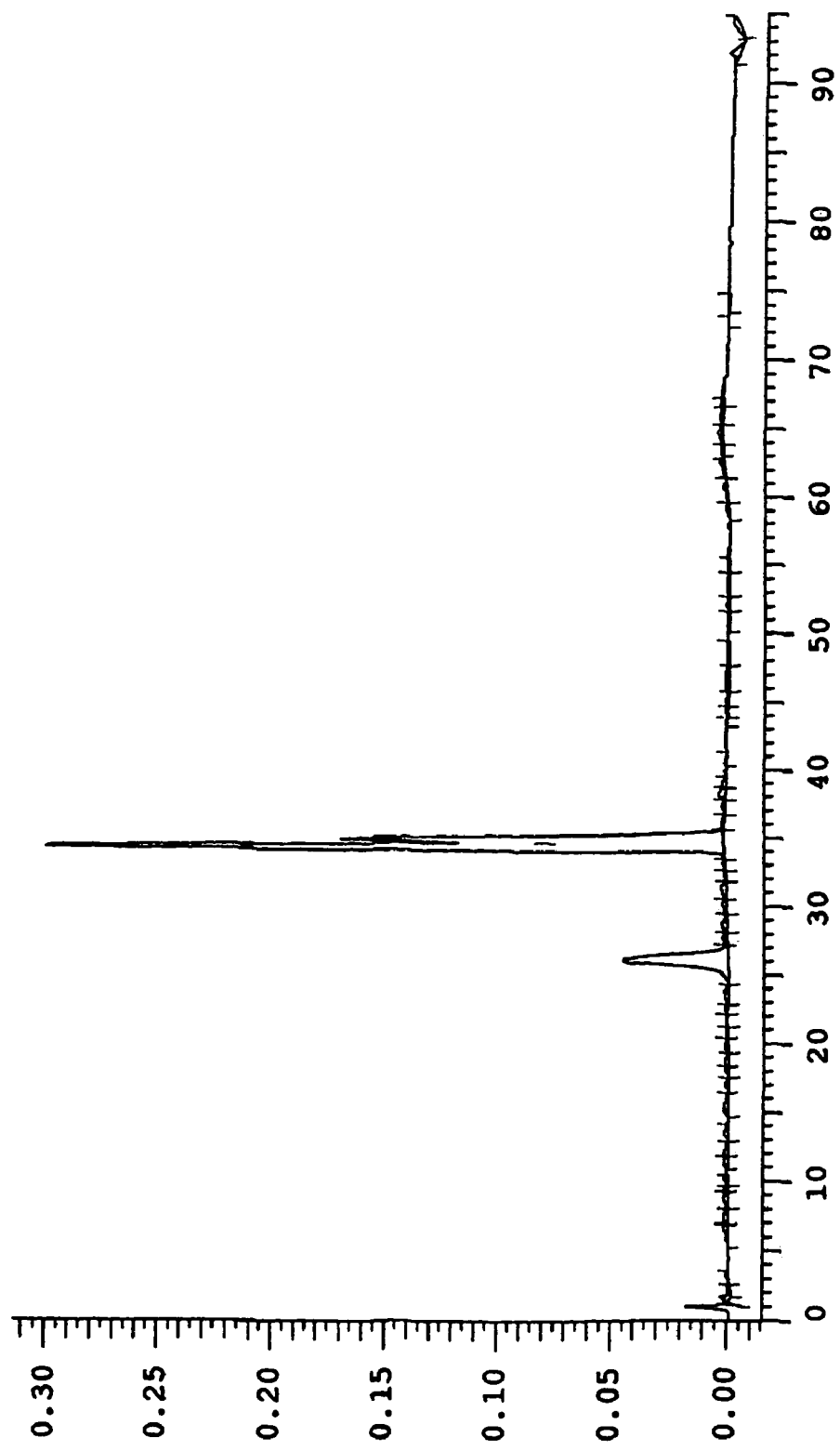
FIG. 7 is an HPLC chromatogram at 510 nm of a filtered elderberry extract.

FIGS. 6 and 7 show the HPLC chromatograms at 280 nm and 510 nm, respectively, of the filtered elderberry extract.

Figure 8:
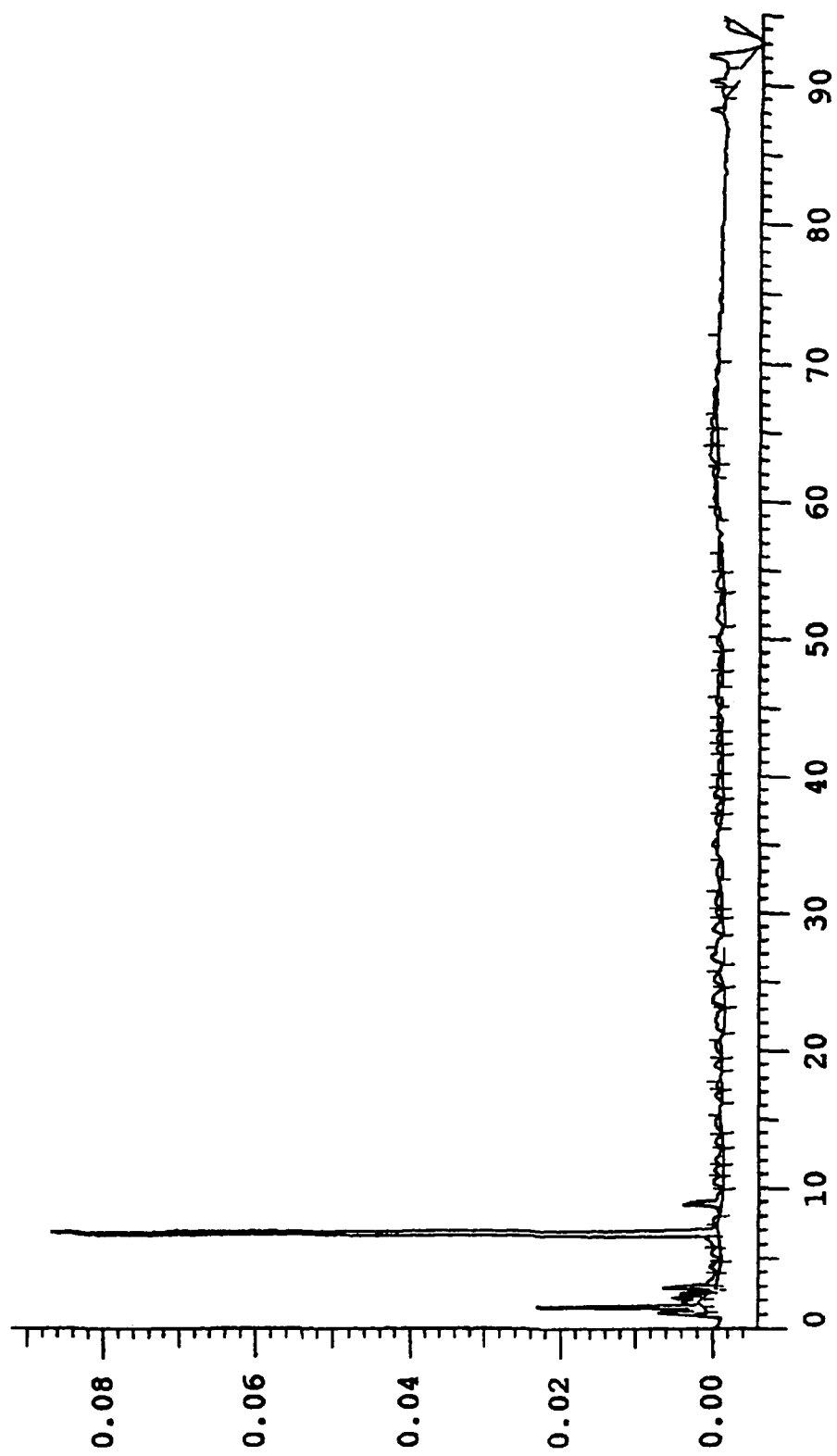
FIG. 8 is an HPLC chromatogram at 280 nm of a first fraction eluted during column loading of a filtered elderberry extract.
Figure 9:
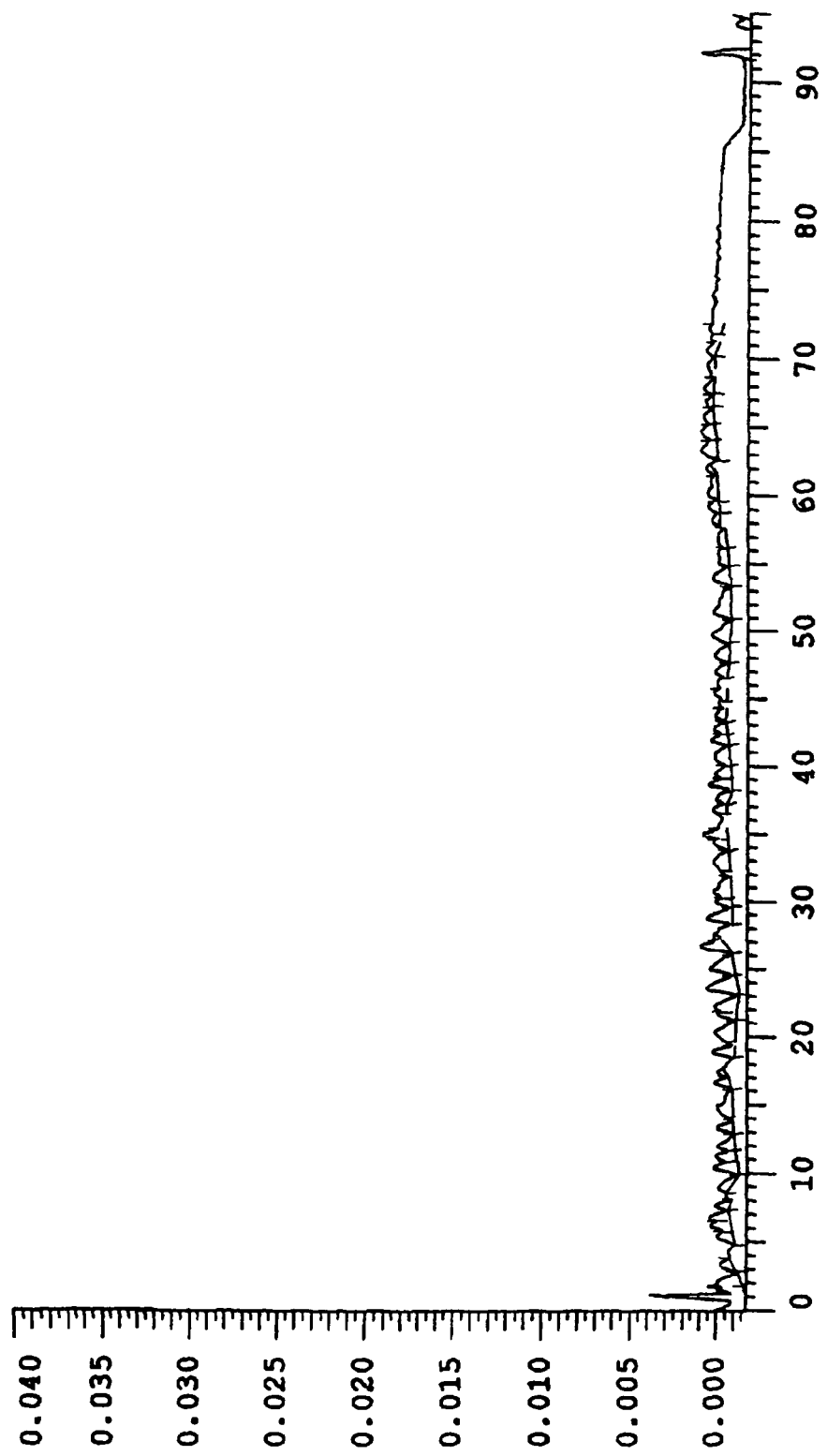
FIG. 9 is an HPLC chromatogram at 510 nm of a first fraction eluted during column loading of a filtered elderberry extract.

FIGS. 8 and 9 show the HPLC chromatograms at 280 nm and 510 nm, respectively, of "fraction 1" collected during column loading of the filtered elderberry extract onto the brominated polystyrene resin.

Figure 10:
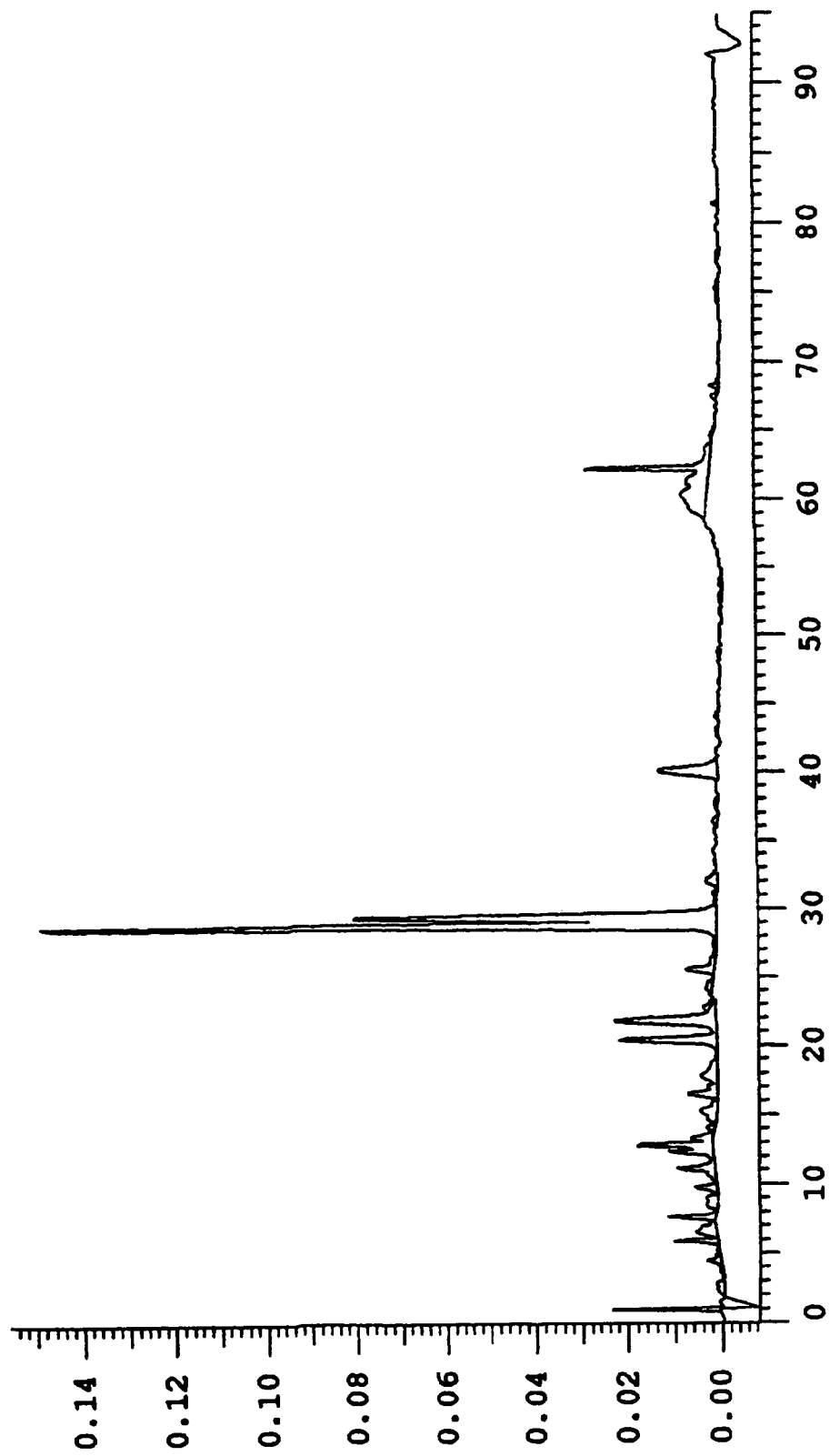
FIG. 10 is an HPLC chromatogram at 280 nm of a third fraction eluted with 70% ethanol during column purification of an elderberry extract on a brominated polystyrene resin.
Figure 11:
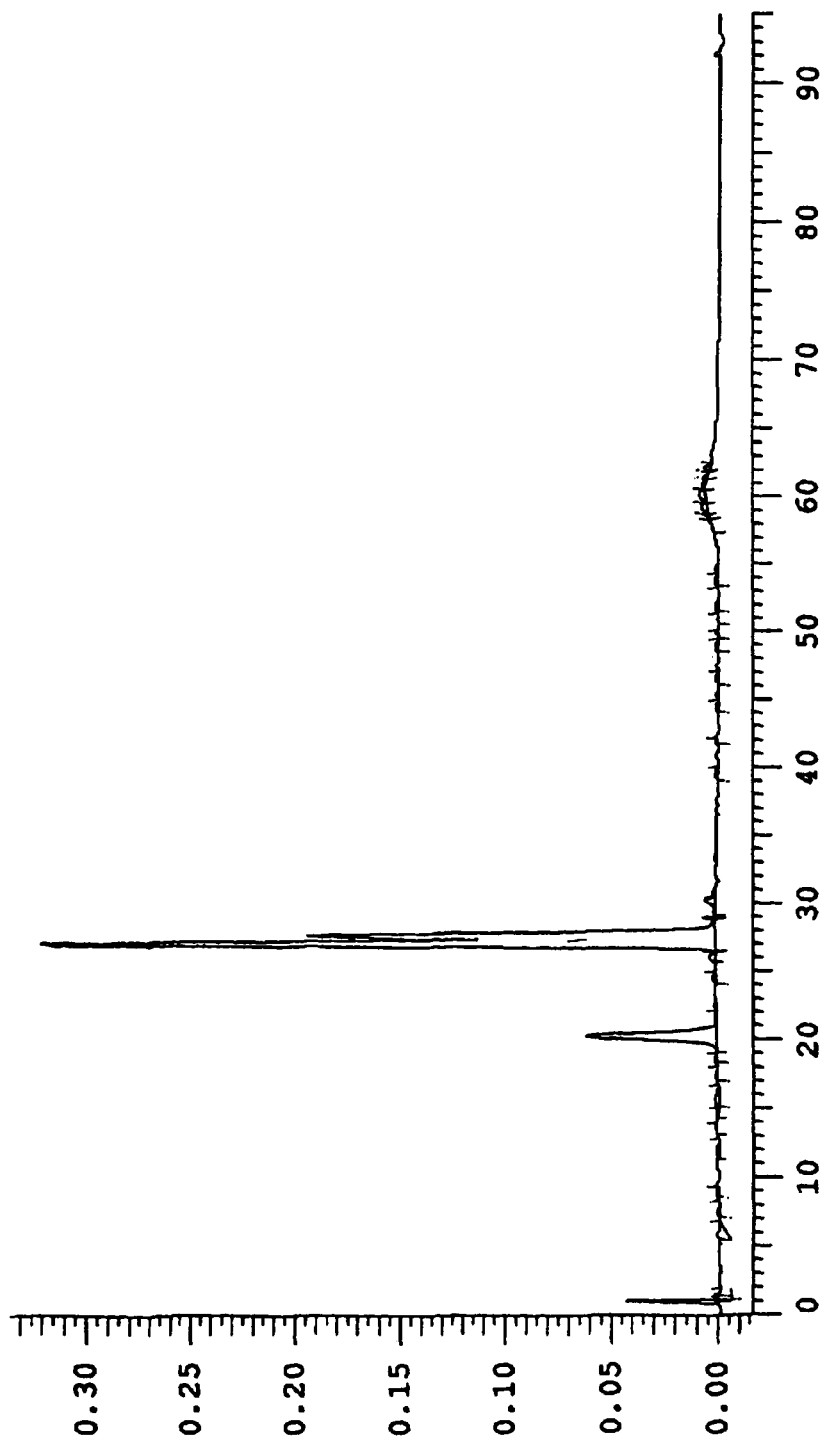
FIG. 11 is an HPLC chromatogram at 510 nm of a third fraction eluted with 70% ethanol during column purification of an elderberry extract on a brominated polystyrene resin.

FIGS. 10 and 11 show the HPLC chromatograms at 280 nm and 510 nm, respectively, of "fraction 3" collected during column elution of the filtered elderberry extract using 70% ethanol from the brominated polystyrene resin.

FIGS. 12 and 13 show the HPLC chromatograms at 280 nm and 510 nm, respectively, of "fraction 4" collected during column elution of the filtered elderberry extract using 90% ethanol from the brominated polystyrene resin.

The phenolic-enriched compositions of this invention comprise the compounds showing peaks in the region between 60 and 75 minutes in the standard HPLC chromatograms substantially as shown in FIGS. 10-13.

Example 7

Quantitative Determination of Anthocyanins

This method is used to determine the total anthocyanins in various biomass samples and dried purified phenolic-enriched compositions by UV-VIS spectrophotometry, using an external standard. Each sample tested (e.g., a concentrated phenolic-enriched composition, dried biomass, or fresh/frozen biomass) requires a different preparation procedure as described below.

Phenolic-enriched compositions—Accurately weigh 75-100 mg of the purified phenolic-enriched composition into a 100 mL volumetric flask and dilute to volume with 2% HCl/MeOH. Mix well and dilute 0.40-1.6 mL of this sample to 10.0 mL with 2% HCl/MeOH.

Dry Biomass—Into a coffee grinder place an amount of dry biomass sufficient to cover the blades of the grinder. Grind for about 1 minute or until finely ground. Alternatively use a mortar and pestle to finely grind the raw material. Accurately weigh about 50-100 mg of finely ground biomass into a 100 mL volumetric flask and then add about 80 mL of 2% HCl/MeOH and cap. Place the flask into a 50° C. oil bath or forced air oven for 30-60 minutes, shake gently for 30 seconds, and sonicate for 5 minutes. Allow the solution to cool to room temperature. Add 2% HCl/MeOH to the mark and mix. Filter a portion of the sample through a 0.45 µm PTFE syringe filter into a vial. Dilute 1.0 mL of the filtrate to 10.0 mL with 2% HCl/MeOH. The dilution factor would be 10 mL/1 mL or 10.

Frozen/Fresh Biomass—Weigh 400.0 g frozen/fresh biomass into a 1000 mL polypropylene beaker. Add 400 g of near boiling water into the beaker. Puree using a mechanical blender (Waring or other). Using a wide-bore polyethylene dropper, remove a representative 0.5-1.5 g sample and transfer into a tared 100 mL volumetric flask. Add 80 mL of 2% HCl/MeOH and cap. Place the flask into a 50° C. oil bath or forced air oven for 60-120 minutes, shake gently for 30 seconds and then sonicate for 5 minutes. Allow the solution to cool to room temperature. Add 2% HCl/MeOH to the mark and mix. Filter a portion through a 0.45 µm PTFE syringe filter into a vial. The dilution factor would be the total weight of the biomass and water divided by the weight of the biomass [e.g., (400 g+400 g)/400 g=2].

Loss on Drying—The calculation to obtain the total anthocyanins content in the above samples requires the determination of the moisture content, or % LOD (loss on drying), of the material. To determine the % LOD, transfer and distribute evenly 0.5-3.0 g of sample into an accurately weighed aluminum weigh pan, and record the weight to the nearest 0.1 mg. Place the sample in an oven at 105° C. ±3° C. for 2 hours (do not exceed 2 hrs 15 min). After the sample has cooled to room temperature (a dessicator may be used), weigh the sample and record the weight to the nearest 0.1 mg. The % LOD is determined to the nearest 0.1% using Equation 1:

$$\% \; LOD = 1 - \frac{W_D - W_P}{W_{SP} - W_P} \times 100 \qquad \text{Eq. 1}$$

where % LOD=percentage loss on drying; $W_D$=dry weight of the pan and sample (g); $W_P$=weight of the pan (g); and $W_{SP}$=initial weight of the pan and sample (g).

Assay Procedures—The UV/VIS spectrophotometer is set to read in photometry mode with the visible lamp on. The instrument is zeroed at 535 nm using 2% HCl/MeOH in a 1 cm pathlength glass, quartz, or disposable polystyrene cuvette. The absorbance of the prepared sample is measured at 535 nm in the same or matched 1 cm cuvettes.

Calculations—The concentration of total anthocyanins is calculated as shown in Equation 2:

$$C_{ANTHOS} = \frac{ABS_{SAMP} \times DF}{E_S} \qquad \text{Eq. 2}$$

where $C_{ANTHOS}$=concentration of the total anthocyanins in the sample (mg/mL); $ABS_{SAMP}$=absorbance of the sample at 535 nm; DF=dilution factor, as described below; and $E_S$=absorptivity (absorbance of a 1 mg/mL solution at 535 m in 2% HCl/MeOH using a 1 cm cuvette) of the appropriate external standard, either cyanidin chloride (101.1; for cherry, cranberry, elderberry, and plum) or delphinidin chloride (102.0; for bilberry and blueberry). The dilution factor (DF) for a dry biomass is 1, and the dilution factor for fresh/frozen biomass is the total weight of the biomass and water divided by the weight of the biomass (e.g., (400 g+400 g)/400 g). The dilution factor for a purified extract is the final dilution volume divided by the volume of the extract solution (e.g., 10 mL/0.40 mL).

The percent total anthocyanins is calculated as shown in Equation 3:

$$\% \ Anthos = \frac{C_{ANTHOS} \times \text{Volume} \times 100}{W_S \times S_{LOD}} \qquad \text{Eq. 3}$$

where % ANTHOS=percentage of total anthocyanins in the sample; $C_{ANTHOS}$=concentration of total anthocyanins (mg/mL); Volume=initial volume of the sample preparation (usually 100 mL); $W_S$=weight of the biomass or phenolic-enriched compositions used in the preparation (usually 50-100 mg for dry biomass, 500-1500 mg for fresh/frozen biomass, or 75-100 mg for purified extracts); and $S_{LOD}$= [(100-% LOD)/100] for dry or fresh biomass or purified extract (for fresh or frozen biomass this factor does not apply).

Example 8

Quantitative Determination of Total Polyphenols

This method is used to quantitatively determine the total polyphenols in various biomass samples and dried purified enriched compositions by UV-VIS spectrophotometry, using gallic acid as the external standard.

The procedure requires a 20% $Na_2CO_3$ solution and 2% HCl/MeOH. To prepare the $Na_2CO_3$ solution, weigh approximately 100 g of $Na_2CO_3$ into a 500 mL volumetric flask containing about 350 mL deionized water. Sonicate for 10 minutes; shake to mix. Dilute to volume using deionized water and agitate until homogeneous. To prepare the 2% HCl/MeOH, transfer about 350 mL of methanol into a 500 mL volumetric flask. Pipet into the flask 10.0 mL of HCl. Dilute to volume using methanol and mix until homogeneous.

To prepare the gallic acid stock standard, accurately weigh 100 mg of gallic acid (Sigma; St. Louis, Mo.) into a 100 mL volumetric flask. Add 70 mL of deionized water and sonicate for 5 minutes until dissolved. Dilute to volume using deionized water, cap, and mix until homogeneous.

Each sample tested (e.g., phenolic-enriched composition, dry biomass, or fresh/frozen biomass) requires a different preparation procedure and was prepared as described in Example 7.

Loss on Drying—The calculation to obtain the total polyphenols content in the above samples requires the determination of the moisture content, or % LOD, of the material. To determine the % LOD, transfer and distribute evenly 0.5-3.0 g of sample into an accurately weighed aluminum weigh pan, and record the weight to the nearest 0.1 mg. Place the sample in an oven at 105° C. ±3° C. for 2 hours (do not exceed 2 hrs 15 min). After the sample has cooled to room temperature (a dessicator may be used), weigh the sample and record the weight to the nearest 0.1 mg. The % LOD is determined to the nearest 0.1% using Equation 1 above.

Colorimetric Development Procedures—A clean 100 mL volumetric flask is set aside to serve as the reagent blank. Two 100 mL volumetric flasks are labeled "high" standard and "low" standard. Using the gallic acid stock solution, pipet 800 µL into the "high" standard flask and 200 µL into the "low" standard flask. For dry biomass samples, pipet 20 mL of the filtered solution into a 100 mL volumetric flask. For fresh/frozen biomass samples, pipet 10 mL of the filtered solution into a 100 mL volumetric flask. For purified samples, pipet 0.80-2.0 mL into a 100 mL volumetric flask. The following are added to each of the volumetric flasks (including the reagent blank) prepared above:
1. Add sufficient deionized water to each flask to bring the total volume to approximately 65 mL.
2. Pipet 5.0 mL of the FC Phenol Reagent (Sigma) into each flask, agitate gently.
3. Pipet 15±2 mL of the 20% $Na_2CO_3$ solution into each flask.
4. Mix the solutions in each flask with gentle swirling, dilute to volume with deionized water, cap, and invert.
5. Allow the solutions to develop for at least three but not more than four hours.
6. Filter 10 mL aliquots of samples requiring filtration through 0.45 µm PVDF syringe filters into suitable containers.

Assay Procedure—The UV-VIS spectrophotometer is set to read in photometry mode with the visible lamp on. The analysis is carried out in 1 cm pathlength glass, quartz, or disposable polystyrene cuvettes. The instrument is zeroed at 760 nm using the reagent blank. The absorbance of each solution is measured at 760 nm in the same or matched 1 cm cuvettes.

Calculations—To calculate the concentration of total polyphenols the absorptivity of gallic acid must first be determined. This value is obtained as described in Equation 4:

$$E_R = \frac{A_R \times D_R}{C_R \times (1 - E_{LOD})} \qquad \text{Eq. 4}$$

where $E_R$=absorptivity of the reference standard (gallic acid) at 760 nm in absorbance units/g/L; $A_R$=absorbance of the reference standard solution; $C_R$=concentration of gallic acid in the stock standard solution, $D_R$=dilution factor for the gallic acid standard (125 for "high" standard or 500 for "low" standard); and $E_{LOD}$=loss on drying of the gallic acid solids as a percent.

The absorptivities for the "high" and "low" standards are averaged for use in Equation 5 below. The concentration of total polyphenols in the color development sample preparations is calculated as shown in Equation 5:

$$C_P = \frac{A_S \times D_{FC}}{E_R} \qquad \text{Eq. 5}$$

where $C_P$=concentration of total polyphenols in the FC sample preparation (mg/mL); $A_S$=absorbance of the FC sample preparation; $D_{FC}$=sample dilution factor, where DF is typically 5 for dry biomass, 10 for fresh/frozen biomass, and 50-125 for purified enriched composition; and $E_R$=average absorptivity of the gallic acid standards.

The percent total polyphenols is calculated as shown in Equation 6:

$$\% \ P = \frac{C_P \times V_S \times D_S \times 100}{W_S \times S_{LOD}} \qquad \text{Eq. 6}$$

where % P=percentage of total polyphenols in the sample; $C_P$=the concentration of total polyphenols (mg/mL); $V_s$=volume of original sample preparation (usually 100 mL); $W_S$=weight of the biomass or purified composition used in the original sample preparation (usually 50-100 mg for dry biomass, 500-1500 mg for fresh/frozen biomass, and 75-100 mg for purified extracts); $D_S$=original sample dilution factor, where $D_S$ is 1 for dry biomass, 2 for fresh/frozen biomass, or 1 for purified extract; and $S_{LOD}$=[(100-% LOD)/100] for biomass or purified extracts. For fresh or frozen biomass this factor does not apply.

Example 9

HPLC Qualitative Assay

This method is used to qualify compounds in various biomasses and purified enriched compositions by high performance liquid chromatography (HPLC). Each type of sample requires a different preparation procedure as described below.

Dry Biomass: The dry biomass, if not already powdered, is ground through a 1 mm screen using the Wiley mill. Using an appropriately sized extraction thimble and a soxhlet extraction apparatus, weigh out approximately 12 g of powdered biomass into the thimble and extract using 200 mL of methanol. Extract through at least 20 cycles or until the extraction solvent is clear. Transfer the extract quantitatively to a 250 mL volumetric flask using methanol, dilute to volume and mix. Filter the extract through a 0.45 µm PTFE syringe filter into an HPLC vial.

Frozen/Fresh Biomass: Weigh 400 g frozen/fresh biomass into a 1000 mL polypropylene beaker. Add 400 g of near boiling water into the beaker. Puree using a mechanical blender (Waring or other). Using a wide-bore polyethylene dropper, remove a representative 0.5-1.5 g sample and transfer into a tared 100 mL volumetric flask. Add 80 mL MeOH, cap, and heat at 50° C. for 30 minutes. Allow the solution to cool to room temperature, adjust to volume with methanol, and then sonicate until homogeneous. Filter a portion through a 0.45 µm PTFE syringe filter into an HPLC vial.

Purified Enriched Composition: Accurately weigh 50-100 mg of the enriched composition into a glass scintillation vial and add 10.0 mL of 50% MeOH/$H_2O$. Sonicate for 5 minutes. Filter through a 0.45 µm PTFE syringe filter into an HPLC vial.

The HPLC is set up as required. In one embodiment of this invention, the aqueous mobile phase was prepared by mixing 5 mL of trifluoroacetic acid (TFA) into 1000 mL of high purity, Type 1 water. A 20 µL sample was injected at ambient temperature. A 280 nm wavelength was used for detection, the flow rate was 1.0 mL/min, and the run time was 105 minutes. A Zorbax column was packed with 5 µm SBC-18 in a 150×4.6 mm ID column. In this embodiment, the mobile phase was set up as follows: channel A: 100% acetonitrile; channel B: 0.5% TFA in $H_2O$; and channel C: 100% methanol. Table 3 summarizes the HPLC gradient for this embodiment of the invention.

If available, standard preparations of compounds known to exist in the sample may be prepared at concentrations of approximately 1 mg/mL. These standard preparations can be used to determine the approximate retention times and thus identify those compounds in the sample chromatograms. As this method is used for qualification purposes only, no calculations are required.

TABLE 3

HPLC gradient for qualitative analysis

| Time (min) | % A | % B | % C |
|---|---|---|---|
| 0.0 | 0 | 95 | 5 |
| 7.0 | 5 | 90 | 5 |
| 32.1 | 8 | 84 | 8 |
| 33.0 | 9 | 83 | 8 |
| 63.0 | 14 | 78 | 8 |
| 91.5 | 27 | 65 | 8 |
| 99.0 | 72 | 20 | 8 |
| 104.0 | 72 | 20 | 8 |
| 104.1 | 0 | 95 | 5 |
| 112.0 | 0 | 95 | 5 |

Example 10

Quantitative HPLC Method for Determination of Percent Proanthocyanidins

This HPLC method is used to determine the amount of proanthocyanidins in various fractions and enriched compositions. Each type of sample requires a different preparation and is prepared as described in Example 9. The method uses a 5 µm Zorbax column packed with Stablebond SBC-18 in a 150×4.6 mm column. The flow rate was 1.5 mL/min, the detector was set at 280 nm, the injection volume was 10 µL, and the run time was 24 min. The mobile phase was: channel A=100% acetonitrile; channel B=0.1% trifluoroacetic acid in water; channel C=100% methanol. The gradient employed is provided in Table 4. The proanthocyanidins typically eluted as a group of broad peaks in the HPLC chromatogram at elution times between 11-22 minutes.

TABLE 4

HPLC gradient for % analysis for proanthocyanidins

| Time (min.) | % A | % B | % C |
|---|---|---|---|
| 0 | 14 | 78 | 8 |
| 9 | 14 | 78 | 8 |
| 17 | 34 | 58 | 8 |
| 22 | 34 | 58 | 8 |
| 22.1 | 14 | 78 | 8 |
| 26 | 14 | 78 | 8 |

Figure 14:
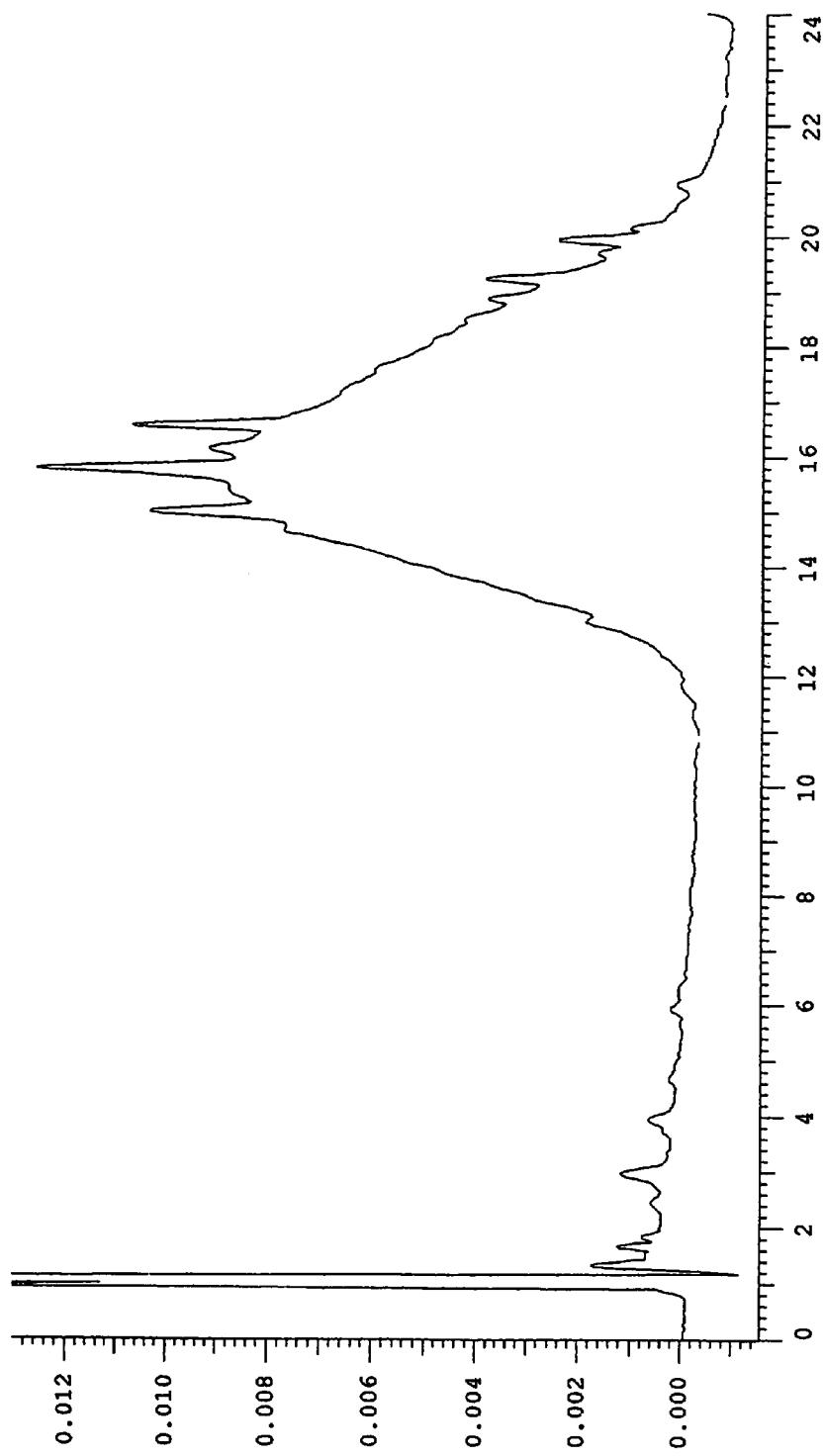
FIG. 14 is an HPLC chromatogram using an alternate HPLC method of the proanthocyanidins standard prepared as described in Example 10.

To quantitate the proanthocyanidins, a previously prepared in-house proanthocyanidin standard is utilized with a purity greater than 90%. A sample of this is prepared at 5.5 mg/mL in 70% ethanol and analyzed using the HPLC method described in this Example. The chromatogram for this standard includes a large, broad peak in the 11-22 minute retention time range (as seen in FIG. 14) which is due to the proanthocyanidins. Manually integrate the entire 11-22 minute peak. The peak area response factor for the standard is then determined by dividing the entire 11-22 minute peak area by the product of the standard's concentration and its purity as shown in Equation 7:

$$RF = \frac{PA}{C_{std} \times P_{std}} \qquad \text{Eq. 7}$$

where RF=peak area response factor for the standard (area units/mg/mL); PA=peak area of the proanthocyanidins in the standard; $C_{std}$=concentration of the standard solution in mg/mL; and $P_{std}$=standard purity as a percent (usually 0.90).

The percent proanthocyanidins in a sample can be determined using the sample preparation and HPLC analysis method described above. The total peak area in the 11-22 minute retention time range is determined for the sample in question. Before any calculation can be made, however, the peak areas of non-proanthocyanidin compounds in the proanathocyanidin retention time range must be subtracted from the overall total peak area. Non-proanthocyanidin compounds often appear as sharp peaks co-eluting with or on top of the broad proanthocyanidins' peak, and their UV spectrum by diode array is often different from the bulk of the proanthocyanidin peak. To determine the peak area of non-cyanidin proanthocyanidin peaks, manually integrate these peaks, total their peak area and subtract this area from the total 11-22 minute peak area. Once the net area of the proanthocyanidins' peak in the sample has been determined, divide this value by the peak area response factor for the in-house standard to obtain the concentration of proanthocyanidins in the sample as shown in Equation 8:

$$C_{proanthos} = \frac{PA_{samp} \times DF}{RF} \quad \text{Eq. 8}$$

where $C_{proanthos}$=concentration of total proanthocyanidins in the sample (mg/mL); $PA_{samp}$=corrected total peak area for the sample; DF=dilution factor (1 for dry biomass, 2 for fresh/frozen biomass, and 1 for an enriched composition); and RF=peak area response factor calculated using Equation 7.

The percent total proanthocyanidins is calculated as shown in Equation 9:

$$\% \text{ Proanthocyanidins} = \frac{C_{proanthos} \times V \times 100}{W_s} \quad \text{Eq. 9}$$

where % Proanthocyanidins=percent of total proanthocyanidins in the sample; $C_{proanthos}$=concentration of total proanthocyanidins (mg/mL); V=volume of the sample preparation (usually 250 mL for dry biomass, 100 mL for fresh/frozen biomass, or 10 mL for enriched compositions); and $W_s$=weight of the biomass or enriched composition used in the sample preparation (usually 12,000 mg for dry biomass, 500-1500 mg for fresh/frozen biomass, or 50-100 mg for enriched compositions).

Example 11

Partitioning Polar and Non-Polar Proanthocyanidins Directly from a Filtered Elderberry Extract In this example, a filtered elderberry extract was prepared and, rather than being purified on a brominated polystyrene resin, was instead loaded directly onto a vacuum liquid chromatography (VLC) column to partition polar proanthocyanidins and non-polar proanthocyanidins directly from a filtered extract according to the method illustrated in FIG. 15.

Figure 16:
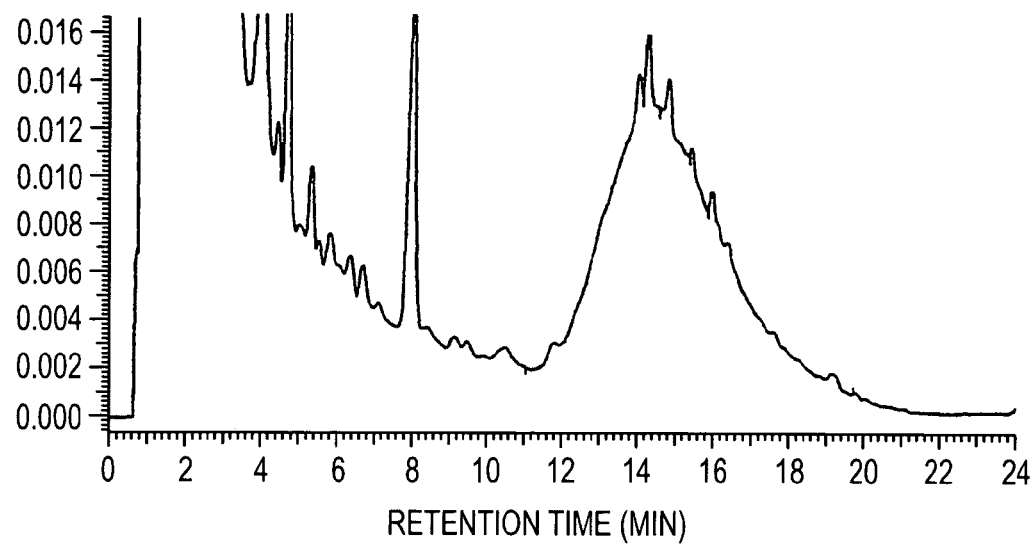
FIG. 16 is an HPLC chromatogram at 280 nm of a filtered elderberry extract.
Figure 17:
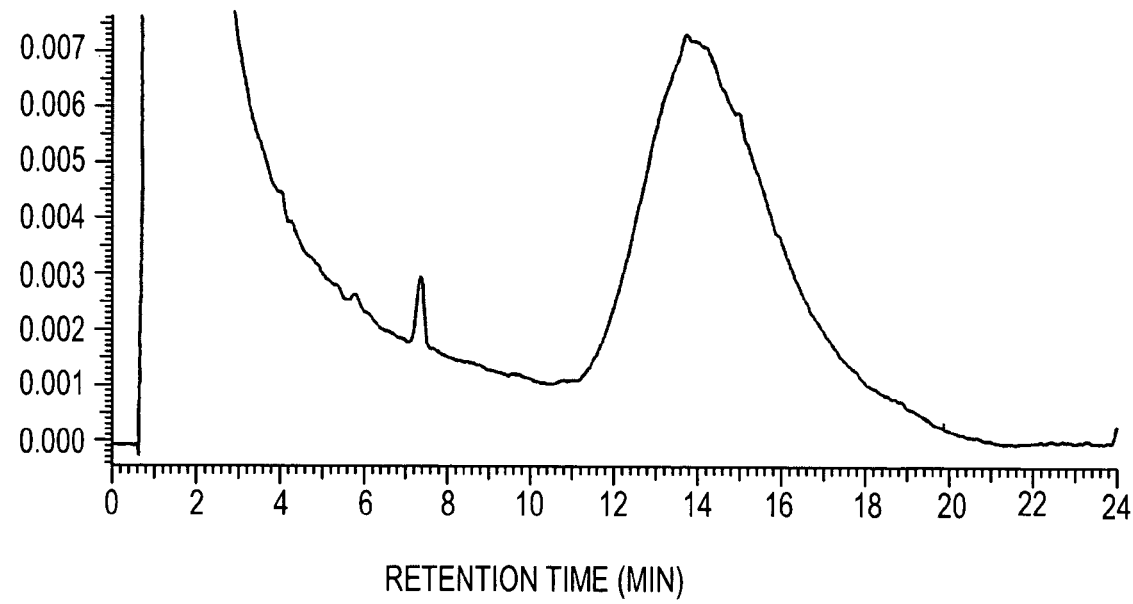
FIG. 17 is an HPLC chromatogram at 280 nm of an elderberry polar proanthocyanidin composition ("fraction 5") isolated from the combined flow-through and wash fractions from a VLC C-18 column.
Figure 18:
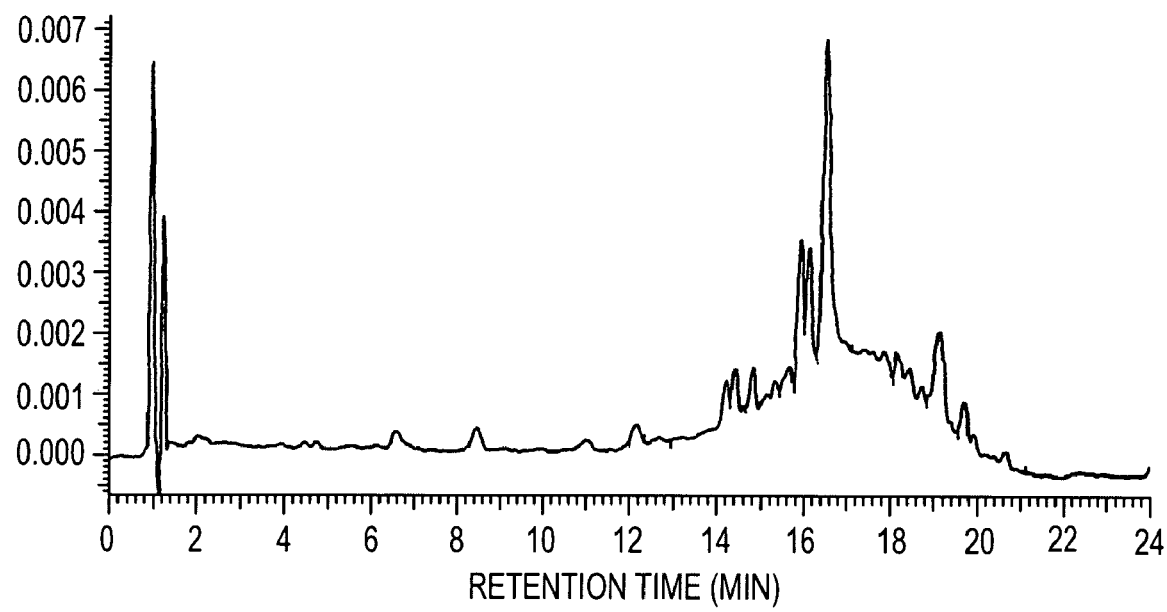
FIG. 18 is an HPLC chromatogram at 280 nm of an elderberry non-polar proanthocyanidin composition ("fraction 6") isolated in the 60% methanol eluent from a VLC C-18 column.

A 50 mL C-18 VLC column was prepared by filtering a 50 mL slurry of Bakerbond 40 µm flash chromatography C-18 media in methanol through a 60 mL fritted glass filter. The column was conditioned by washing with methanol and then with water. A 300 mL portion of the filtered elderberry extract, containing 12.0 g of solids, 74 mg of anthocyanins and about 780 mg of proanthocyanidins, was loaded onto the column. An HPLC chromatogram of the filtered extract using the HPLC method described in Example 10 is shown in FIG. 16. The flow-through eluent (about 300 mL) and a 100 mL wash (0.1% trifluoroacetic acid (TFA)) were combined to provide the polar proanthocyanidin "fraction 5." An HPLC chromatogram at 280 nm of "fraction 5" is shown in FIG. 17. The column was then eluted with 100 mL each of 30, 40, 50, 60, 70, and 100% methanol containing 0.1% TFA. An HPLC chromatogram at 280 nm of the non-polar proanthocyanidin "fraction 6" isolated in the 60% methanol eluent is shown in FIG. 18. The fractions were assayed for anthocyanins and proanthocyanidins by the methods described in Examples 7 and 10. Table 5 summarizes the results for this experiment.

TABLE 5

Partitioning of Elderberry

| Elution Fraction | Anthocyanins (mg) | Proanthocyanidins (mg) | % Proanthocyanidin purity |
|---|---|---|---|
| Flow-Through + Wash | 54 | 554 | 4.7 |
| 30% MeOH | 11 | 10 | 1.1 |
| 40% MeOH | 3 | 20 | 12 |
| 50% MeOH | 1 | 92 | 92 |
| 60% MeOH | 0.2 | 46 | 92 |
| 70% MeOH | 0.1 | 41 | 100 |
| 100% MeOH | N/A | 21 | |

The results indicate that 71% (558 mg) of the proanthocyanidins in the filtered extract were collected during the loading and wash. These compounds were the more polar proanthocyanidins. The non-polar proanthocyanidins eluted when the methanol concentration was increased to at least 40%. The purity of the proanthocyanidins eluting in the 50-70% methanol fractions was high due to the fact that the majority of the solids contained in the filtered elderberry extract eluted in the loading eluent, water wash, and 30% methanol wash.

Example 12

Partitioning Elderberry Proanthocyanidins by VLC Followed by Purification by Gel Permeation Chromatography or Semi-Preparative HPLC A phenolic-enriched composition was prepared from elderberry dried biomass (Martin Bauer; Germany) by collecting the 70% ethanol fraction ("fraction 3") during elution from a brominated polystyrene resin using the procedure as described in Example 6. A portion (2.00 g) of this phenolic-enriched composition was dissolved in 50 mL of water and loaded onto a 15 mL C-18 VLC column prepared with Bakerbond 40 µm C-18 media. The flow-through eluent and the 25 mL water wash were combined and freeze-dried, yielding 733 mg of the polar proanthocyanidins fraction ("fraction 5"). The column was then washed with 25 mL of 50% methanol. The non-polar proanthocyanidins ("fraction 6") were eluted with 25 mL of 70% methanol. The methanol in this fraction was removed and the resulting water suspension was freeze-dried, yielding 192 mg of the non-polar proanthocyanidin fraction ("fraction 6"), which by HPLC assay was 100% proanthocyanidins. This fraction had little if any color, suggesting that the oligomeric proanthocyanidins chains in this fraction do not contain cationic anthocyanin units.

The polar proanthocyanidins fraction ("fraction 5") was further purified by semi-preparative HPLC to remove residual anthocyanins and other more polar impurities. The conditions for the semi-preparative HPLC purification of these solids are described below.

The semi-preparative HPLC method used a 2.5×10 cm Waters PrepPak cartridge filled with 6 μm, 60 Angstrom, Nova-Pak HR C-18 media (Waters; Milford, Mass.). The mobile phase was: channel A=100% acetonitrile; channel B=0.1% trifluoroacetic acid; channel C=100% methanol. The gradient employed in this embodiment was as provided in Table 6. The flow rate was 30 mL/min, the detector was set at 280 nm, and the injection volume was typically 3-5 mL of a solution containing 50-125 mg of solids. The run time was 30 minutes. The proanthocyanidins were collected in a broad peak that eluted between 13-20 minutes.

TABLE 6

HPLC gradient for Elderberry proanthocyanidin purification

| Time (min) | % A | % B | % C |
|---|---|---|---|
| 0.0 | 11 | 81 | 8 |
| 11.0 | 11 | 81 | 8 |
| 19.0 | 34 | 58 | 8 |
| 24.0 | 34 | 58 | 8 |
| 25.0 | 82 | 10 | 8 |
| 30.0 | 82 | 10 | 8 |
| 30.1 | 11 | 81 | 8 |

Figure 19:
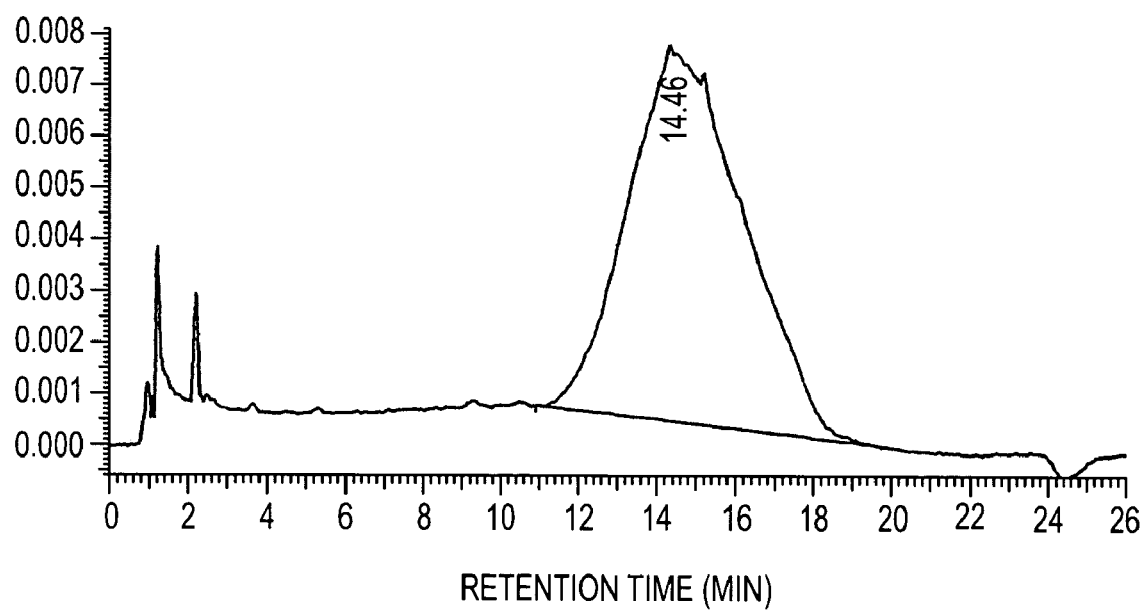
FIG. 19 is an HPLC chromatogram at 280 nm of an elderberry polar proanthocyanidin composition ("fraction 7") isolated after semi-preparative HPLC purification.
Figure 20:
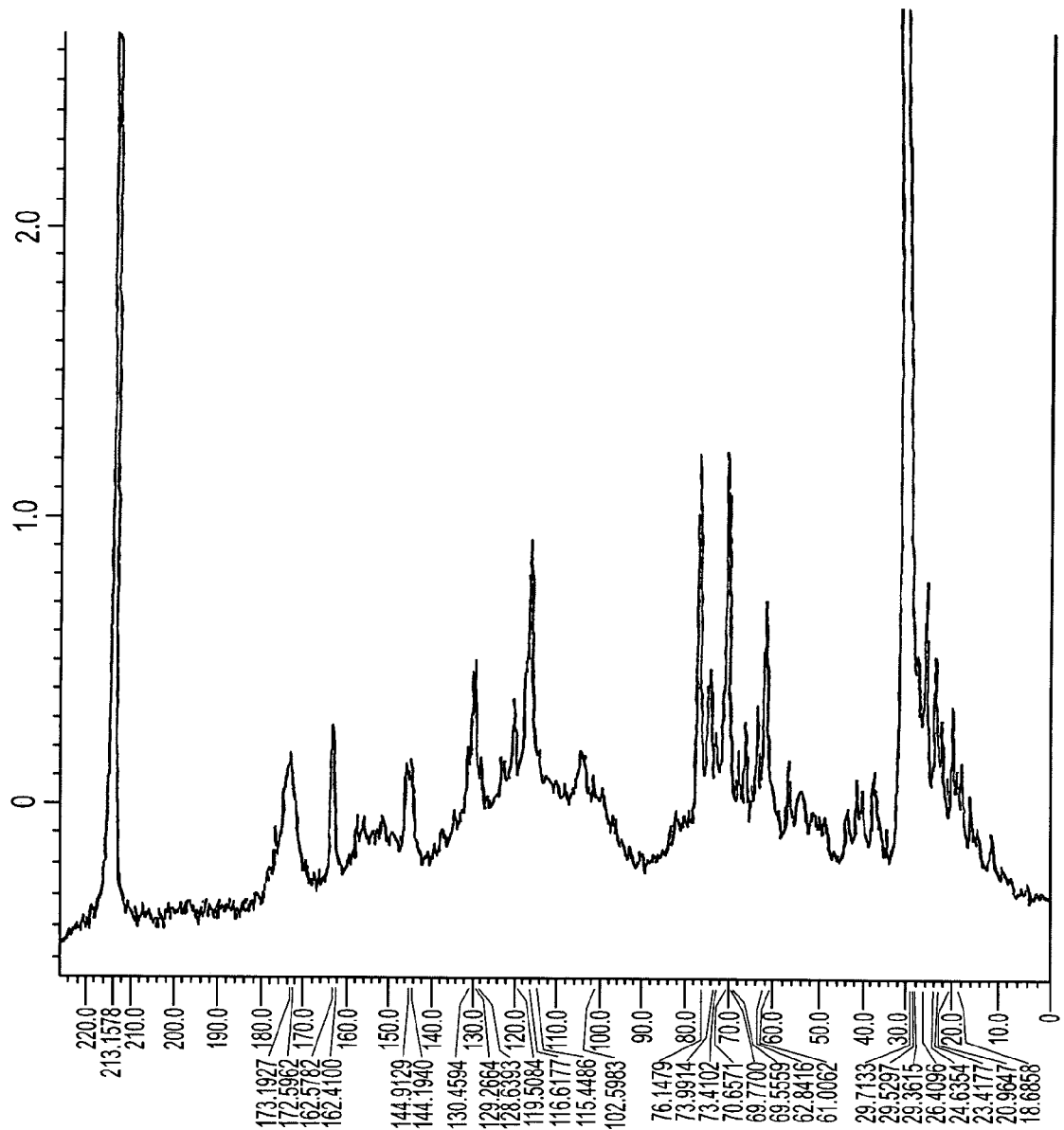
FIG. 20 is a $^{13}$C NMR spectrum of an elderberry polar proanthocyanidin composition ("fraction 7") after purification by semi-preparative HPLC.

About 600 mg of the polar proanthocyanidins fraction ("fraction 5") were dissolved in 25 mL of water. Approximately 3 mL (75 mg) were injected in each of eight runs. The proanthocyanidin peaks eluting between about 12-18 minutes in each run were collected, pooled, and evaporated on a rotary evaporator, and the residual aqueous solution freeze-dried. Approximately 100 mg of purified polar elderberry proanthocyanidins ("fraction 7") were obtained from 600 mg of the polar proanthocyanidin solids ("fraction 5") after VLC separation. An HPLC chromatogram at 280 nm for the VLC-isolated polar proanthocyanidins after semi-preparative HPLC purification is shown in FIG. 19. The polar front, comprising sugars, amino acids, anthocyanins, organic acids, and small flavonoid compounds, was removed by the semi-preparative HPLC purification, as evidenced by the absence of these peaks in FIG. 19. A $^{13}$C NMR spectrum of the purified polar proanthocyanidins ("fraction 7") is shown in FIG. 20.

Figure 25:
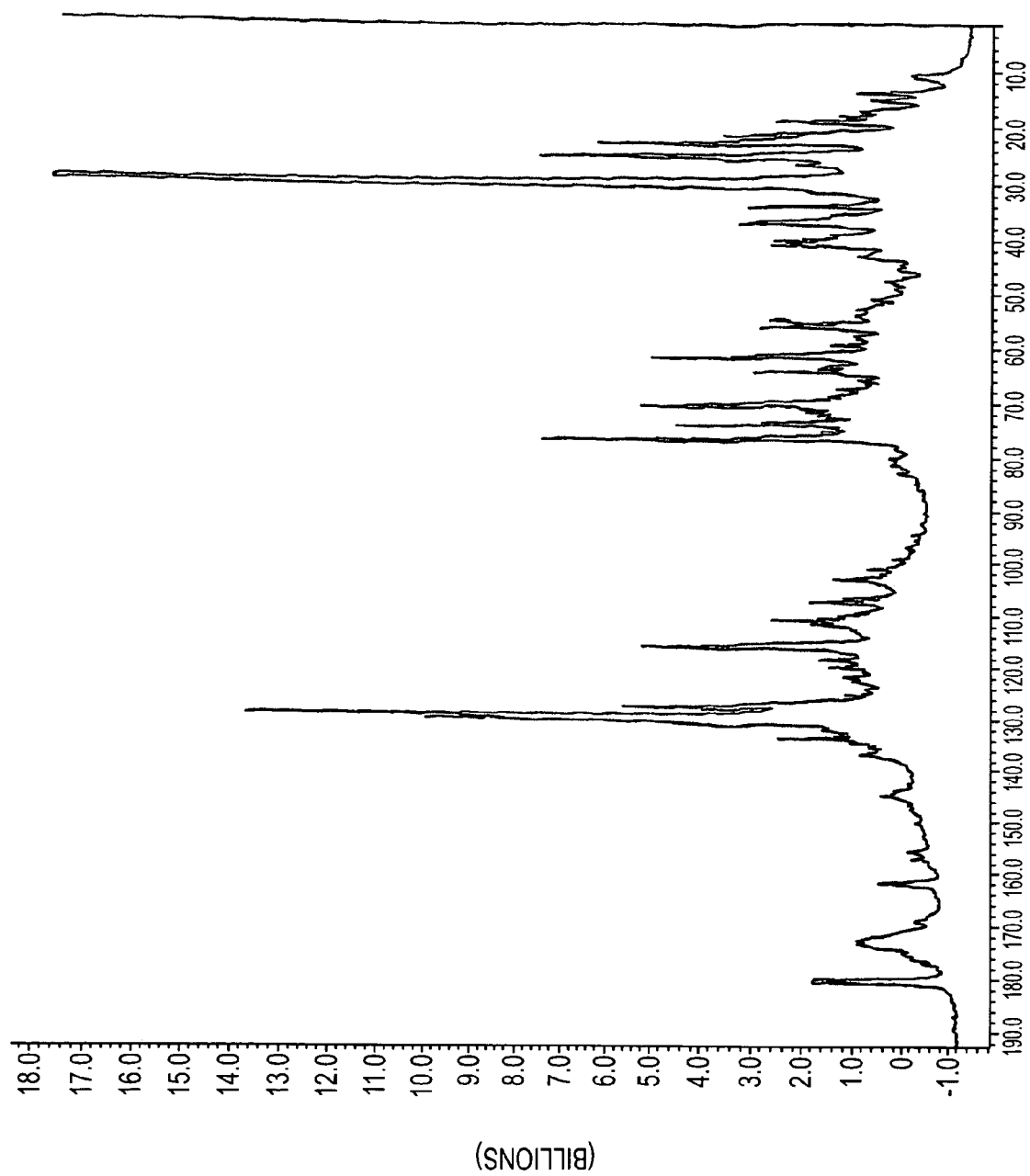
FIG. 25 is a $^{13}$C NMR spectrum of an elderberry non-polar proanthocyanidin composition ("fraction 8") after purification on a Sephadex LH-20 column.
Figure 33:
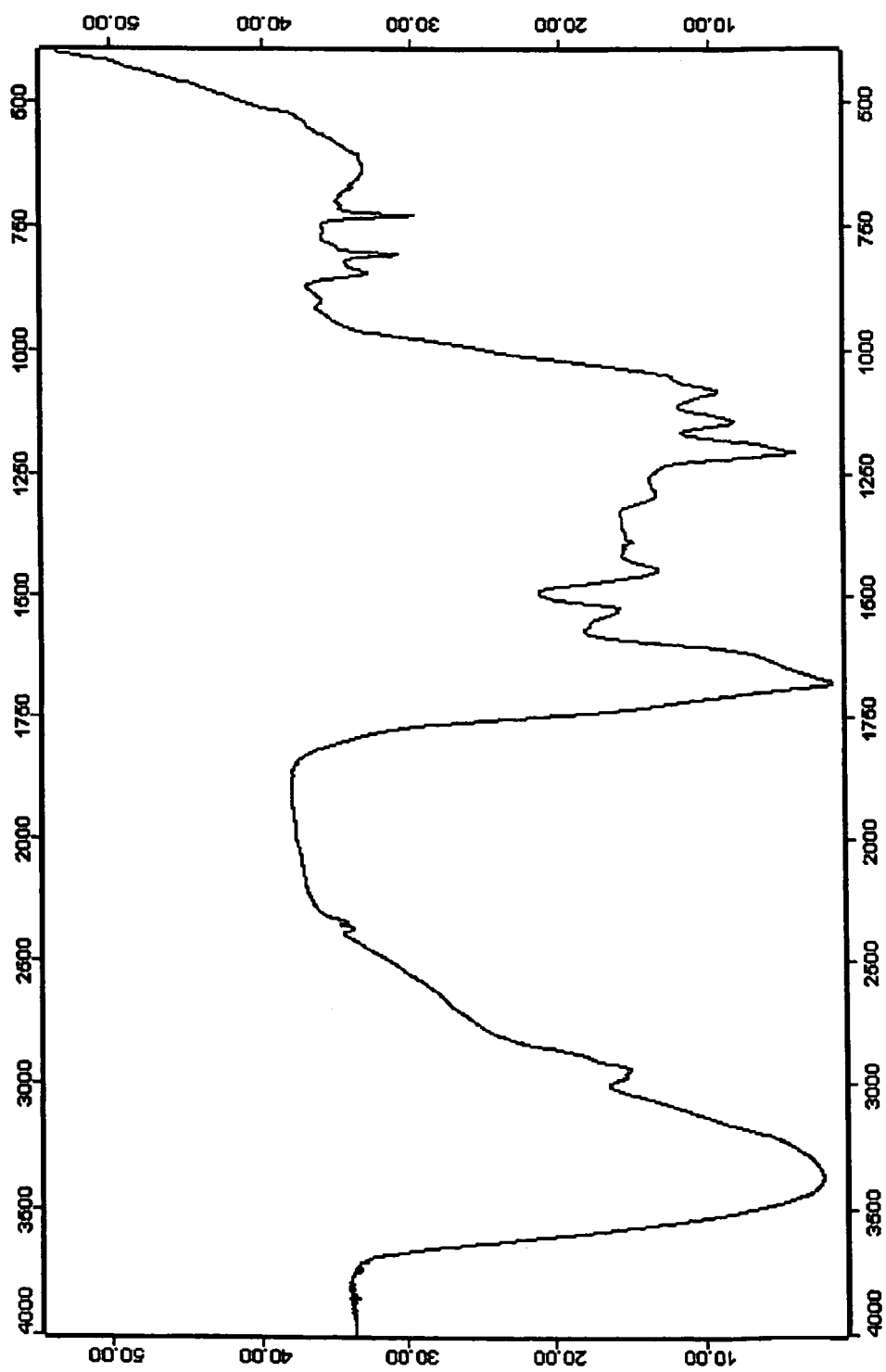
FIG. 33 is an IR spectrum of a purified elderberry polar proanthocyanidin composition ("fraction 7").
Figure 34:
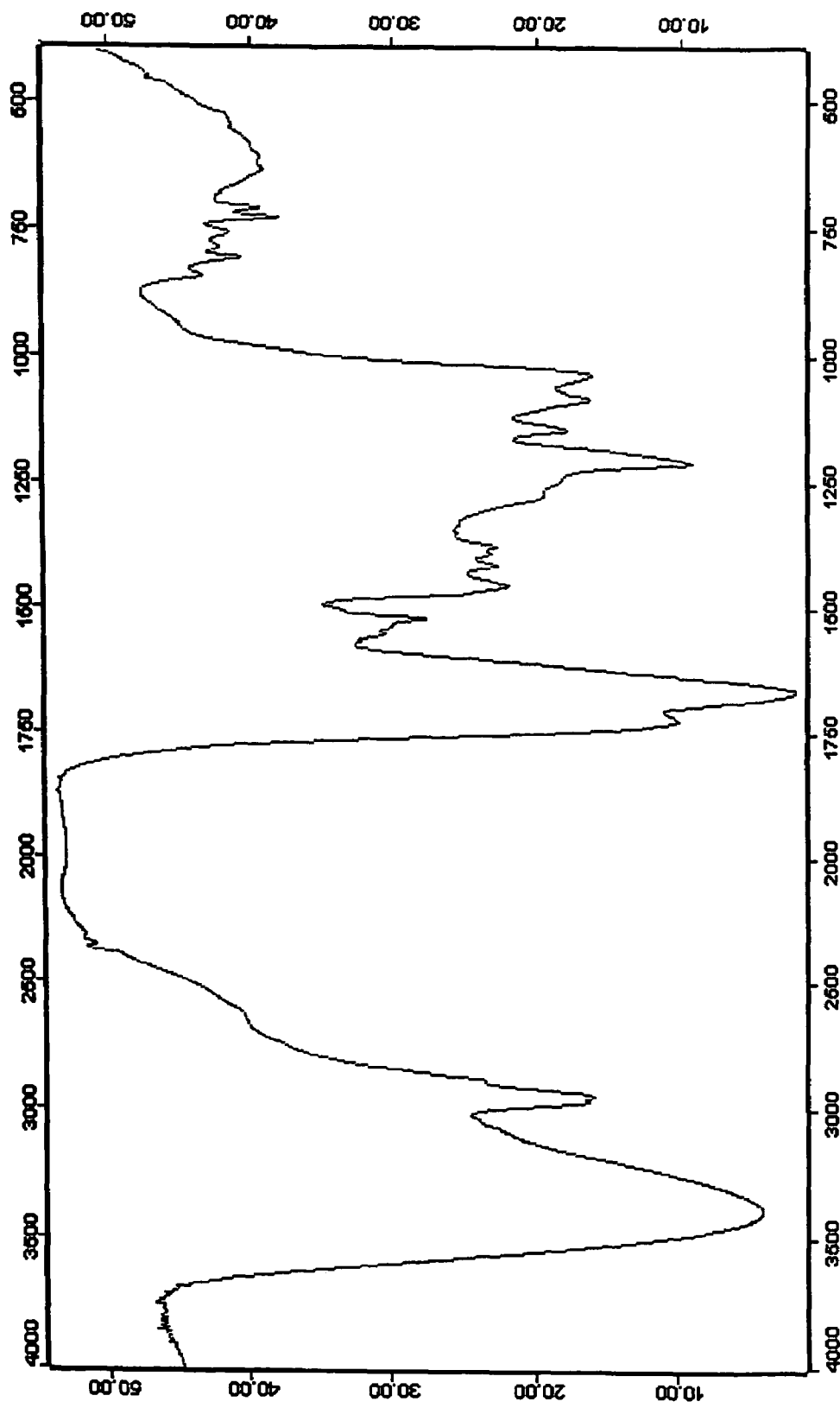
FIG. 34 is an IR spectrum of a purified elderberry non-polar proanthocyanidin composition ("fraction 8").
Figure 35:
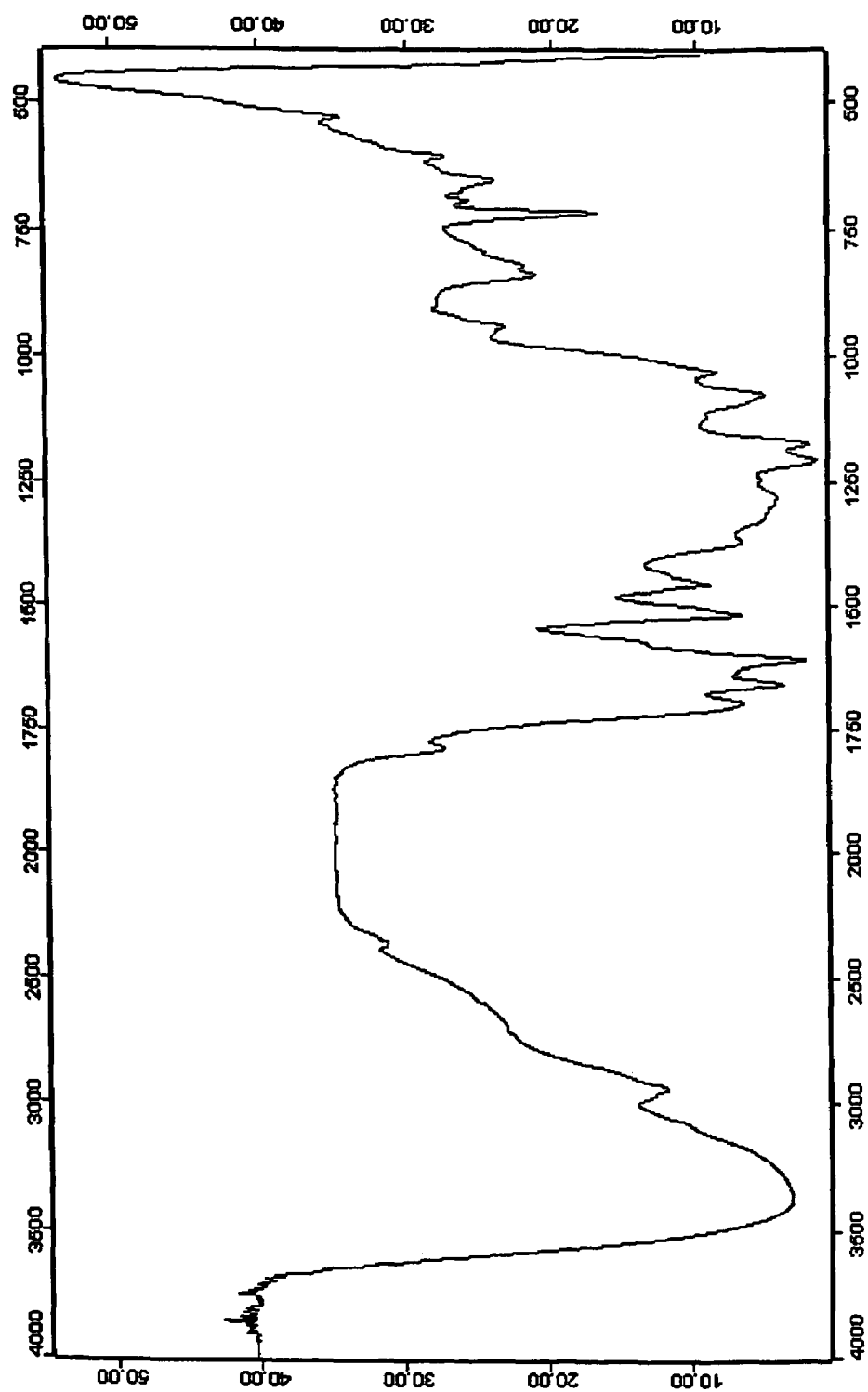
FIG. 35 is an IR spectrum of a purified cranberry non-polar proanthocyanidin composition ("fraction 8").
Figure 36:
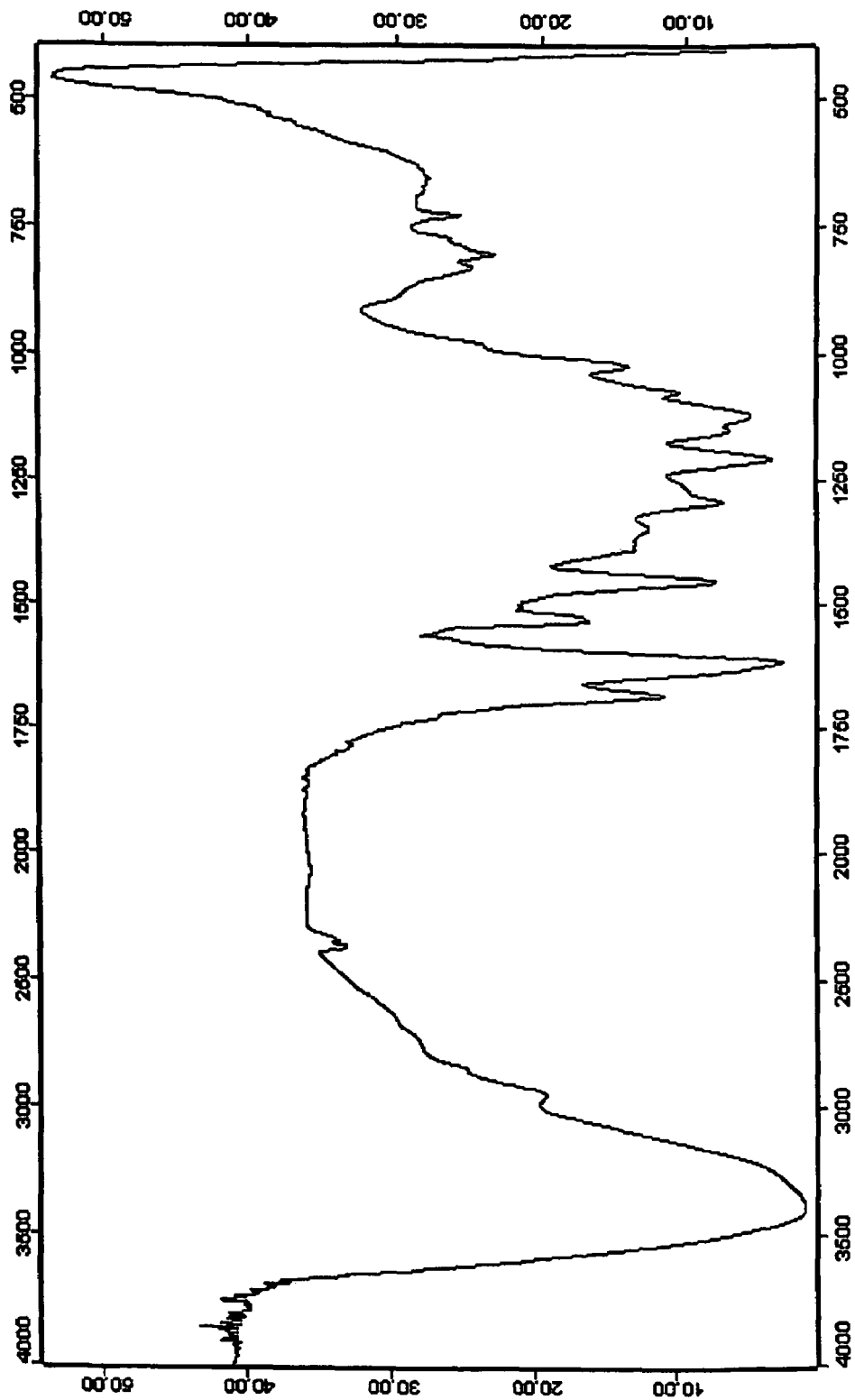
FIG. 36 is an IR spectrum of a purified cranberry polar proanthocyanidin composition ("fraction 7").

The non-polar proanthocyanidins fraction ("fraction 6") was further purified by gel filtration chromatography. A portion (48 mg) of the non-polar proanthocyanidin fraction ("fraction 6") isolated during the VLC separation was dissolved in 20 mL of warm water and loaded onto a 14 mL Sephadex LH-20 column that had previously been equilibrated with water. The loading eluent was collected and combined with a 40 mL column water wash. Most of the non-polar proanthocyanidins eluted from the column at this point while most of the smaller flavonoid impurities were retained. The combined loading and wash eluents were freeze-dried to provide 32 mg of the purified non-polar proanthocyanidins "fraction 8." These solids possessed strong antiviral activity. FIGS. 21 and 23 show the HPLC chromatograms at 280 nm and 368 nm, respectively, of the non-polar proanthocyanidins ("fraction 6") before the Sephadex LH-20 column purification. FIGS. 22 and 24 show the HPLC chromatograms at 280 nm and 368 nm, respectively, of the purified non-polar proanthocyanidins ("fraction 8"). The peaks in FIG. 21 marked with asterisks are non-proanthocyanidin flavonoid compounds based on their UV spectra. These compounds are reduced in the purified non-polar product ("fraction 8") isolated after Sephadex LH-20 column as shown HPLC chromatogram at 280 nm in FIG. 22. The effect of the gel purification can be better seen by comparing the HPLC chromatogram at 368 nm of the non-polar proanthocyanidins before purification (FIG. 23). The non-proanthocyanidin impurities appear in FIG. 23 at 4-6 minutes and 15-17 minutes. Except for a small amount of the flavonoid compound eluting at 5.8 minutes, there is no trace of flavonoid compounds in the purified sample as shown in FIG. 24. A $^{13}$C NMR spectrum of the purified non-polar proanthocyanidin "fraction 8" is shown in FIG. 25. FIG. 33 shows an IR spectrum of fraction 7, and FIG. 34 shows an IR spectrum of "fraction 8."

Example 13

Purification of Blueberry Polar and Non-Polar Proanthocyanidins by VLC Followed by Semi-Preparative HPLC The starting material for this example was a phenolic-enriched "fraction 3" prepared from blueberries and isolated during the 70% ethanol elution from a brominated polystyrene resin. A portion (6.00 g) of "fraction 3" was dissolved in 80 mL of water and loaded onto a 30 mL C-18 VLC column as described previously. The loading eluent was collected and combined with 100 mL of a 0.1% TFA wash eluent ("fraction 5"). Next, the column was washed with 80 mL of 40% methanol to remove residual polar compounds ("fraction 5") and then with 80 mL of 70% methanol to give the non-polar proanthocyanidin fraction ("fraction 6"). Table 7 summarizes the results of this experiment.

TABLE 7

Purification of blueberry proanthocyanidins

| Sample | Solids (g) | Proanthocyanidins (mg) | % Proanthocyanidins purity |
|---|---|---|---|
| "fraction 3" | 6.00 | 1614 | 27 |
| Loading Eluent + Wash | 2.11 | 899 | 43 |
| 40% MeOH fraction | 2.46 | 580 | 24 |
| 70% MeOH fraction | 0.67 | 323 | 48 |

Figure 26:
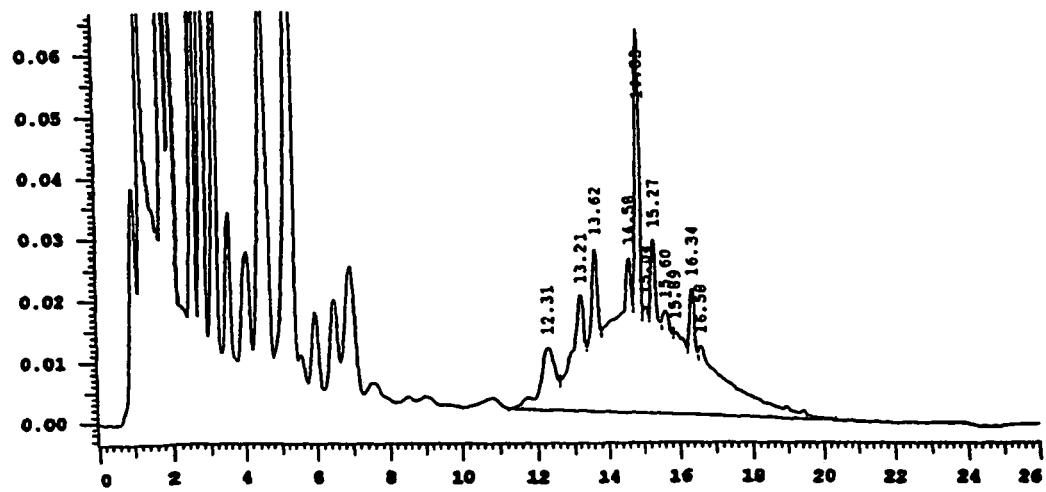
FIG. 26 is an HPLC chromatogram at 280 run of a blueberry polar proanthocyanidin composition ("fraction 5") isolated during VLC chromatography on C-18 media and before semi-preparative HPLC purification.
Figure 27:
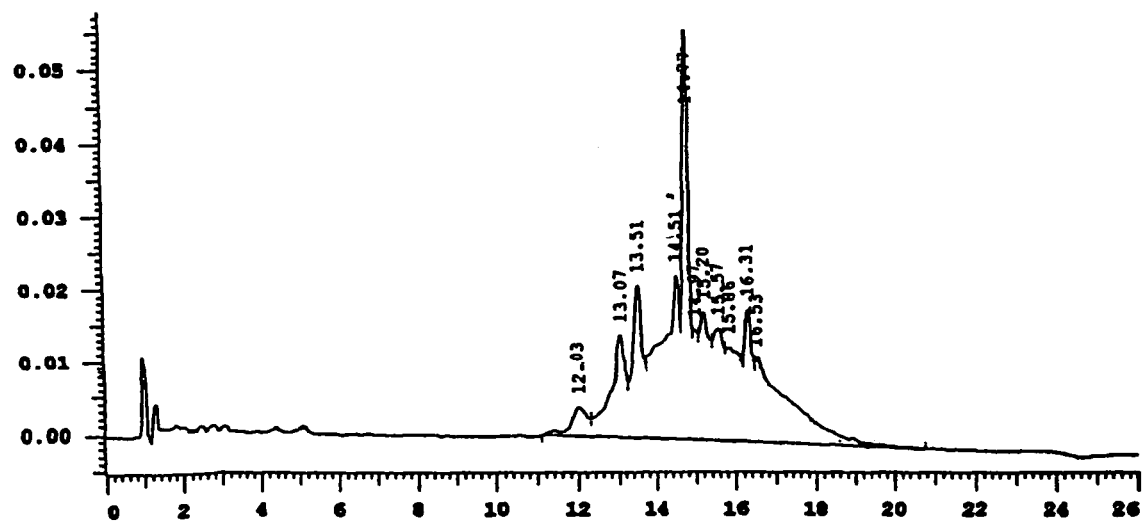
FIG. 27 is an HPLC chromatogram at 280 nm of a blueberry polar proanthocyanidin composition ("fraction 7") after purification by semi-preparative HPLC.
Figure 28:
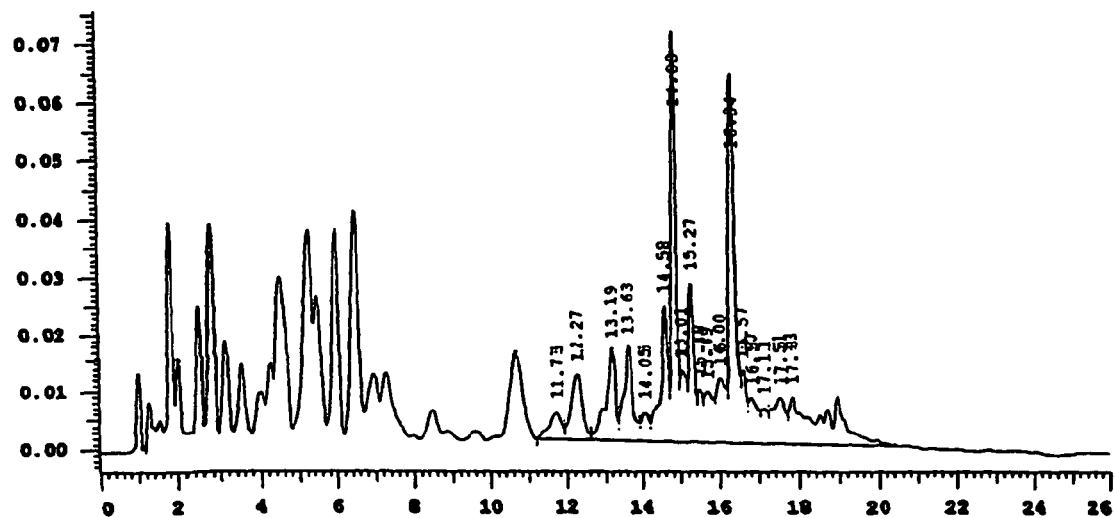
FIG. 28 is an HPLC chromatogram at 280 nm of a blueberry non-polar proanthocyanidin composition ("fraction 6") isolated during VLC chromatography on C-18 media and before semi-preparative HPLC purification.
Figure 29:
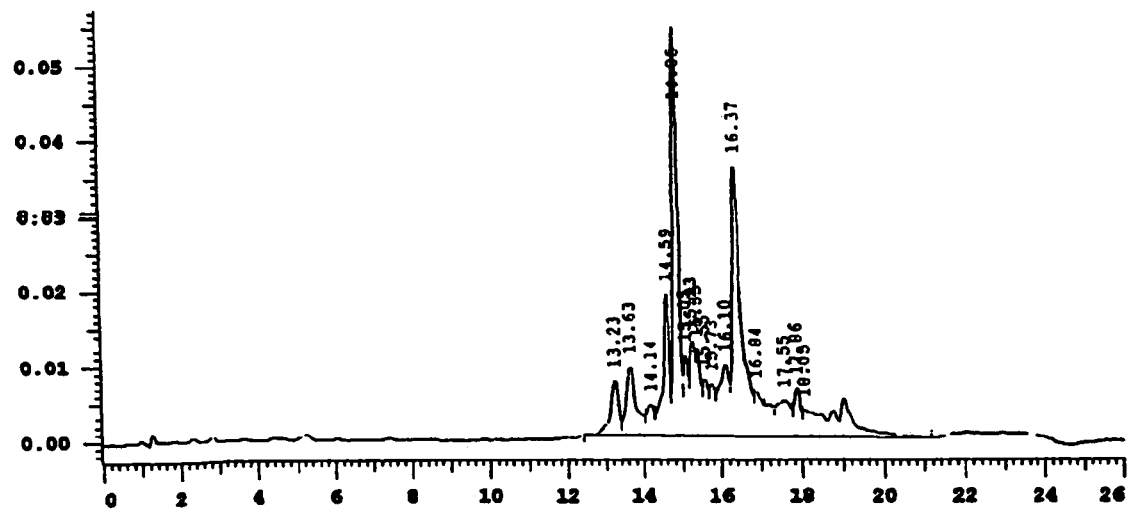
FIG. 29 is an HPLC chromatogram at 280 nm of a blueberry non-polar proanthocyanidin composition ("fraction 8") after purification by semi-preparative HPLC.
Figure 37:
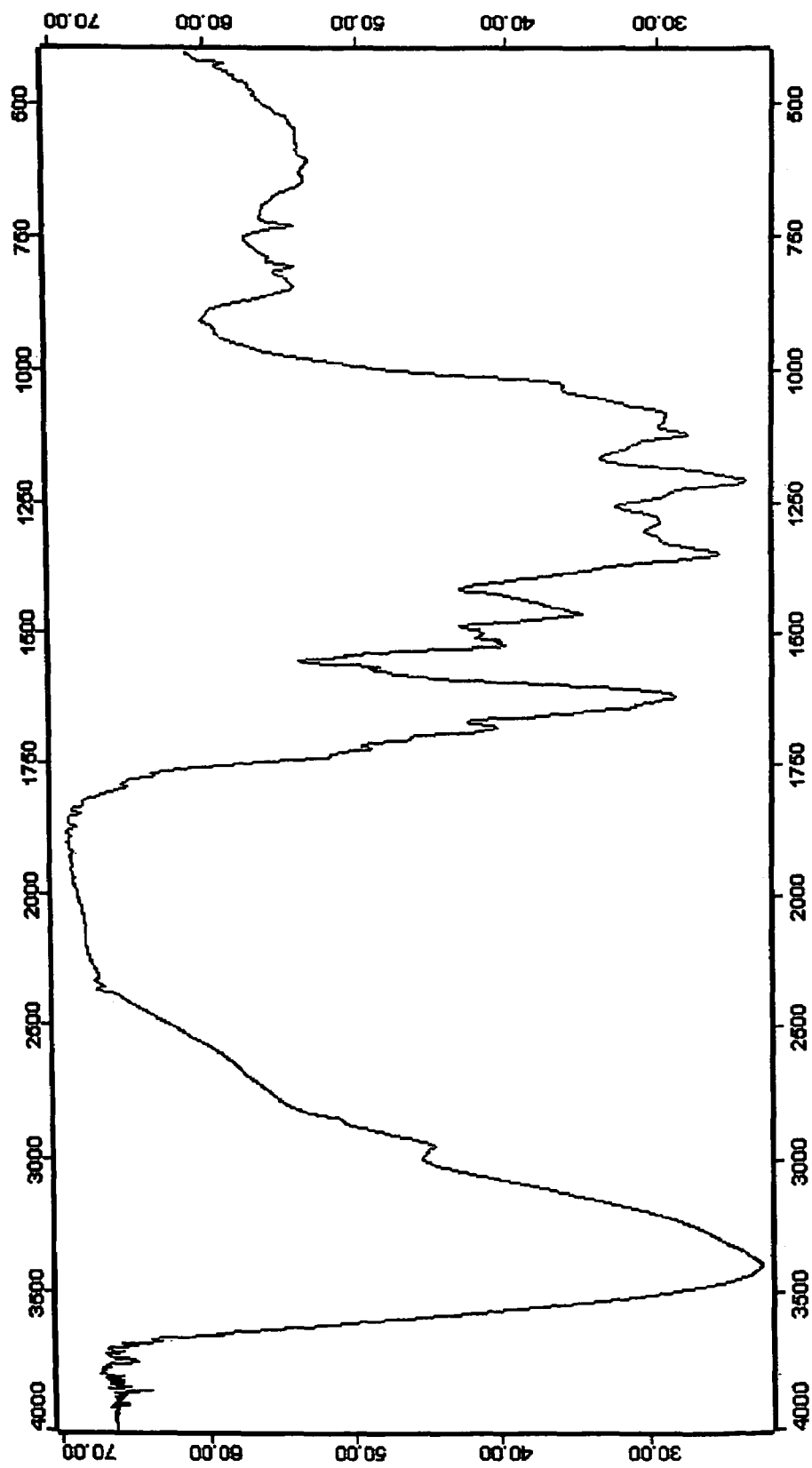
FIG. 37 is an IR spectrum of a purified blueberry polar proanthocyanidin composition ("fraction 7").
Figure 38:
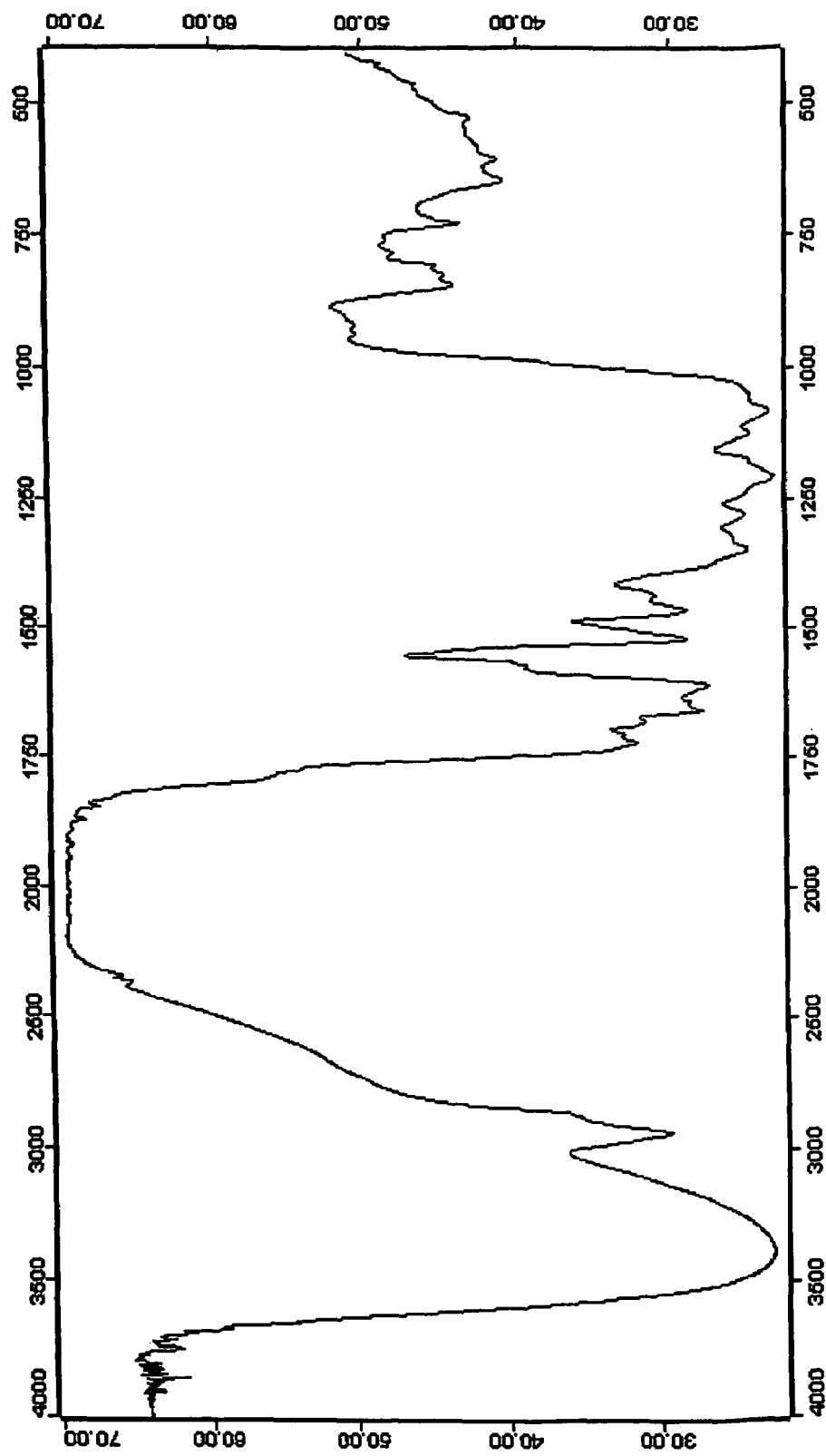
FIG. 38 is an IR spectrum of a purified blueberry non-polar proanthocyanidin composition ("fraction 8").

The polar proanthocyanidins "fraction 5" (loading eluent+wash) and the non-polar proanthocyanidins fraction 6 (70% methanol elution) were each further purified by semi-preparative HPLC by the method described in Example 12 to provide "fraction 7" and "fraction 8", respectively. The HPLC chromatograms at 280 nm of the blueberry polar proanthocyanidins fraction before and after the semi-preparative purification (i.e., "fraction 5" and "fraction 7") are shown in FIGS. 26 and 27, respectively. The HPLC chromatograms at 280 nm of the blueberry non-polar proanthocyanidins fraction before and after the semi-preparative purification (i.e., "fraction 6" and "fraction 8") are shown in FIGS. 28 and 29, respectively. The semi-preparative purifications of both the polar and non-polar fractions removed undesired anthocyanins and polar flavonoid compounds from the proanthocyanidins, as evidenced by the absence of peaks between about 0 and 8 minutes in FIGS. 27 and 29. FIG. 37 shows an IR spectrum of "fraction 7," and FIG. 38 shows an IR spectrum of "fraction 8."

Example 14

Figure 30:
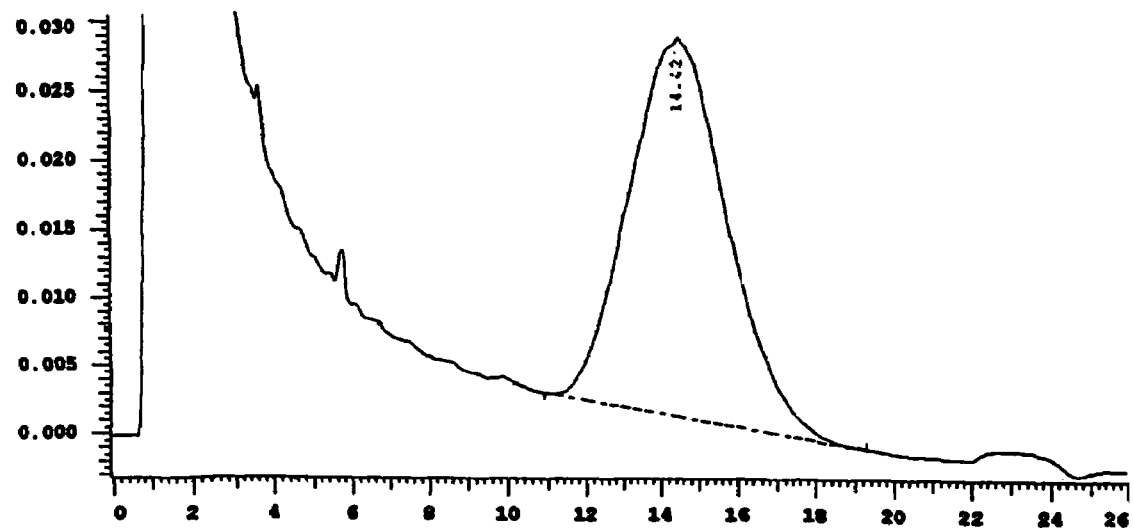
FIG. 30 is an HPLC chromatogram at 280 nm of a plum polar proanthocyanidin composition ("fraction 5") isolated during VLC chromatography on C-18 media and before semi-preparative HPLC purification.

Purification of Plum Polar and Non-Polar Proanthocyanidins by VLC Followed by Semi-Preparative HPLC The starting material for this example was a combination of "fraction 3" and "fraction 4" isolated from plums and containing approximately 17% total proanthocyanidins, of which 61% were designated as polar and 39% as non-polar. A portion (8.00 g) of this composition was dissolved in 100 mL of water containing 0.5% TFA and loaded onto a 45 mL C-18 VLC column as described previously. The loading eluent was collected, and the column was washed with 50 mL of 0.1% TFA. The loading eluent and wash fractions were combined to provide the polar proanthocyanidins fraction ("fraction 5"). An HPLC of the polar proanthocyanidin "fraction 5" is shown in FIG. 30. The column was eluted with 100 mL of 40% methanol containing 0.5% TFA followed by 100 mL of 70% methanol containing 0.5% TFA. All methanol fractions were combined to provide the non-polar proanthocyanidin fraction ("fraction 6"). Table 8 summarizes the results of this experiment.

TABLE 8

Purification of plum proanthocyanidins

| Sample | Solids (g) | Proanthocyanidins (mg) | % Proanthocyanidins purity |
|---|---|---|---|
| Plum fractions 3 and 4 | 8.00 | 1328 | 17 |
| Loading Eluent + Wash | 4.32 | 651 | 15 |
| 40% MeOH fraction | 3.76 | 486 | 13 |
| 70% MeOH fraction | 0.45 | 300 | 67 |

Figure 31:
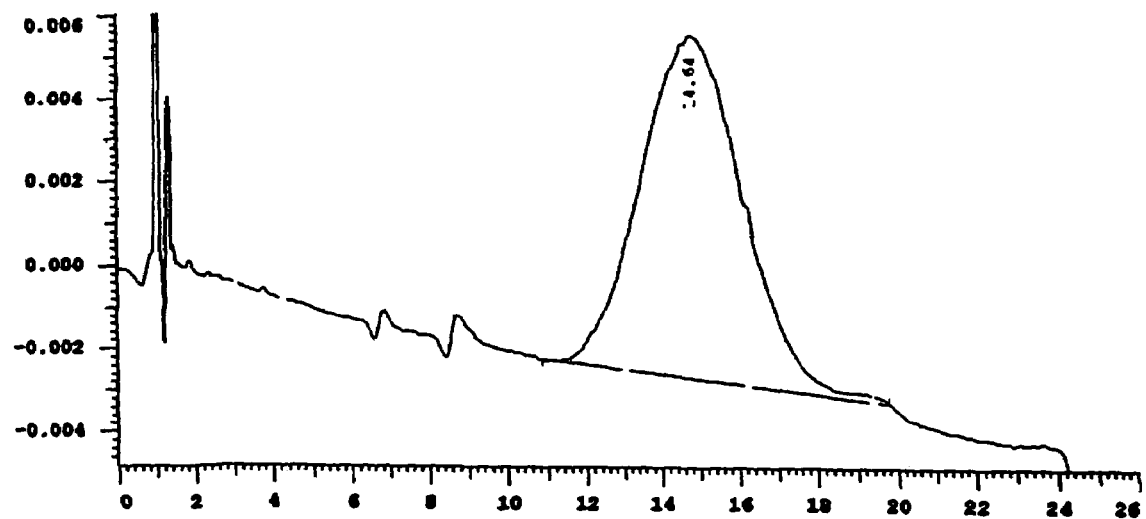
FIG. 31 is an HPLC chromatogram at 280 nm of a plum polar proanthocyanidin composition ("fraction 7") after purification by semi-preparative HPLC.
Figure 32:
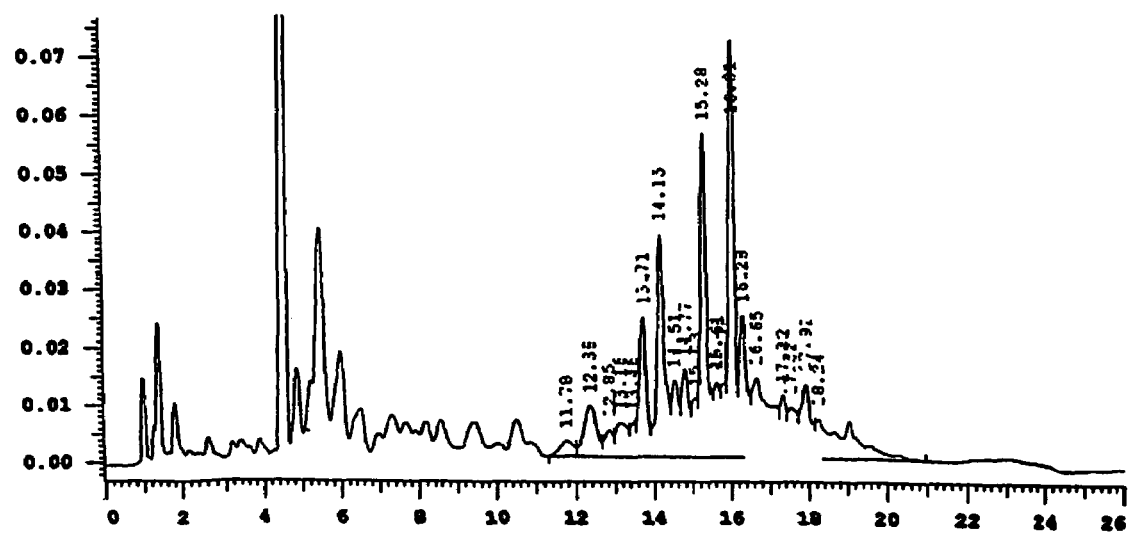
FIG. 32 is an HPLC chromatogram at 280 nm of a plum non-polar proanthocyanidin composition ("fraction 6") isolated during the 40% and 70% methanol elution from a VLC C-18 column.
Figure 39:
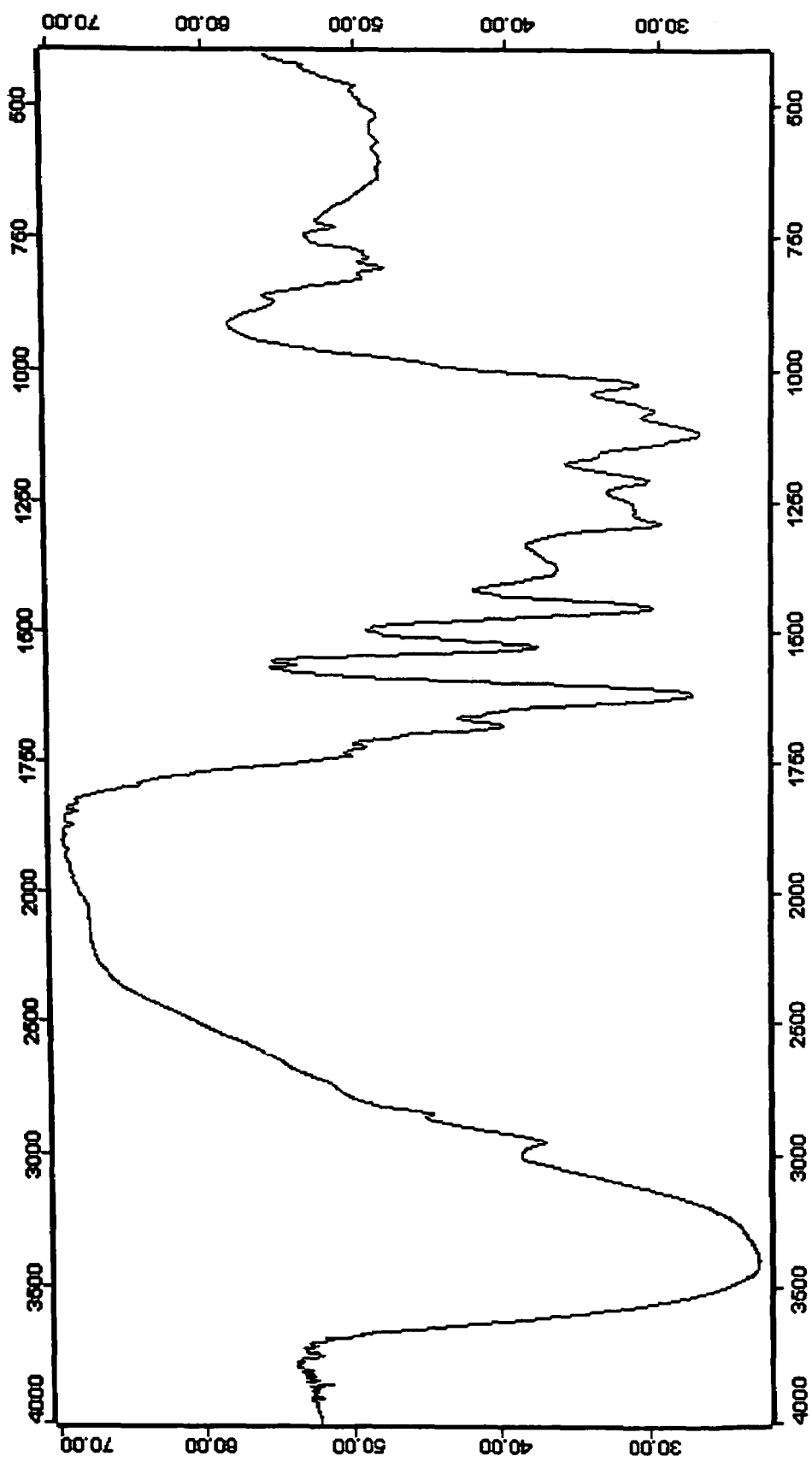
FIG. 39 is an IR spectrum of a purified plum polar proanthocyanidin composition ("fraction 7").
Figure 40:
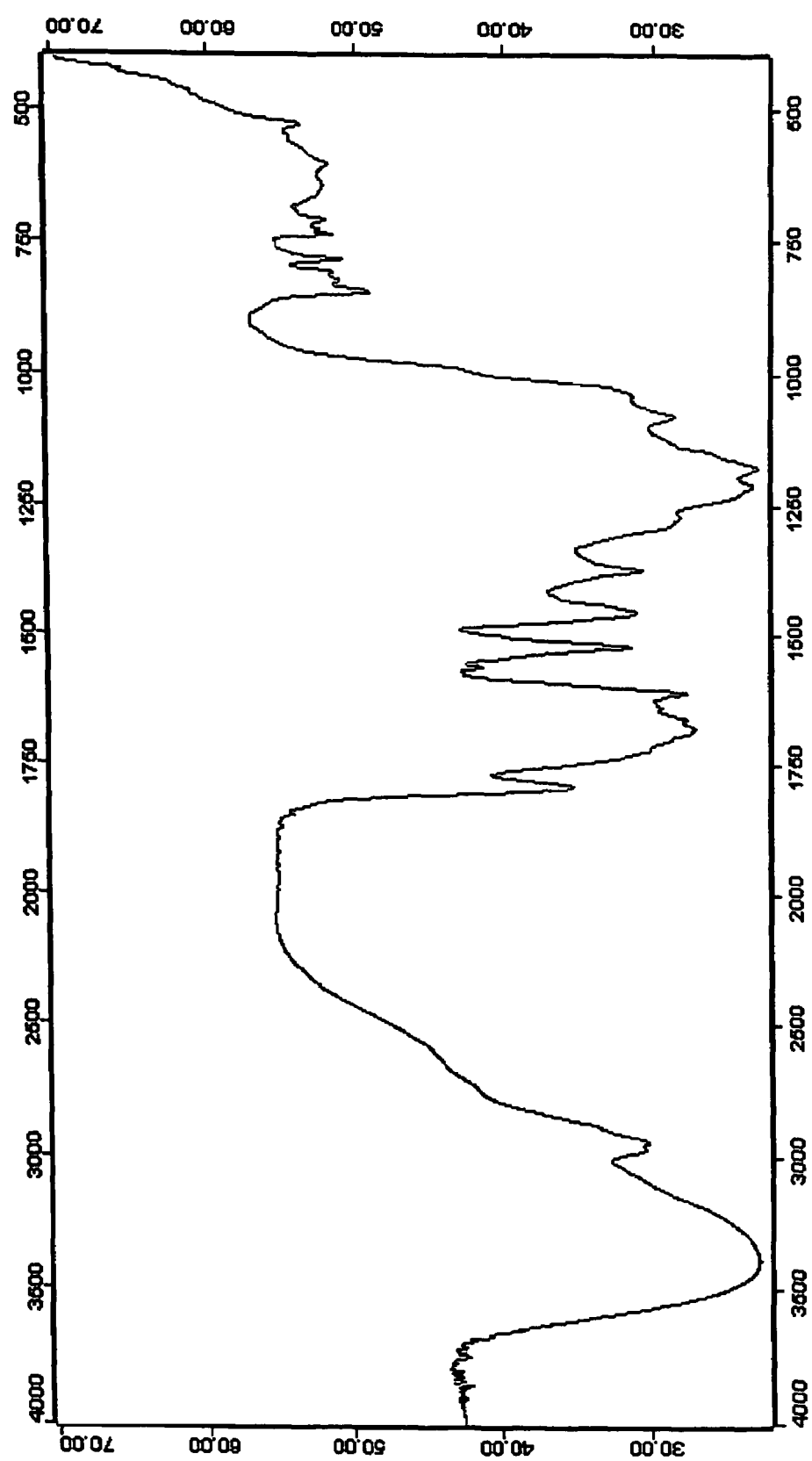
FIG. 40 is an IR spectrum of a purified plum non-polar proanthocyanidin composition ("fraction 6").

The polar proanthocyanidin "fraction 5" (combined loading eluent and wash eluent) was further purified by semi-preparative HPLC by the method described in Example 12 to provide "fraction 7." Removal of anthocyanins and other more polar impurities increased the proanthocyanidin purity of the sample from 15% to 100%. The HPLC chromatogram at 280 nm of the purified polar proanthocyanidin "fraction 7" is shown in FIG. 31. The non-polar "fraction 6" (combined 40% and 70% methanol washes) was not purified further. The HPLC chromatogram at 280 nm of the non-polar proanthocyanidin "fraction 6" is shown in FIG. 32. FIG. 39 is an IR spectrum of "fraction 7" and FIG. 40 is an IR spectrum of "fraction 6".

Example 15

Purification of Proanthocyanidins Fraction from Elderberry VLC Fraction

A VLC column was prepared using Amberchrom CG-71cd resin (80-160 μm particle size, TosoHaas; Philadelphia, Pa.). A water extract of elderberry was prepared and a portion of this extract was loaded onto the VLC column. The column was then washed with water and eluted using 30%, 40%, 50%, 60%, 70%, and 100% methanol. All fractions eluted with methanol were retained separately. The VLC fraction eluted with 50% methanol was evaporated on a rotary evaporator to remove the methanol and then lyophilized to remove the water. The dried material was ground to a powder using a mortar and pestle. The dried sample was assayed by HPLC using the method as described in Example 10. Using the results of this assay, a semi-preparative HPLC method was derived from the analytical HPLC method to isolate the proanthocyanidins. The mobile phase was: channel A=100% acetonitrile; channel B=0.5% trifluoroacetic acid in water; channel C=100% methanol. The flow rate was set at 30 mL/min. The gradient employed is provided in Table 9.

TABLE 9

HPLC gradient for purification of elderberry proanthocyanidins

| Time (min) | % A | % B | % C |
|---|---|---|---|
| 0.0 | 11.0 | 81.0 | 8.0 |
| 9.0 | 11.0 | 81.0 | 8.0 |
| 17.0 | 34.0 | 58.0 | 8.0 |
| 22.0 | 34.0 | 58.0 | 8.0 |
| 23.0 | 92.0 | 0.0 | 8.0 |
| 28.0 | 92.0 | 0.0 | 8.0 |
| 28.1 | 11.0 | 81.0 | 8.0 |
| 36.0 | 11.0 | 81.0 | 8.0 |

Approximately 500 mg of the dried material was dissolved in water at a solids concentration of approximately 50 mg/mL. A very small injection was made to determine the retention time of the relevant peaks. Based on this initial injection, two peaks were collected: Peak A, which eluted between 14 and 22 minutes and Peak B, which eluted between 26 and 28 minutes. Five injections of the concentrated solution were made, and the appropriate collections of each peak were pooled from each injection. The sample obtained by the collection of Peak A was determined to contain the proanthocyanidins and was evaporated to remove the organic solvents and a portion of the water. The concentrated sample was assayed using the HPLC method as described in Example 10. The chromatographic purity of the sample was determined to be 93.9%. The sample was then lyophilized to obtain the dry material. Once dry, a small portion of the sample was brought up in 70% ethanol at a concentration of 1.918 mg/mL and re-assayed by the same HPLC method. Using the results of this analysis and the previously obtained chromatographic purity, a peak area response factor was determined. This information was used to determine the proanthocyanidins concentration in other purified fractions. The HPLC chromatogram at 280 nm of the proanthocyanidin "standard" is shown in FIG. 14.

Example 16

Purification of Cranberry Proanthocyanidins by VLC Followed by Semi-Preparative HPLC The starting material for this example was 8.00 g of purified cranberry extract ("fraction 3"+"fraction 4") comprising 14% total proanthocyanidins. This material was dissolved in 100 mL of water containing 1 mL of trifluoroacetic acid and loaded onto a 50 mL C-18 VLC column as described previously. The loading eluent (100 mL) was collected and combined with 50 mL of 0.1% TFA wash eluent to obtain "fraction 5". Next the column was washed with 100 mL of 40% methanol to remove residual polar compounds and eluted with 100 mL of 70% methanol to give the non-polar proanthocyanidins "fraction 6". Table 10 summarizes the results of this experiment.

TABLE 10

Purification of cranberry proanthocyanidins

| Sample | Solids (g) | Proanthocyanidins (mg) | % Proanthocyanidins purity |
|---|---|---|---|
| Cranberry fractions 3 + 4 | 8.00 | 1514 | 14.3 |
| Loading Eluent + Wash | 3.60 | 748 | 20.8 |
| 40% MeOH fraction | 3.39 | 677 | 20.0 |
| 70% MeOH fraction | 0.44 | 93 | 21.1 |

Figure 41:
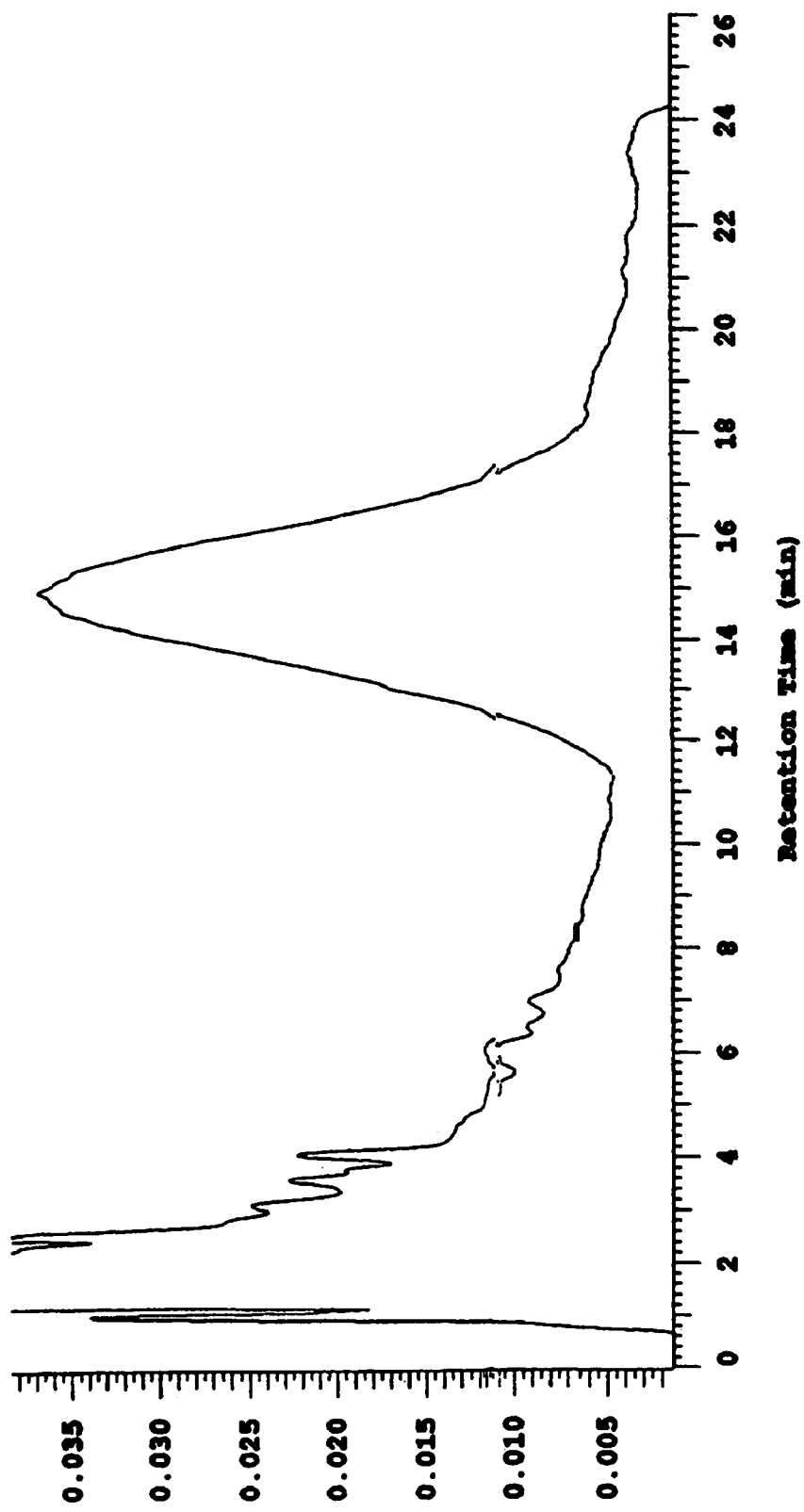
FIG. 41 is an HPLC chromatogram at 280 nm of a cranberry polar proanthocyanidin composition ("fraction 5") before semi-preparative HPLC purification.
Figure 42:
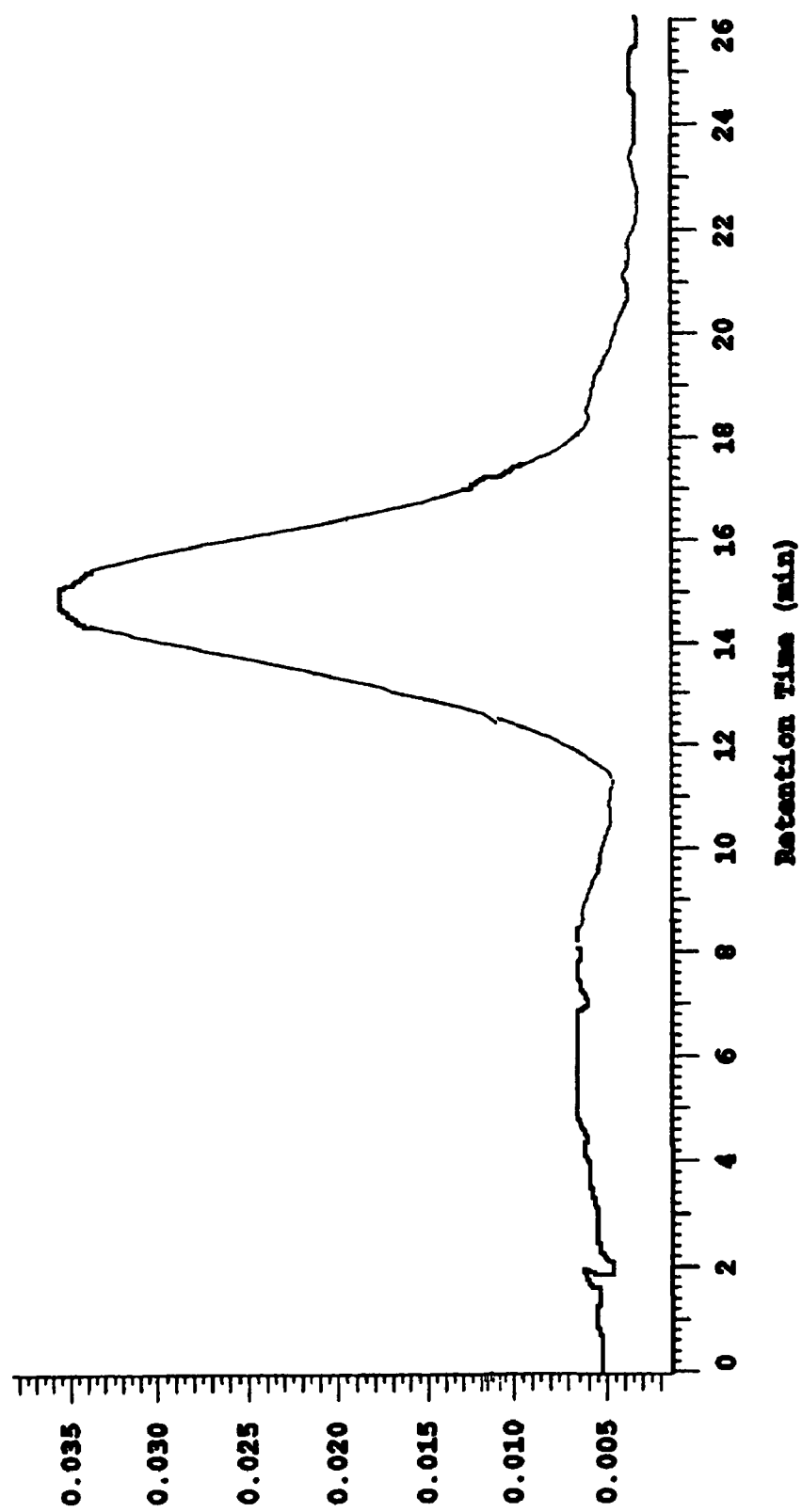
FIG. 42 is an HPLC chromatogram at 280 nm of a cranberry polar proanthocyanidin composition ("fraction 7") after semi-preparative HPLC purification.
Figure 43:
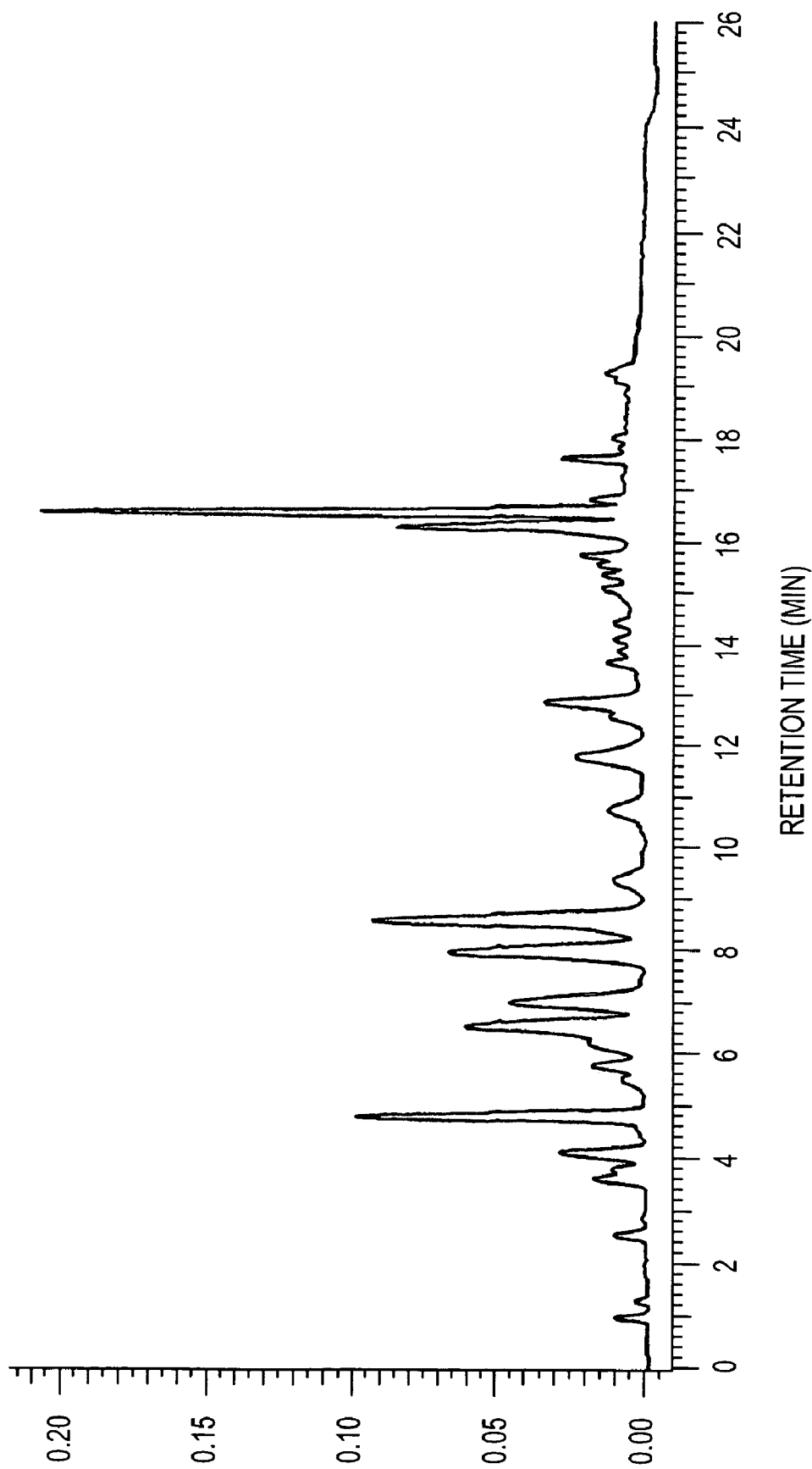
FIG. 43 is an HPLC chromatogram at 280 nm of a cranberry non-polar proanthocyanidin composition ("fraction 6").

The polar proanthocyanidins fraction (loading eluent+wash) was further purified by semi-preparative HPLC by the method described in Example 12 to obtain "fraction 7". FIG. 41 is an HPLC chromatogram of the polar proanthocyanidins fraction before semi-preparative purification, and FIG. 42 is an HPLC chromatogram of the polar proanthocyanidins fraction after purification. FIG. 43 is an HPLC chromatogram of the non-polar proanthocyanidins fraction. Polar non-proanthocyanidin compounds such as anthocyanins that eluted before the proanthocyanidins were removed in this process.

Example 17

Herpes Simplex Virus 2 Assay of Elderberry Fractions

The antiviral activities of a crude elderberry extract and fractions 1, 3 and 4 isolated as described in Example 6 were determined using the viral cytopathic effect (CPE) assay. This assay has previously been described (Wyde, et al., *Drug Develp. Res.* 28:467-472 (1993)). All antiviral activities are reported as 50% effective dose ($ED_{50}$).

Table 11 summarizes the $ED_{50}$ for CPE inhibition for the four compositions tested.

TABLE 11

$ED_{50}$ for CPE inhibition of elderberry fractions

| Composition | CPE Inhibition ($ED_{50}$) |
|---|---|
| Crude extract | >100 µg/mL |
| "fraction 1" | >100 µg/mL |
| "fraction 3" | >100 µg/mL |
| "fraction 4" | <0.03 µg/mL |

Example 18

Viral Assays

Phenolic-enriched compositions of this invention prepared according to this invention have demonstrated broad activity against a variety of DNA and RNA viruses and are suitable as active ingredients useful in treating inflammation in humans and animals. In cell culture, the enriched compositions exhibit potent activity against isolates and laboratory strains of respiratory syncytial virus (RSV), influenza A and B virus, parainfluenza virus (PIV), as well as other respiratory and Herpes simplex viruses. Phenolic-enriched compositions are suitable as active ingredients useful in treating a wide range of viral infections in humans and animals.

Assays used to measure activity against each virus are well known to those skilled in the art. Minced specific target tissue was exposed to the desired virus and the rate of growth of the virus was measured in the presence and in the absence of the test materials. The antiviral activities of purified proanthocyanidin-enriched compositions prepared from various plant materials containing phenolic compounds were determined.

Cell lines: The viral assays used the following cells/cell lines in determining relative $ED_{50}$ (50% effective dose) or 50% inhibitory endpoints: RSV (respiratory syncytial virus) and PIV (parainfluenza virus) assays used MA-104 cells originating from African green monkey kidneys; Influenza A and B assays used MDCK cells originating from canine kidneys; *Rhinovirus* assays used HeLa and KB cells; Herpes simplex viruses 1 and 2 used HHF cells taken from human foreskin fibroblasts; West Nile viral assays used Vero cells taken from African green monkey kidneys; Adenovirus type 1 assays used A549 cells originating from human lung carcinoma; and Punta Toro A assays used LLC-MK2 cells originating from Rhesus monkey kidneys.

The assays used known drug standards (ribivarin or acyclovir) as positive controls. The $ED_{50}$s for ribivarin in the assays used in this Example are as follows: RSV (respiratory syncytial virus) assay $ED_{50}$=20 µg/mL; PVI (parainfluenza virus) assay $ED_{50}$=20 µg/mL; Influenza A and B assays $ED_{50}$=2-3 µg/mL; *Rhinovirus* assay $ED_{50}$<1 µg/mL; West Nile viral assay $ED_{50}$=20 µg/mL; Adenovirus type 1 assay $ED_{50}$=10 µg/mL; and Punta Toro A assay $ED_{50}$=20 µg/mL. Herpes simplex 1 and 2 assays used acyclovir as a positive control, which has an $ED_{50}$ of 1-2 µg/mL in the HSV1 and HSV2 assays.

The data obtained in the viral assays for certain compositions of this invention are provided in Table 12. In cell cultures, the compositions exhibited potent activity against isolates and laboratory strains of influenza A virus (strains H1N1 and H3N3), influenza B virus, adenovirus type 1, Punta Toro A virus, and *Rhinovirus* type 2. Comparison of the bioactivity data in Table 12 to acyclovir and ribivarin in the antiviral screenings clearly shows that the compositions of this invention are biologically active in these assays and compete favorably with the well-established pharmaceuticals used to treat these viral diseases.

TABLE 12

IC$_{50}$'s (μg/mL) of various fractions in various antiviral assays

| Source | Fraction | Influenza A (H1N1) | Influenza A (H3N2) | Influenza B | Adenovirus Type 1 | Punta Toro A | Rhinovirus Type 2 | West Nile virus | Varicellazoster virus | HSV-1 | HSV-2 |
|---|---|---|---|---|---|---|---|---|---|---|---|
| Cranberry | 4 | 3.2 | 3.2 | 3.2 | 20 | | | 5.6 | | 61 | 15 |
| Plum | 4 | 32 | 32 | 32 | 25 | | | 70 | | 70 | 32 |
| Blueberry | 4 | 32 | 32 | 32 | 30 | 25 | | 30 | 31 | 45 | 11.4 |
| Elderberry | 4 | 28-55 | 28-55 | | | | | | 88 | 45 | 11 |
| Elderberry | 6 | | | | | | 15 | | | | |
| Elderberry | 7 | | | | | | | inactive | | inactive | inactive |
| Elderberry | 8 | | | | | | | 28 | 35 | | |
| Elderberry | FIG. 14 | | | | | | | inactive | 0.08 | 67.7 | 49 |
| Grape seed* | NA | 4 | 6 | 3.2 | | 20 | | 6.8 | | | |

*(Nature's Plus; Melville, NY)

Example 19

Evaluation of COX-2 Activity of Phenolic-Enriched Compositions

Cyclooxygenase enzymes (COX-1 and COX-2) catalyze the conversion of arachidonic acid and other essential fatty acids into various prostaglandins. Prostaglandins are hormone-like substances responsible for inflammation in mammals. Inhibition of the COX-2 enzymes can reduce inflammation in tissue with minimal side effects. On the other hand, inhibition of COX-1 causes gastric ulceration and other undesirable side effects in the body. Complete inhibition of the COX-1 enzyme is not desirable. Compounds that selectively inhibit COX-2 enzyme are better anti-inflammatory agents. Phenolic-enriched compositions of this invention prepared from plant materials have been shown to inhibit the COX-2 enzyme, and are suitable as active ingredients useful in treating inflammation in humans and animals.

In this assay the material to be assayed was mixed with minced specific murine or bovine organ tissues that are known to contain the desired enzyme. Arachidonic acid was added to this mixture. The rate of uptake of oxygen is measured and compared with the rate of uptake observed with known COX inhibitors. The COX-2 assay is based on quantitative production of PGE$_2$ from arachidonic acid using human recombinant COX-2 positive cells.

The results for several compositions are shown in Table 13. Comparison of the data for the compositions shown in Table 13 with determined COX-2 bioactivities of known drug standards (aspirin and indomethacin) clearly shows that the purified proanthocyanidin-enriched compositions of this invention are biologically active in the COX-2 assay. Aspirin is active against COX-2 at 660 μg/mL and against COX-1 at 240 μg/mL. Indomethacin is active against COX-2 at 10 μg/mL. The compositions in Table 13 therefore show a 2.5 to 6 fold increase in potency in the COX-2 assay over the most commonly used treatment for inflammation (i.e., aspirin), and are indicative of the utility of the purified proanthocyanidin-enriched compositions of this invention in treating inflammation in mammals.

TABLE 13

COX-2 activities for proanthocyanidin enriched compositions

| Source | Fraction | IC$_{50}$ (μg/mL) |
|---|---|---|
| Blueberry | 3 | 108 |
| Cranberry | 4 | 218 |
| Grape seed* | N/A | 275 |
| Elderberry | 4 | >1000 |
| Plum | 4 | >1000 |

*(Nature's Plus; Melville, NY)

Example 20

Purification of a Plum Concentrate Using a Protonated Tertiary Amine-Substituted Polystyrene Resin To 275 g of plum concentrate (Sunsweet; Yuba City, Calif.) was added 1460 mL of room temperature water. The mixture was mixed thoroughly and then acidified by adding 4 mL of concentrated sulfuric acid, and then the acidified solution was filtered through a Whatman #1 paper filter.

The filtered solution (1.7 L) was loaded on to a conditioned and equilibrated column (0.96 meter, 170 mL) containing a tertiary amine-substitute polystyrene resin (Optipore SD-2; Dow Chemical, Midland, Mich.) at a flow rate of approximately 1.5 mL/min (0.53 column volumes per hour). All of the prepared material was loaded onto the column, and then the column was washed with water containing 0.038% sulfuric acid. The column was eluted with 6 column volumes of 50% ethanol/water and then with 5 column volumes of 90% ethanol/water. Each elution solvent was acidified to 0.038% sulfuric acid. Both eluents were collected as one sample and assayed for total phenolic compounds. Based on the results of this assay, which indicated incomplete recovery of the phenolic compounds, the column was washed with an additional 2.5 column volumes of 50% ethanol and the isolated eluent was combined with the earlier eluents. The combined eluents were evaporated to remove the ethanol and some of the water and then placed on a lyophilizer for 48 hours. The dried material obtained from these fractions was assayed for total phenolic compounds using the Folin-Ciocalteu spectrophotometric method (absorbance at 760 nm against a gallic acid standard). This same dried fraction was also assayed for proanthocyanidins using the HPLC method (absorbance at 280 nm against a catechin standard), as described herein.

The isolated purified plum extract material comprised 22.4% by weight total phenolic compounds and 5.1% proanthocyanidins for the product fraction. The HPLC chromatogram of the purified plum extract at 280 nm is shown FIG. 44. The overall recovery for the column was approximately 91% for total phenolic compounds and 95% for proanthocyanidins. FIG. 45 shows an HPLC chromatogram at 280 nm of the 50% ethanol elution fractions collected during elution of a plum concentrate from a brominated polystyrene resin for comparison.

Example 21

Purification of a Plum Concentrate Using an Unsubstituted Aromatic Polymer Resin To 519 g of plum concentrate (Sunsweet; Yuba City, Calif.) was added 2750 mL of room temperature water. The mixture was mixed thoroughly and then acidified by adding 7 mL of concentrated sulfuric acid, and then the acidified solution was filtered through a Whatman #1 paper filter.

The filtered solution (3.27 L) was loaded on to a conditioned and equilibrated column (0.96 meter, 170 mL) containing SP-70, an unsubstituted polystyrene divinylbenzene copolymer resin (Mitsubishi Chemical; Tokyo, Japan) at a flow rate of approximately 1.5 mL/min (0.53 column volumes per hour). Loading continued until the concentration of polyphenols in the out-flow was 18% of that in the column feed, at which point loading was stopped and the column was washed with water containing 0.038% sulfuric acid. The column was eluted with 5 column volumes of 50% ethanol/water and then with 5 column volumes of 90% ethanol/water, each containing 0.038% sulfuric acid. The eluents were collected separately, evaporated to remove the ethanol and some of the water, and then placed on a lyophilizer for 48 hours. The dried material from the 50% ethanol elution was assayed for total phenolic compounds using the Folin-Ciocalteau spectrophotometric method (absorbance at 760 nm against a gallic acid standard). This same dried fraction was also assayed for proanthocyanidins using the HPLC method (absorbance at 280 nm against a catechin standard), as described herein. The dried material from the 90% ethanol fraction was not assayed.

The purified plum material comprised 34% by weight total phenolic compounds and 4.9% proanthocyanidins for the 50% ethanol fraction. The overall recovery for the column was approximately 95% for total polyphenols and over 100% for proanthocyanidins.

Example 22

Purification of a Cranberry Concentrate Using a Protonated Tertiary Amine-Substituted Polystyrene Resin To 130 mL of concentrate (SVZ USA; Othello, Wash.) was added 1700 mL of room temperature water. The 130 mL of concentrate used was comprised of 106 mL of one cranberry concentrate (Lot #02-1377) and 24 mL of another cranberry concentrate (Lot #02-11155), both from the same source. The mixture was mixed thoroughly and then acidified by adding 3 mL of concentrated sulfuric acid, after which the acidified solution was filtered through a Whatman #1 paper filter.

The filtered solution (1.83 L) was loaded on to a conditioned and equilibrated resin column (0.96 meter, 170 mL) containing Optipore SD-2 (Dow Chemical; Midland, Mich.), a tertiary amine-substituted polystyrene resin, at a flow rate of approximately 1.8 mL/min (0.63 column volumes per hour). All of the prepared material was loaded onto the column. After loading, the column was washed with water containing 0.038% sulfuric acid.

The column was eluted with 6 column volumes of 50% ethanol/water and then with 5 column volumes of 90% ethanol/water. Each elution solvent was acidified to 0.038% sulfuric acid. Both elutions were collected as one sample and assayed. The combined elution fraction was evaporated to remove the ethanol and a portion of the water, and then placed on a lyophilizer for 48 hours. The dried material was assayed for total phenolic compounds using the Folin-Ciocalteau spectrophotometric method (absorbance at 760 nm against a gallic acid standard) and for anthocyanins by standard spectrophotometric determination of absorbance 535 nm against a cyanidin chloride standard (101.1 absorbance units/mg/mL). This same dried fraction was also assayed for proanthocyanidins using the HPLC method (absorbance at 280 nm against a catechin standard) as described herein. The purified cranberry extract material comprised 30.3% by weight total phenolic compounds, 1.8% anthocyanins, and 12.9% proanthocyanidins for the product fraction.

Figure 46:
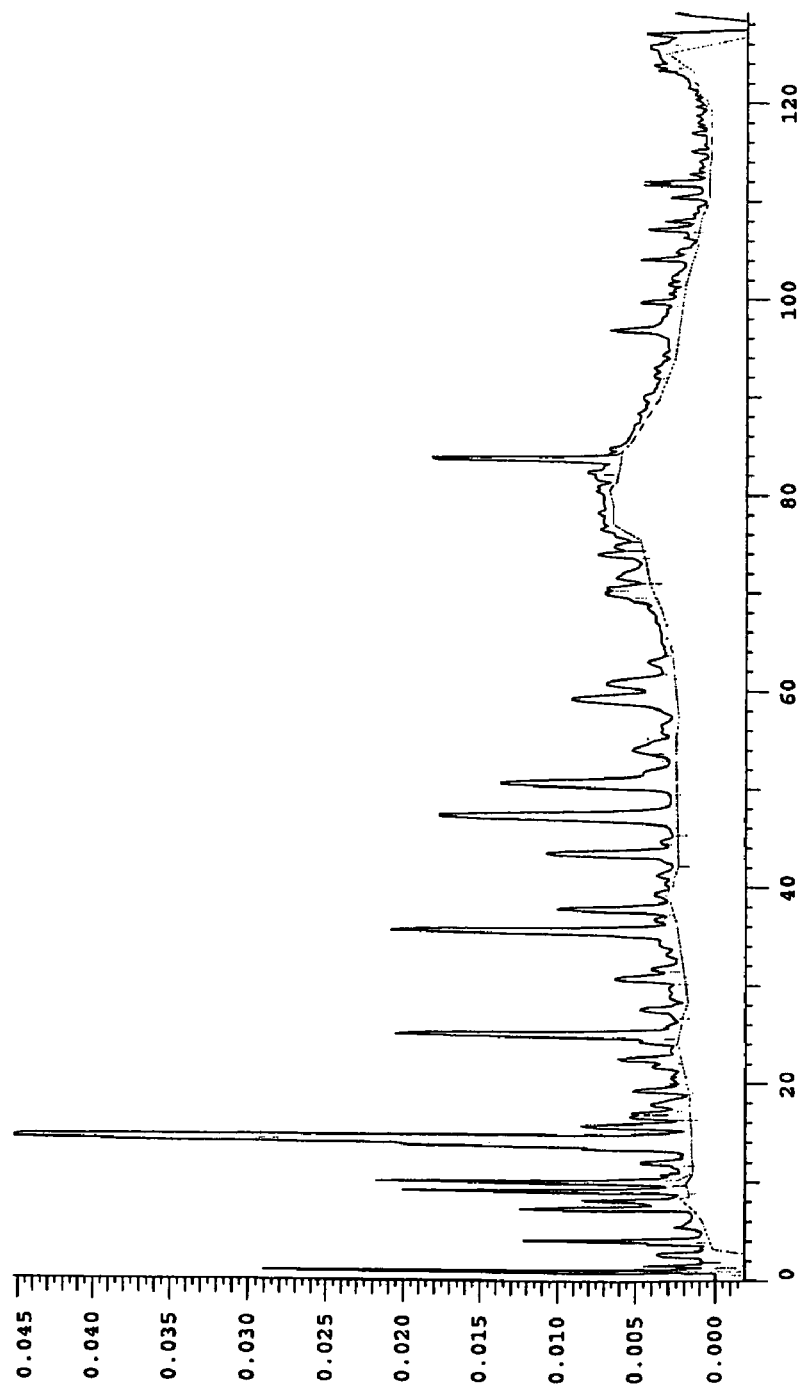
FIG. 46 is an HPLC chromatogram at 280 nm of the combined 50% and 90% ethanol elution fractions collected during elution of a cranberry concentrate from a protonated tertiary amine-substituted polystyrene resin.
Figure 47:
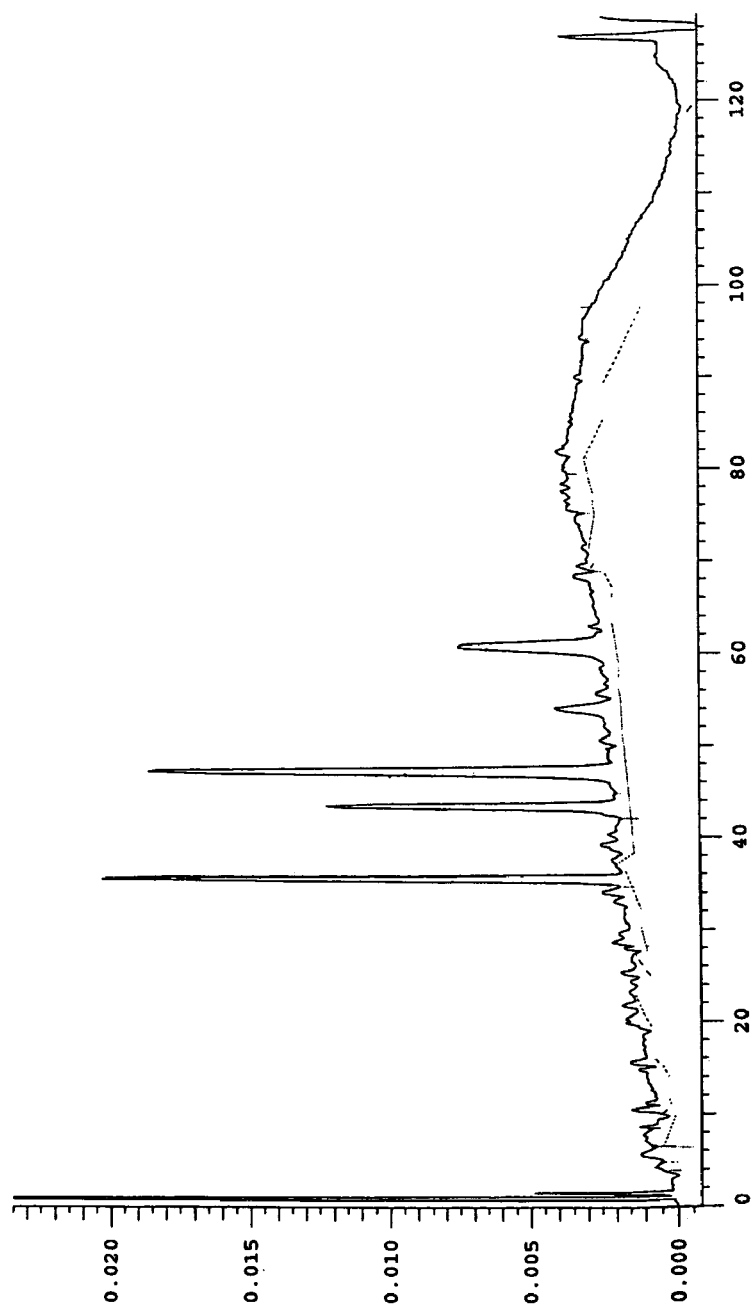
FIG. 47 is an HPLC chromatogram at 510 nm of the combined 50% and 90% ethanol elution fractions collected during elution of a cranberry concentrate from a protonated tertiary amine-substituted polystyrene resin.
Figure 48:
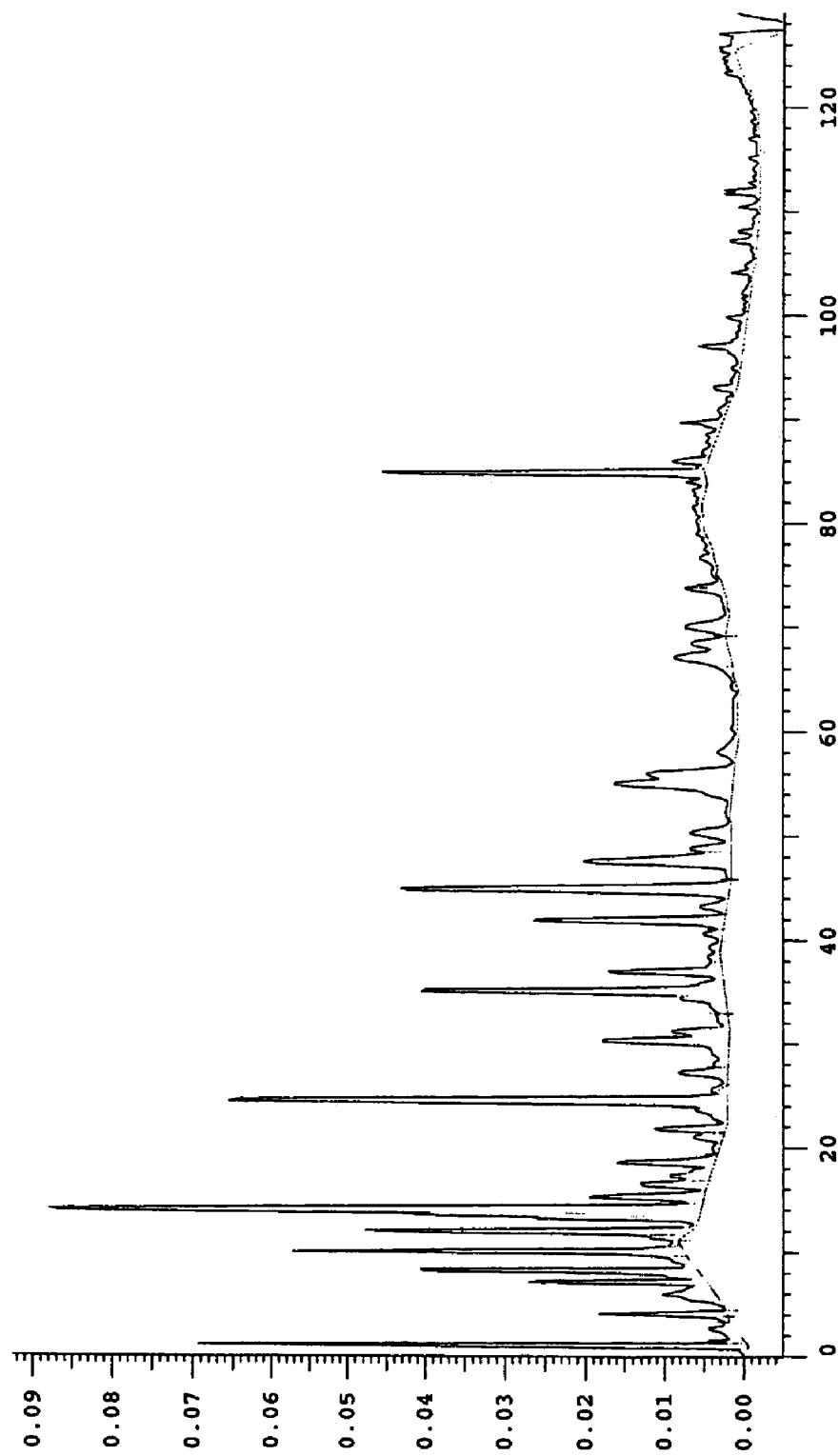
FIG. 48 is an HPLC chromatogram at 280 nm of the combined 50% and 90% ethanol elution fractions collected during elution of a cranberry concentrate from a brominated polystyrene resin.
Figure 49:
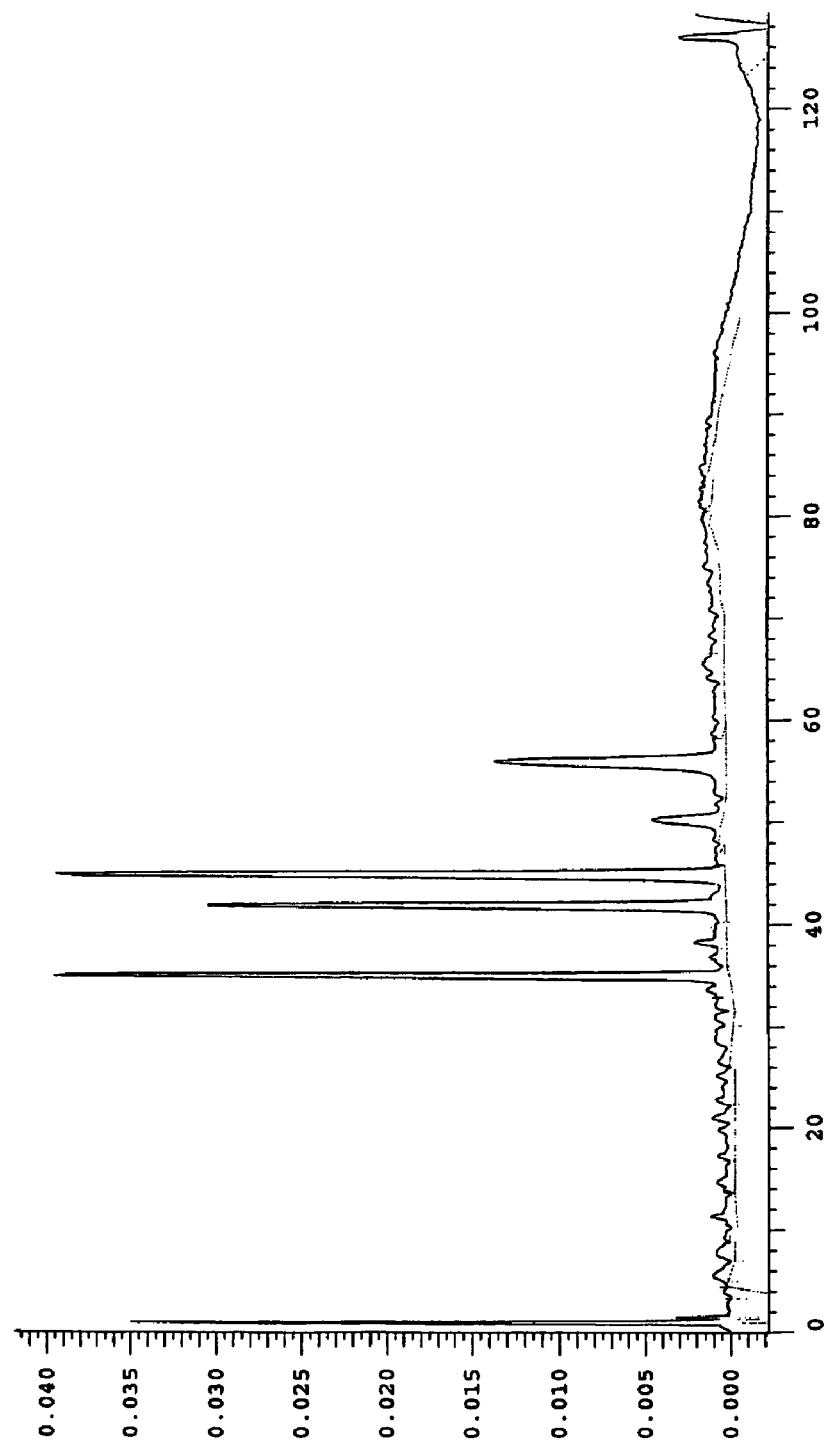
FIG. 49 is an HPLC chromatogram at 510 nm of the combined 50% and 90% ethanol elution fractions collected during elution of a cranberry concentrate from a brominated polystyrene resin.

FIGS. 46 and 47 are HPLC chromatograms at 280 nm and 510 nm, respectively of the cranberry combined 50% and 90% ethanol elution fractions. A comparison of the HPLC chromatograms in FIGS. 46 and 47 with the HPLC chromatograms 280 nm and 510 nm of a cranberry extract eluted from a brominated resin (FIGS. 48 and 49, respectively) shows very slight differences. These differences can be traced to the conditions at the time of the analysis and the slight variations that exist among the starting materials.

Example 23

Additional plant materials were extracted and purified according to this invention to provide proanthocyanidin-enriched compositions. Non-limiting examples of purified proanthocyanidin compositions prepared according to the methods of this invention are shown in Table 14. The percentage of proanthocyanidins shown is the percent by weight of the purified composition.

TABLE 14

Figure 44:
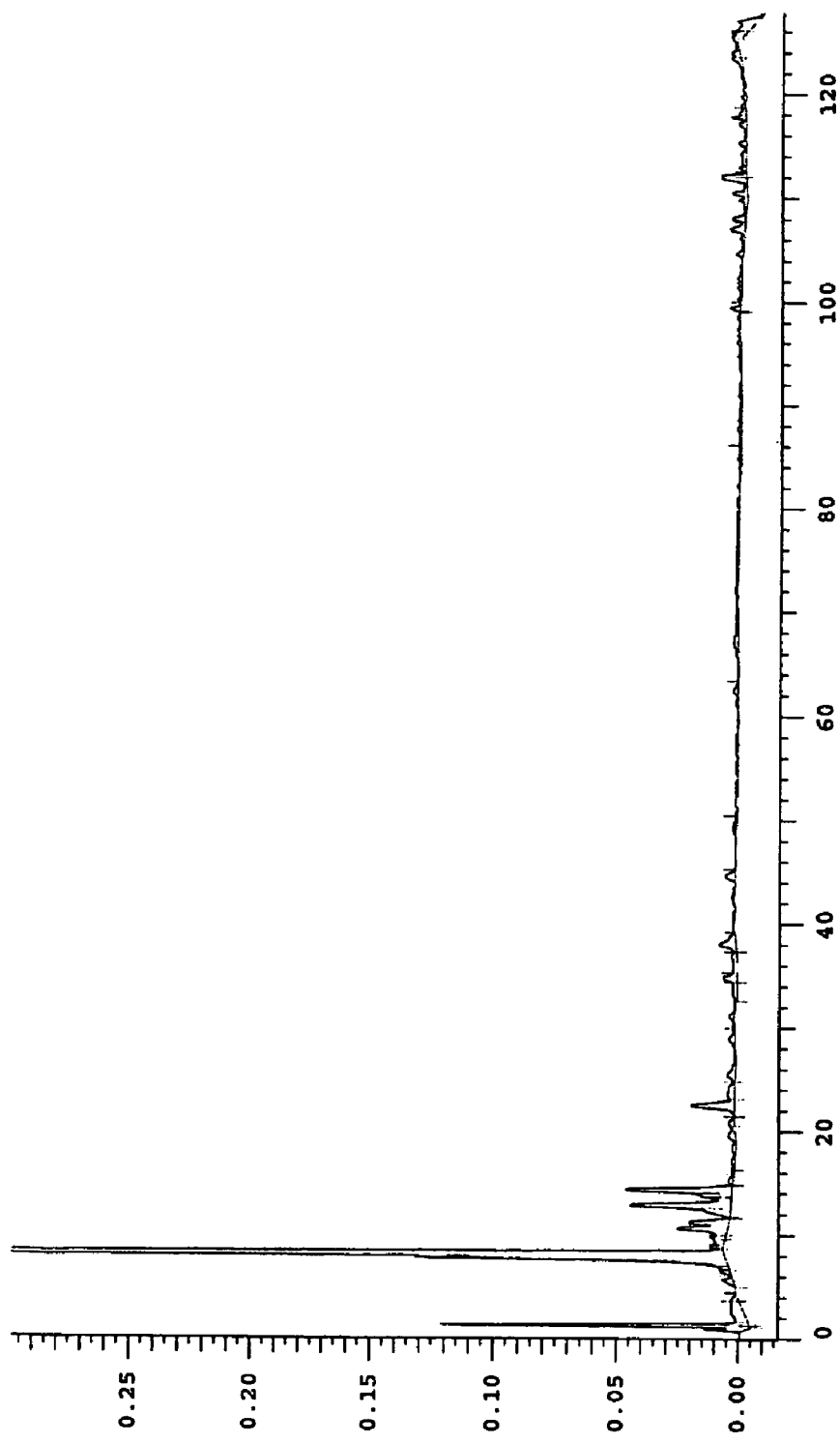
FIG. 44 an HPLC chromatogram at 280 nm of the combined 50% and 90% ethanol elution fractions collected during elution of a plum concentrate from a protonated tertiary amine-substituted polystyrene resin.
Figure 45:
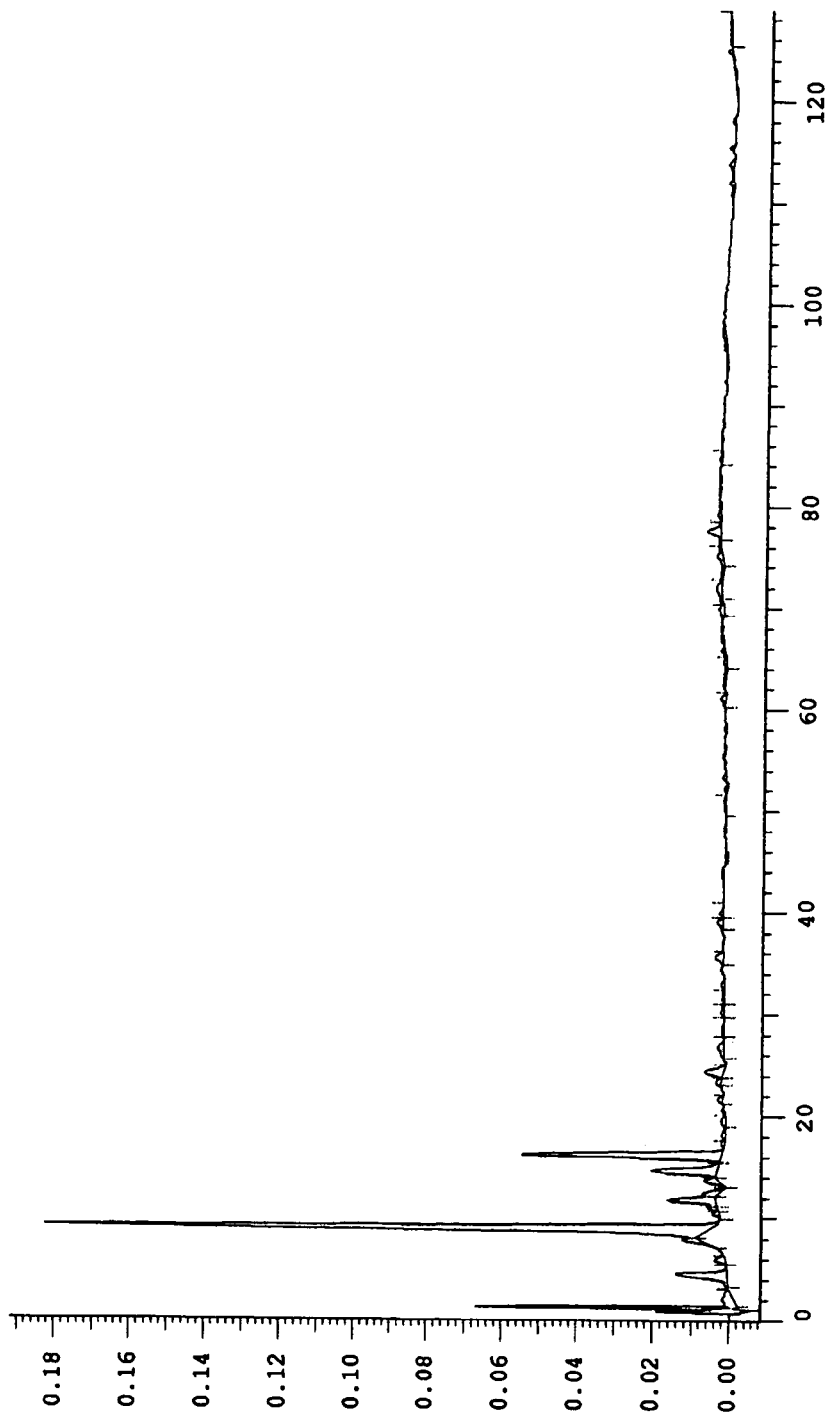
FIG. 45 is an HPLC chromatogram at 280 nm of the combined 50% and 90% ethanol elution fractions collected during elution of a plum concentrate from a brominated polystyrene resin.
Figure 50:
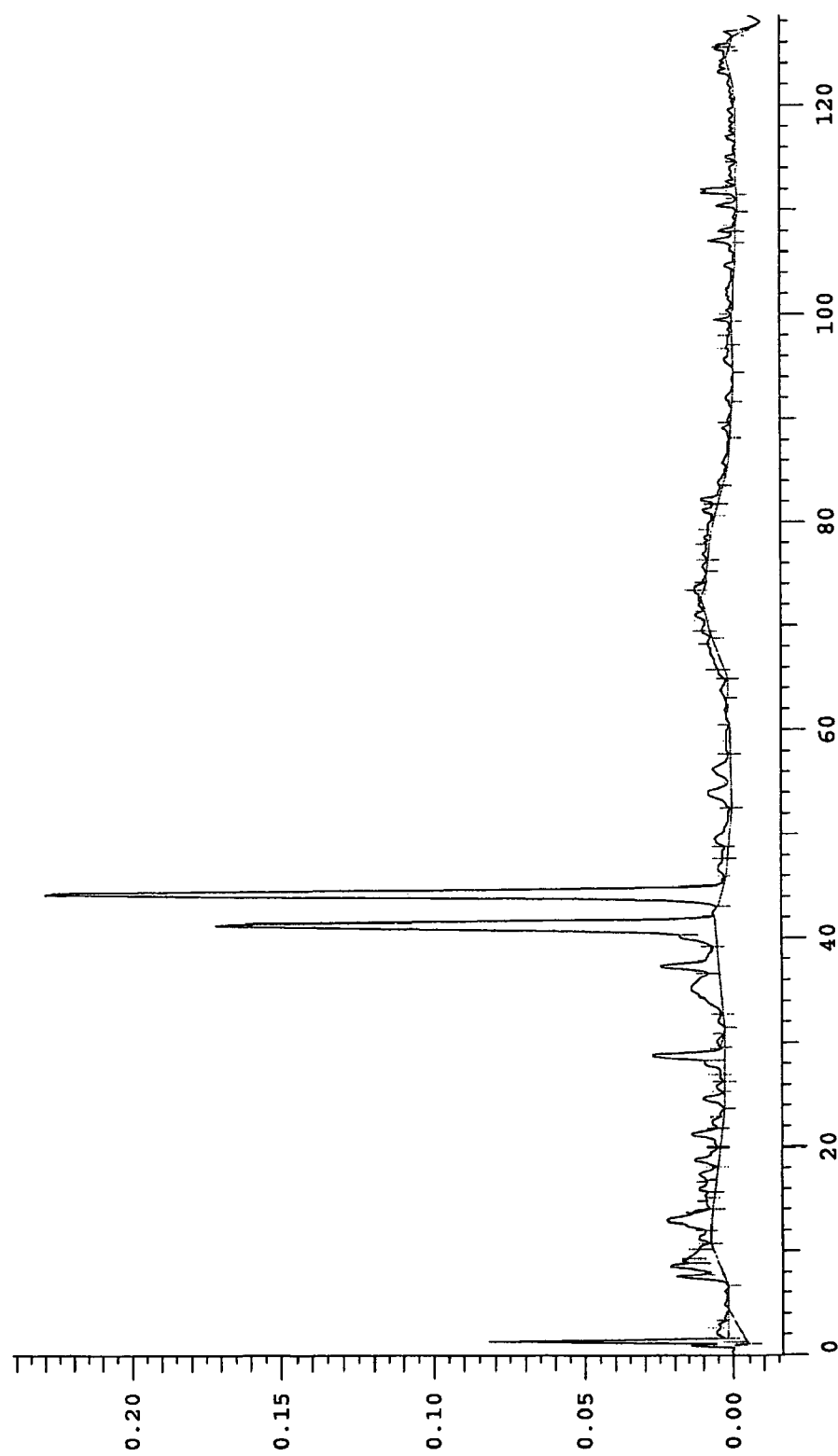
FIG. 50 is an HPLC chromatogram at 280 nm of a purified black raspberry composition.
Figure 51:
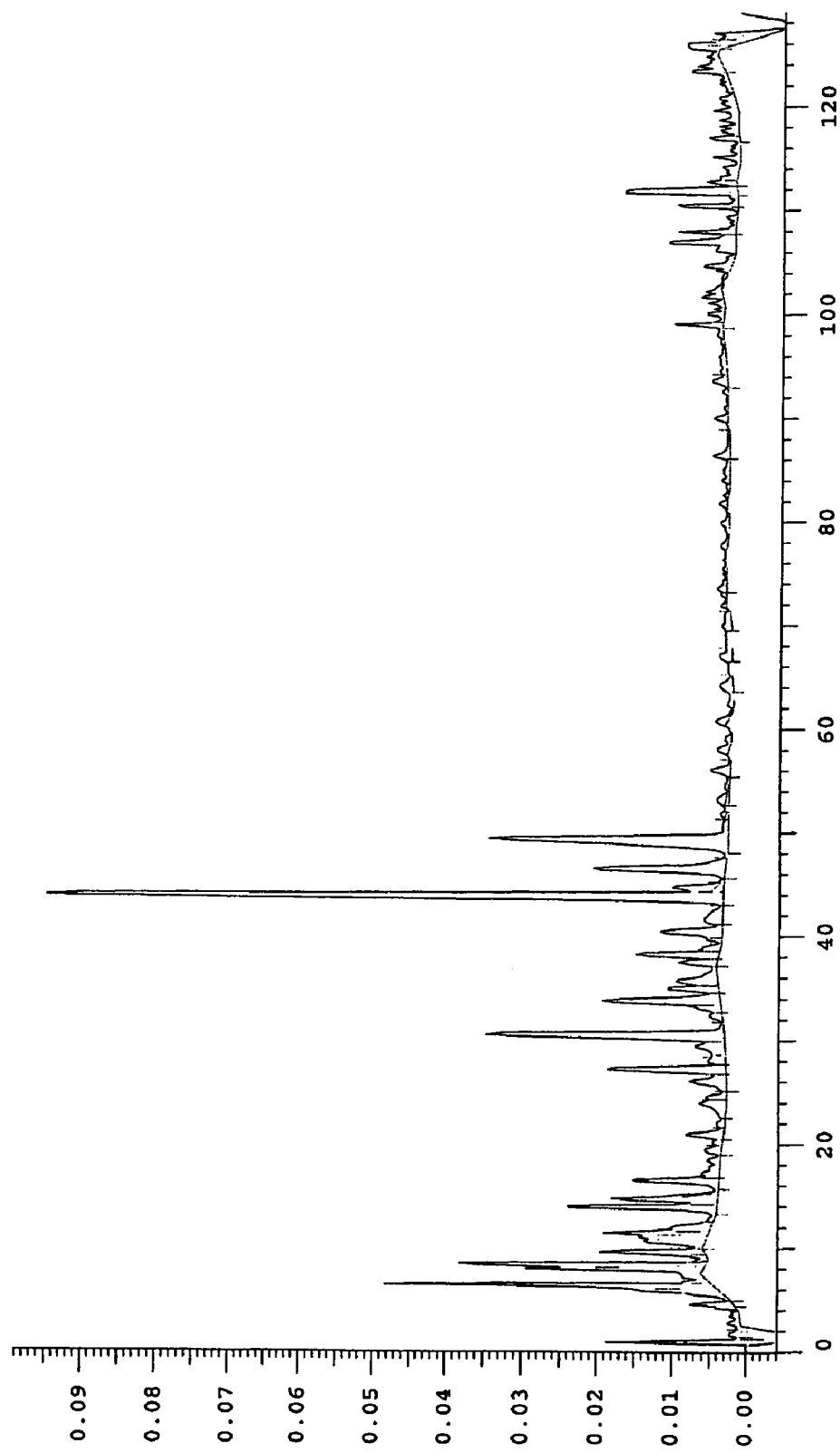
FIG. 51 is an HPLC chromatogram at 280 nm of a purified strawberry composition.
Figure 52:
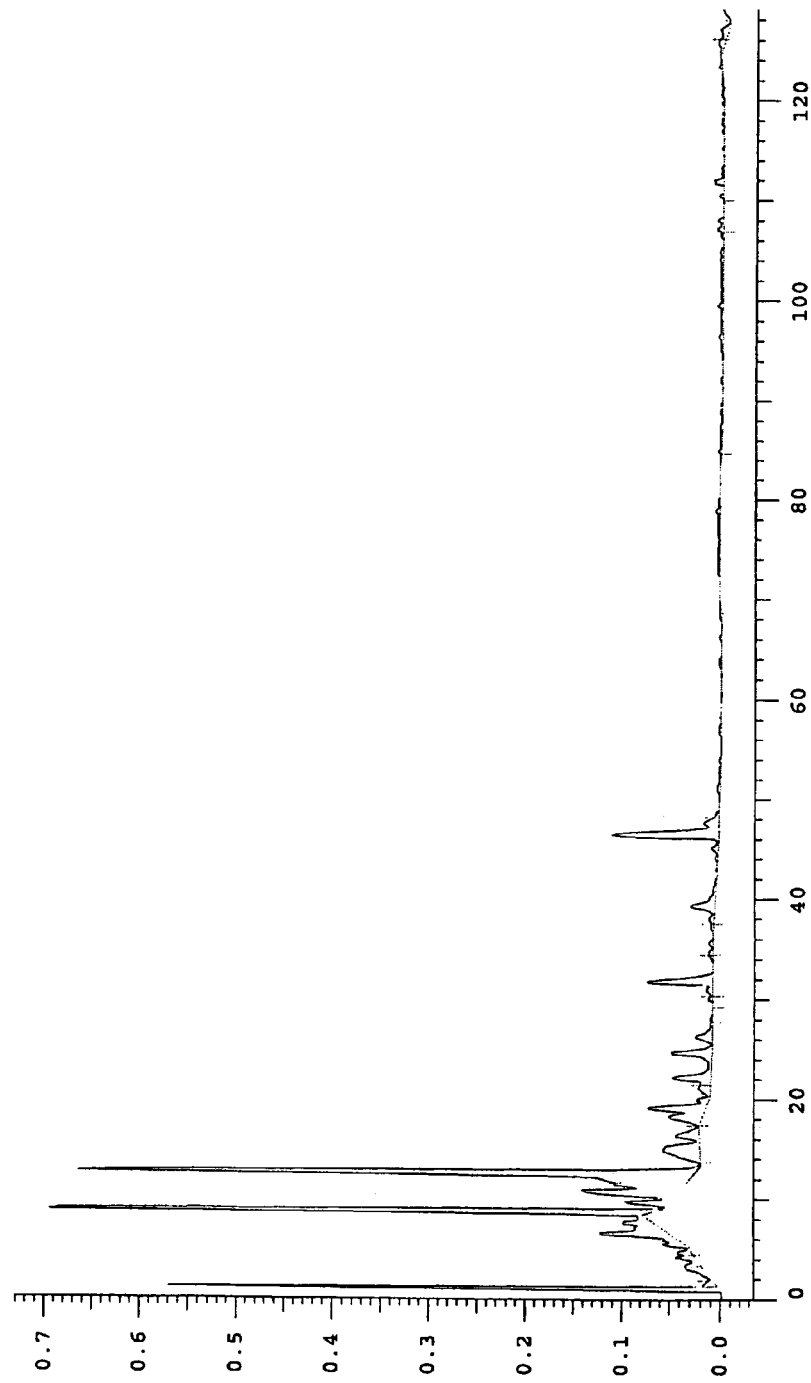
FIG. 52 is an HPLC chromatogram at 280 nm of a purified pomegranate composition.
Figure 53:
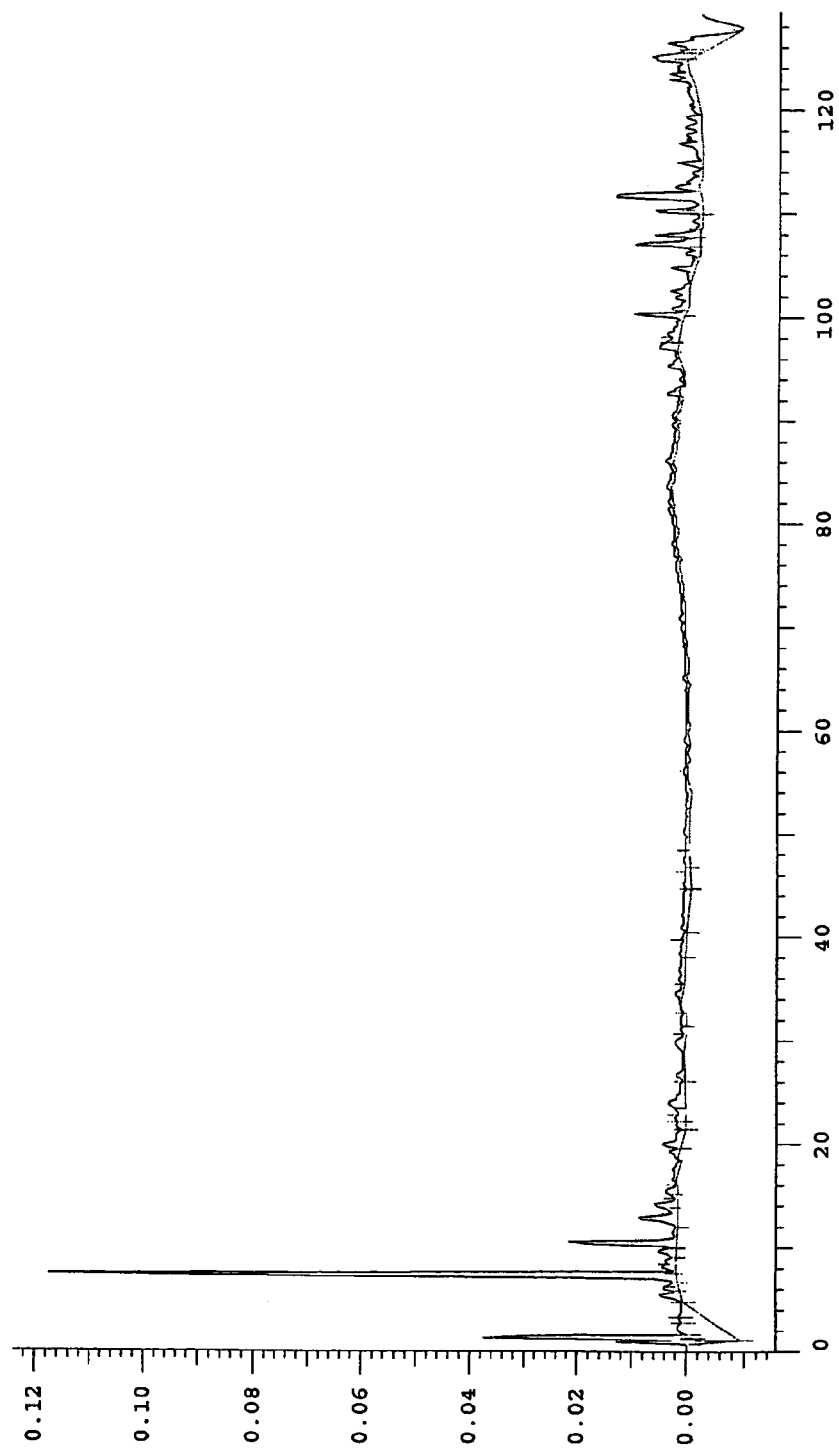
FIG. 53 is an HPLC chromatogram at 280 nm of a purified olive composition.
Figure 54:
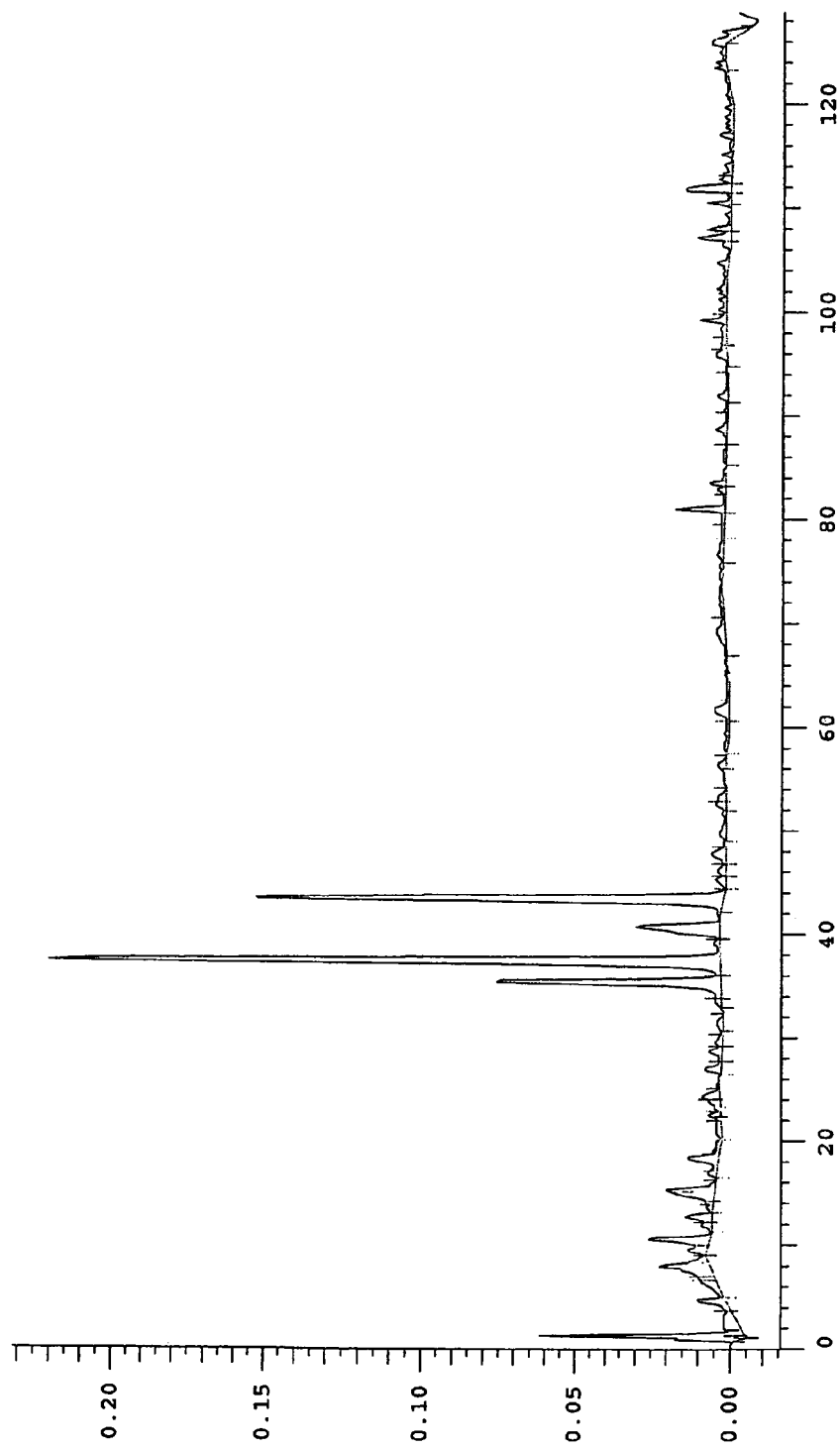
FIG. 54 is an HPLC chromatogram at 280 nm of a purified black currant composition.
Figure 55:
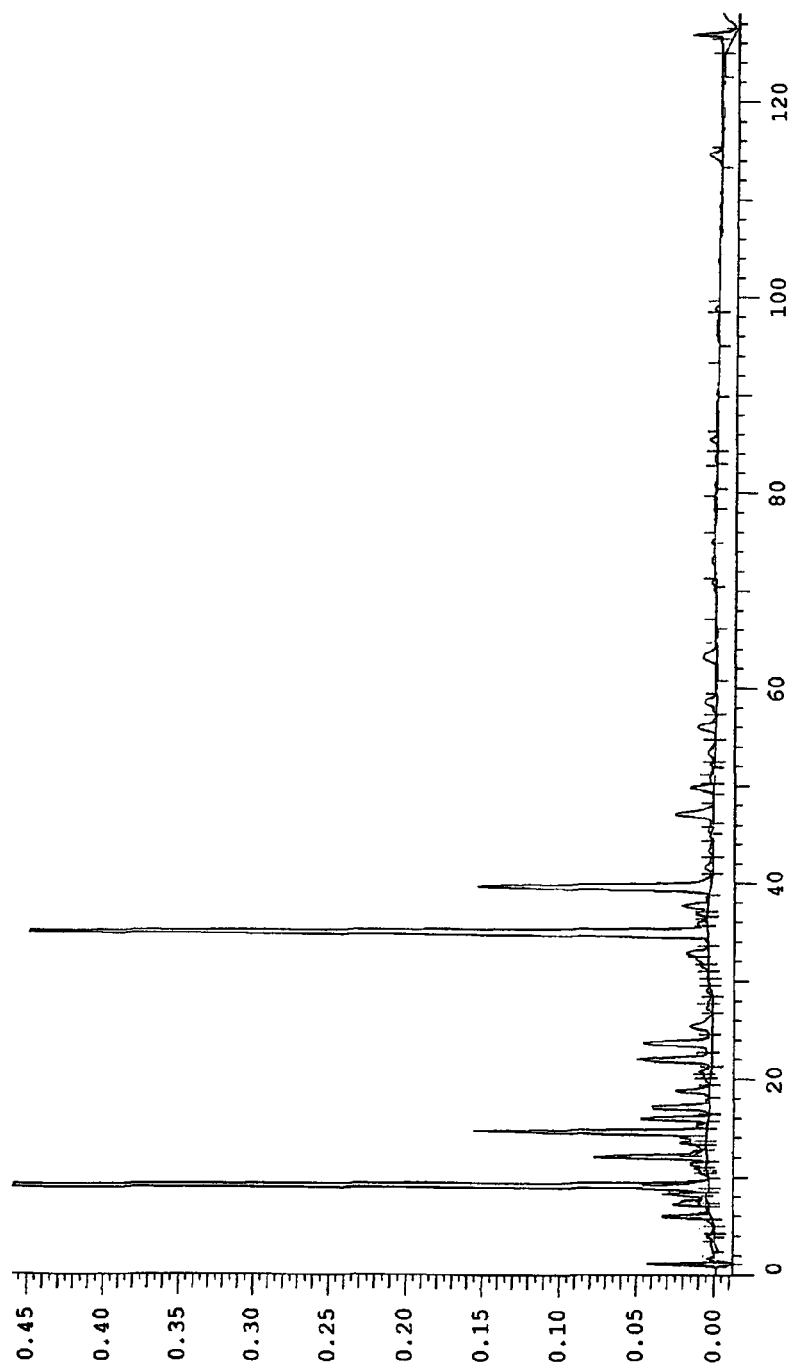
FIG. 55 is an HPLC chromatogram at 280 nm of a purified cherry composition.
Figure 56:
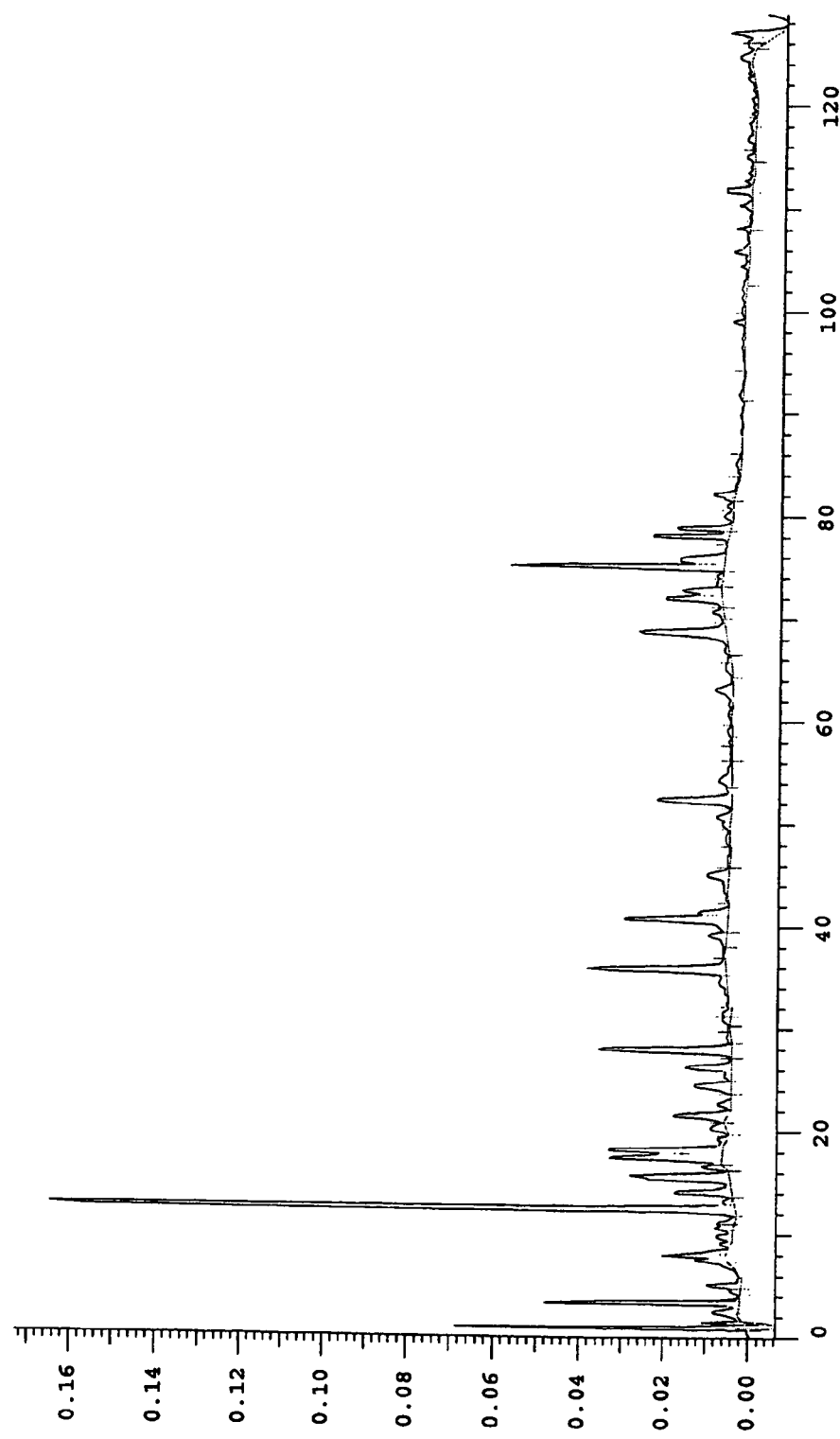
FIG. 56 is an HPLC chromatogram at 280 nm of a purified grape skin composition.
Figure 57:
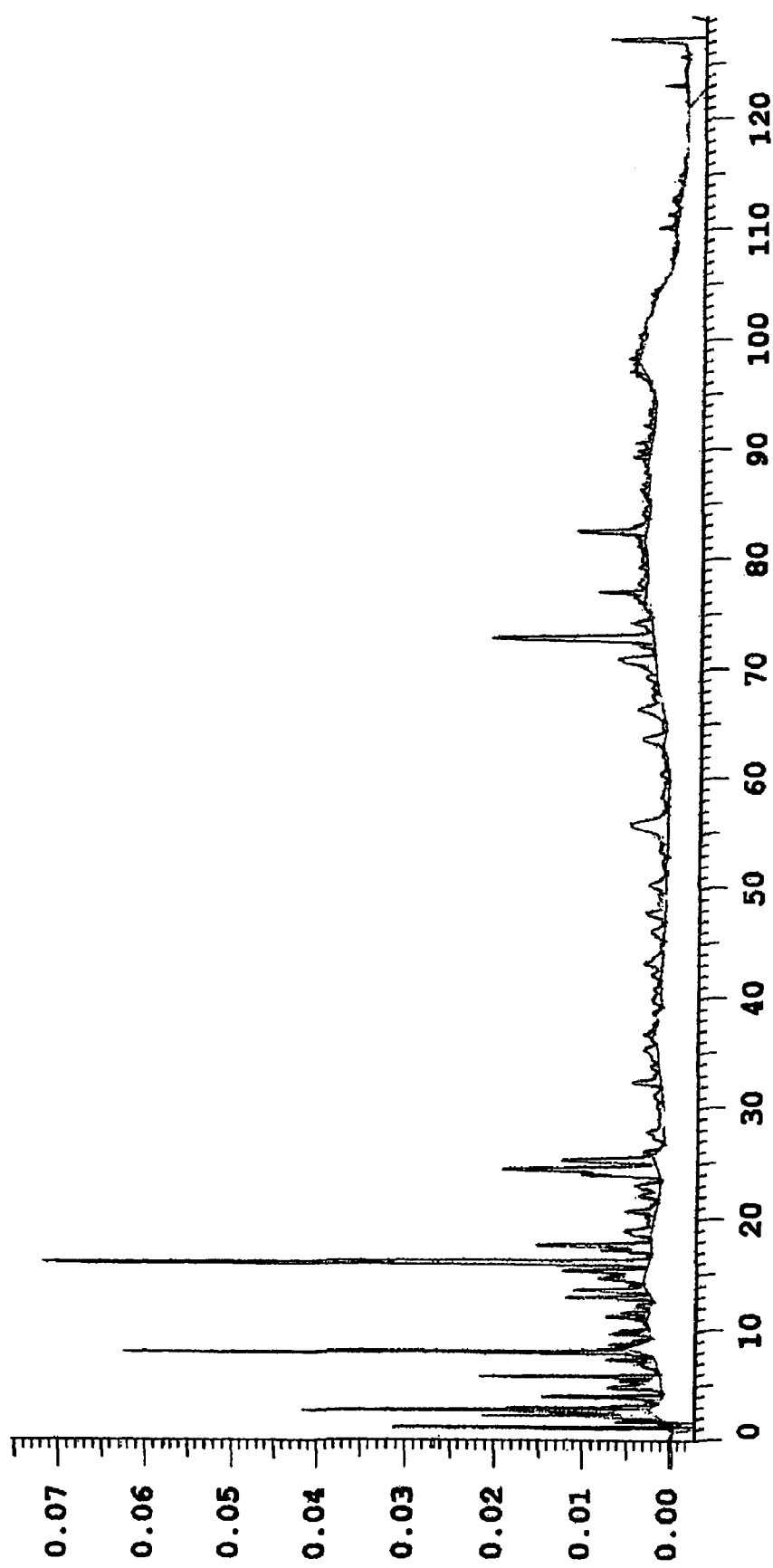
FIG. 57 is an HPLC chromatogram at 280 nm of a purified apple composition.
Figure 58:
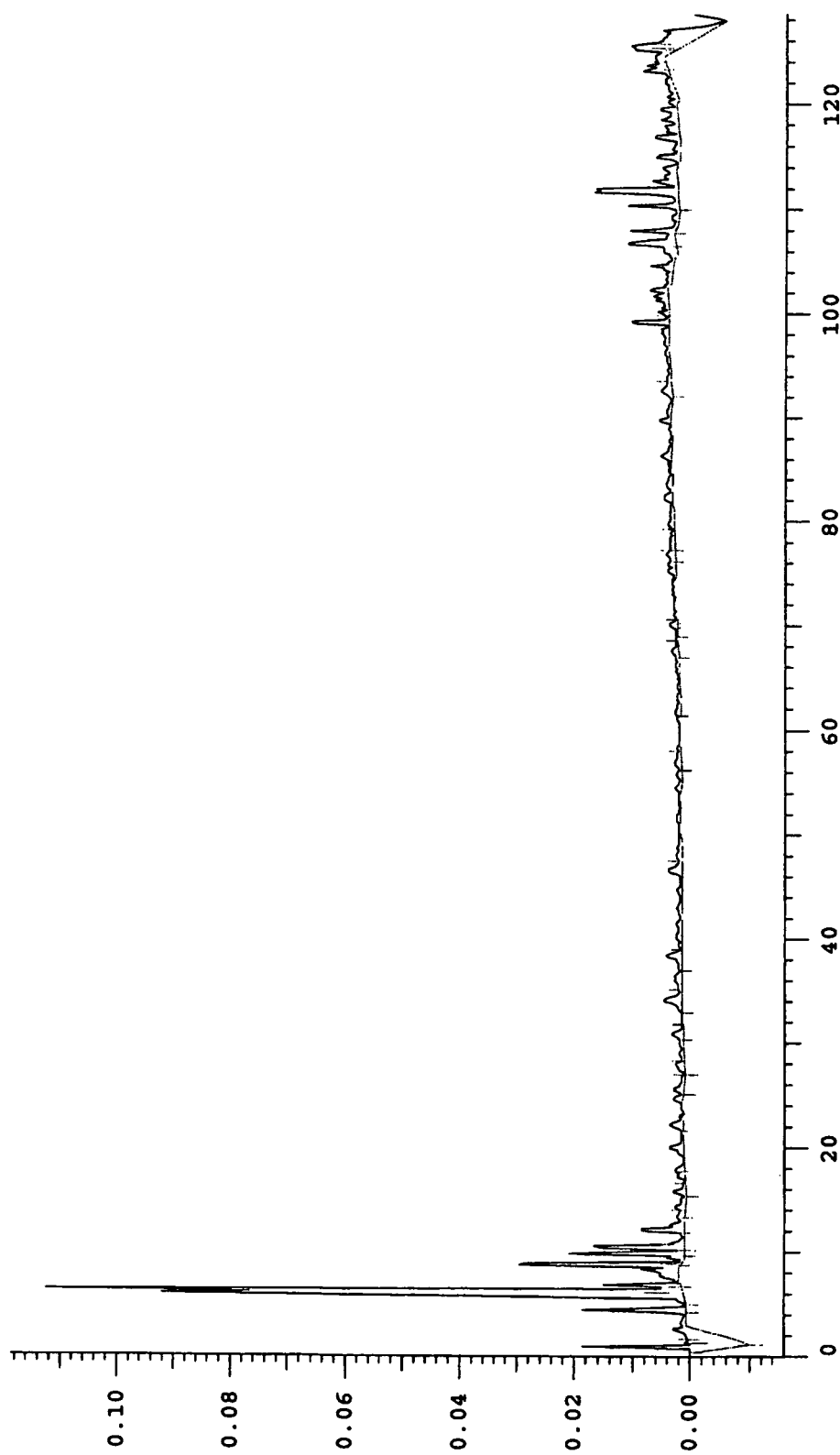
FIG. 58 is an HPLC chromatogram at 280 nm of a purified banana peel composition.
Figure 59:
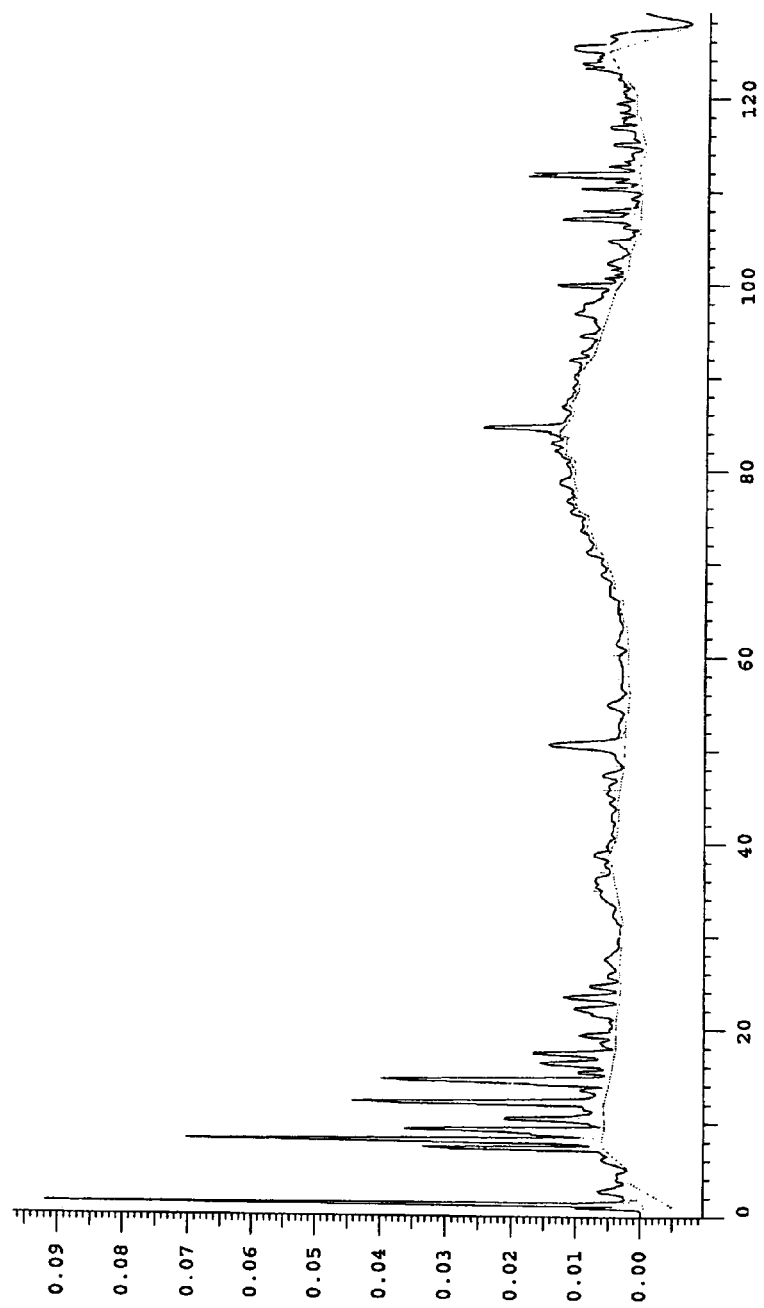
FIG. 59 is an HPLC chromatogram at 280 nm of a purified hawthorn berry composition.
Figure 60:
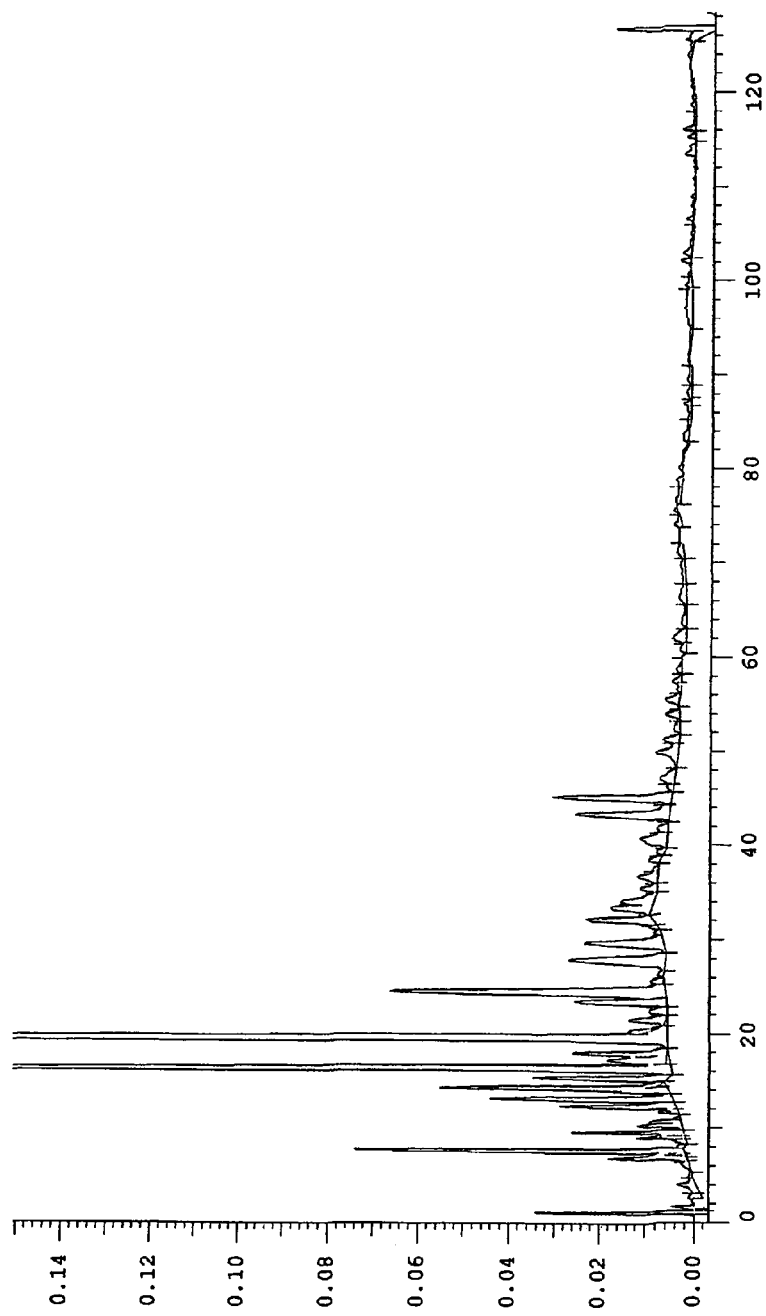
FIG. 60 is an HPLC chromatogram at 280 nm of a purified mangosteen hull composition.
Figure 61:
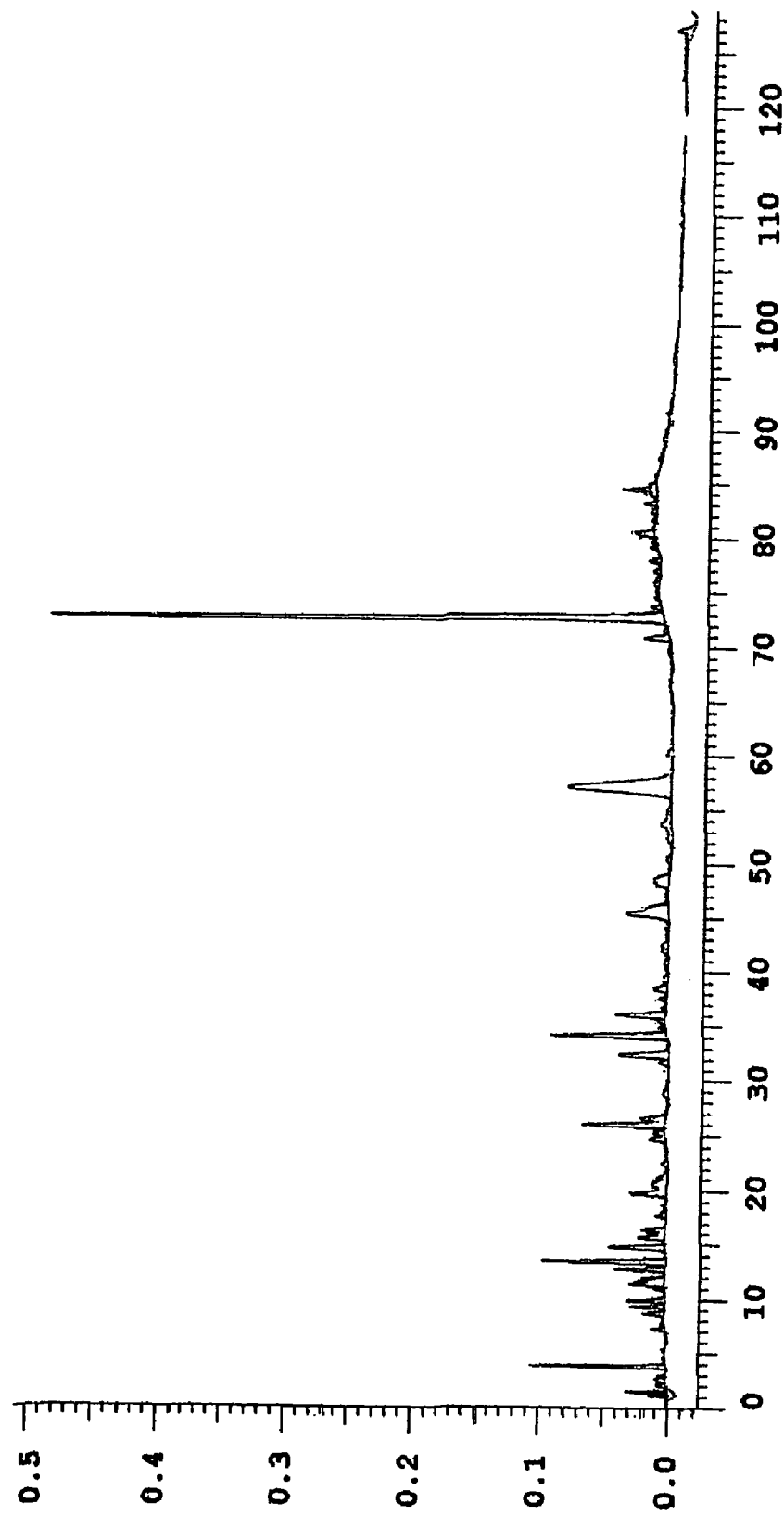
FIG. 61 is an HPLC chromatogram at 280 nm of a purified orange peel composition.

| Plant material | proanthocyanidins (wt %) | HPLC |
| --- | --- | --- |
| cranberry | 6.8-18.3 | FIGS. 41-43, 46-49 |
| blueberry | 8.4-11.2 | FIGS. 4-5, 26-29, 37-38 |
| elderberry | 4.4-10.5 | FIGS. 6-13, 16-25 |
| plum | 5-9.8 | FIGS. 44-45 |
| black raspberry | 10-11 | FIG. 50 |
| strawberry | 5 | FIG. 51 |
| pomegranate | 12-13.1 | FIG. 52 |
| olive | 15-16.7 | FIG. 53 |
| black currant | 5-5.4 | FIG. 54 |
| cherry | 5 | FIG. 55 |
| grape skin | 8.5-12.5 | FIG. 56 |
| apple | 7.2-10 | FIG. 57 |
| banana peel | 3.8-9.7 | FIG. 58 |
| hawthorn berry | 18-21.5 | FIG. 59 |
| mangosteen hull | 2.8-22.9 | FIG. 60 |
| orange peel | 8-10 | FIG. 61 |

Example 24

Alternative Quantitative HPLC Method for Determination of Percent Proanthocyanidins This alternative HPLC method, which is used to determine the amount of proanthocyanidins in various fractions and enriched compositions, uses catechin as the external standard. Each type of sample requires a different preparation and is prepared as described in Example 9. The method uses a 5 µm Zorbax column packed with Stablebond SBC-18 in a 150×4.6 mm column. The flow rate was 1.5 mL/minutes, the detector was set at 280 nm, the injection volume was 10 µL, and the run time was 24 minutes. The mobile phase was: channel A=100% acetonitrile; channel B=0.1% trifluoroacetic acid in water; channel C=100% methanol. The gradient employed is provided in Table 15. The proanthocyanidins typically eluted as a group of broad peaks in the HPLC chromatogram at elution times between 11-22 minutes.

To prepare the catechin standard, accurately weigh 100 mg of catechin (Aldrich; Milwaukee, Wis.) into a 100 mL volumetric flask. Add 70 mL of 50% methanol/water and sonicate for 5 minutes until dissolved. Dilute to volume using 50% methanol/water, cap, and mix until homogeneous. Analyze the prepared standard using the HPLC method described in this Example. The peak area response factor for the catechin standard is then determined by dividing the peak area by the product of the standard's concentration and its purity as shown in Equation 10:

$$RF = \frac{PA}{C_{std} \times P_{std}} \qquad \text{Eq. 10}$$

where RF=peak area response factor for the standard (area units/mg/mL); PA=peak area of the catechin peak in the chromatogram; $C_{std}$=concentration of the standard solution in mg/mL; and $P_{std}$=standard purity as a percent (usually 0.98).

The percent proanthocyanidins in a sample can be determined using the sample preparation and HPLC analysis method described above. The total peak area in the 11-22 minute retention time range is determined for the sample in question. Before any calculation can be made, however, the peak areas of non-proanthocyanidin compounds in the proanthocyanidin retention time range must be subtracted from the overall total peak area. Non-proanthocyanidin compounds often appear as sharp peaks co-eluting with or on top of the broad proanthocyanidins' peak, and their UV spectrum by diode array is often different from the bulk of the proanthocyanidin peak. To determine the peak area of non-proanthocyanidin peaks, manually integrate these peaks, total their peak area and subtract this area from the total 11-22 minute peak area. Once the net area of the proanthocyanidins' peak in the sample has been determined, divide this value by the peak area response factor for the in-house standard to obtain the concentration of proanthocyanidins in the sample as shown in Equation 11:

$$C_{proanthos} = \frac{PA_{samp} \times DF}{RF} \qquad \text{Eq. 11}$$

where $C_{proanthos}$=concentration of total proanthocyanidins in the sample (mg/mL); $PA_{samp}$=corrected total peak area for the sample; DF=dilution factor (1 for dry biomass, 2 for fresh/frozen biomass, and 1 for an enriched composition); and RF=peak area response factor calculated using Equation 10.

The percent total proanthocyanidins is calculated as shown in Equation 12:

$$\% \text{ Proanthocyanidins} = \frac{C_{proanthos} \times V \times 100}{W_s} \qquad \text{Eq. 12}$$

where % Proanthocyanidins=percent of total proanthocyanidins in the sample; $C_{proanthos}$=concentration of total proanthocyanidins (mg/mL); V=volume of the sample preparation (usually 250 mL for dry biomass, 100 mL for fresh/frozen biomass, or 10 mL for enriched compositions); and $W_s$=weight of the biomass or enriched composition used in the sample preparation (usually 12,000 mg for dry biomass, 500-1500 mg for fresh/frozen biomass, or 50-100 mg for enriched compositions).

TABLE 15

HPLC gradient for % analysis for proanthocyanidins

| Time (min.) | % A | % B | % C |
|---|---|---|---|
| 0 | 14 | 78 | 8 |
| 9 | 14 | 78 | 8 |
| 17 | 34 | 58 | 8 |
| 22 | 34 | 58 | 8 |
| 22.1 | 14 | 78 | 8 |
| 26 | 14 | 78 | 8 |

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of preparing a composition enriched in phenolic compounds, comprising:
   a) providing a crude extract of one or more plant materials that contain phenolic compounds, said extract comprising proanthocyanidins, anthocyanins, and polar non-phenolic compounds;
   b) filtering said crude extract;
   c) contacting said filtered extract with a substituted polymer resin consisting essentially of aromatic rings substituted with one or more electron-withdrawing groups and operative to releasably absorb said phenols but not retain said polar non-phenolic compounds;
   d) washing said resin with a wash eluent to elute said polar non-phenolic compounds;
   e) eluting the resin with a first eluent and collecting a first fraction containing phenolic compounds;
   f) eluting the resin with a second eluent and collecting a second fraction containing phenolic compounds; and g) isolating the fraction from step e) or step f) or combining said fractions from steps e) and f) to obtain a composition enriched in phenolic compounds, wherein said composition has decreased levels of said polar non-phenolic compounds as compared to levels of polar non-phenolic compounds in the crude extract.

2. The method of claim 1, wherein said electron withdrawing group is selected from the group consisting of F, Cl, Br, I, protonated alkyl amines, sulfonic acids, trihalomethyl, and COOH.

3. The method of claim 1, wherein said resin is a protonated tertiary amine-substituted styrene divinylbenzene copolymer.

4. The method of claim 1, wherein said crude extract is prepared by extracting dried or fresh plant material(s) with an acidified extraction solvent.

5. The method of claim 4, wherein said acidified extraction solvent comprises an aqueous solution having between about 0-95% ethanol and between about 0-3% acid or an aqueous solution having between about 0-100% methanol and between about 0-3% acid.

6. The method of claim 5, wherein said acid is sulfuric acid, acetic acid or hydrochloric acid.

7. The method of claim 1, wherein said wash eluent contains at least 0.003% acid.

8. The method of claim 7, wherein said acid is acetic acid, hydrochloric acid or sulfuric acid.

9. The method of claim 1, wherein said first eluent comprises between about 50 and 70% ethanol in water and 0.003% acid.

10. The method of claim 9, wherein said acid is acetic acid, hydrochloric acid or sulfuric acid.

11. The method of claim 1, wherein said second eluent comprises between about 70 and 90% ethanol in water.

12. The method of claim 1, wherein said composition comprises between about 10-80% of said phenolic compounds.

13. The method of claim 12, wherein said composition comprises at least 12% of said phenolic compounds.

14. The method of claim 12, wherein said composition comprises at least 25% of said phenolic compounds.

15. The method of claim 1, wherein said plant material is selected from the group consisting of blueberries, bilberries, elderberries, plums, blackberries, strawberries, red currants, black currants, cranberries, cherries, red raspberries, black raspberries, grapes, currants, hibiscus flowers, bell peppers, beans, peas, red cabbage, purple corn, violet sweet potatoes, olives, pomegranates, mangosteens, apples, hawthorn, gooseberries, and oranges, and includes the whole plant material or the skins, peels, fruits, nuts, hulls or seeds thereof.

16. The method of claim 1, wherein step (a) further comprises adding pectinase to said crude extract.

17. The method of claim 16, wherein said pectinase is present in an amount between about 0 and 0.12% by weight of said plant material.

18. The method of claim 1, further comprising adding an excipient to said composition.

19. The method of claim 18, wherein said excipient is selected from the group consisting of preservatives, carriers, buffering agents, thickening agents, suspending agents, stabilizing agents, wetting agents, emulsifying agents, coloring agents and flavoring agents.

20. The method of claim 1, further comprising
h) loading said composition from step e), said composition from step f), or said composition from step g) onto a low pressure vacuum liquid chromatography column packed with a reversed-phase lipophilic resin and collecting fractions that elute during said loading;

i) eluting said resin with water;

j) combining fractions from steps h) and i) to obtain a first composition enriched in polar proanthocyanidins; and k) eluting said resin with increasing amounts of a polar organic solvent to obtain a second composition enriched in non-polar proanthocyanidins.

21. The method of claim 20, further comprising purifying said first composition by reversed-phase preparative HPLC.

22. The method of claim 21, further comprising purifying said second composition by gel filtration or preparative HPLC.

23. A purified plant material-based composition enriched for phenolic compounds prepared without the addition of sulfites, wherein the composition is an extract containing at least 10% of proanthocyanins and decreased levels of anthocyanins as compared to levels of anthocyanins in the original plant material.

24. The composition of claim 23, wherein said plant material is selected from the group consisting of blueberries, bilberries, cranberries, blueberries, elderberries, plum, raspberries, strawberries, pomegranates, olives, red currants, black currants, cherry, grapes, apples, bananas, hawthorn, mangosteens, orange peels, and gooseberries, and includes the whole plant material or the skins, peels, fruits, nuts, hulls or seeds thereof.

25. The composition of claim 24 comprising between about 5-30% proanthocyanidins by weight of said composition.

26. A method of preparing compositions selectively enriched in proanthocyanidins with decreased concentrations of anthocyanins and polar non-phenolic compounds, comprising:

(a) extracting one or more plant materials containing proanthocyanidins with a solvent to provide a crude extract containing phenolic compounds, said extract comprising proanthocyanidins, anthocyanins, other small phenolics and polar non-phenolic compounds;

(b) filtering the crude extract by means other than size exclusion filtration;

(c) contacting the crude extract with a resin comprising unsubstituted aromatic rings which retains said anthocyanins and releasably adsorbs said proanthocyanidins but does not retain the polar non-phenolic compounds, without the addition of bisulfite ions;

(d) washing said resin with a wash eluent to elute said polar non-phenolic compounds;

(e) eluting the resin at with a first eluent and collecting a first fraction containing said proanthocyanidins;

(f) eluting the resin with a second eluent and collecting a second fraction containing said proanthocyanidins; and (g) isolating the fractions from step (e) or from step (f) or combining said fractions from steps (e) and (f) to obtain a composition enriched in said proanthocyanidins and decreased levels of said polar non-phenolic compounds and anthocyanins in the crude extract.

27. The method of claim 26, wherein said resin is a polystyrene divinylbenzene copolymer.

28. The method of claim 26, wherein said contacting and washing steps are performed at about room temperature.

29. The method of claim 26, wherein said plant material is selected from the group consisting of blueberries, bilberries, elderberries, plums, blackberries, strawberries, red currants, black currants, cranberries, cherries, red raspberries, black raspberries, grapes, currants, hibiscus flowers, bell peppers, beans, peas, red cabbage, purple corn, violet sweet potatoes, olives, pomegranates, mangosteens, apples, hawthorn, gooseberries, and oranges, and includes the whole plant material or the skins, peels, fruits, nuts, hulls, or seeds thereof.

* * * * *